US008445426B2

(12) United States Patent
De Vos et al.

(10) Patent No.: US 8,445,426 B2
(45) Date of Patent: May 21, 2013

(54) PEPTIDES AND METHODS FOR PRODUCING THEM

(75) Inventors: Willem Meindert De Vos, Ede (NL); Airi Palva, Helsinki (FI); Ilkka Palva, Helsinki (FI); Justus Reunanen, Kerava (FI); Ingemar Von Ossowski, Helsinki (FI); Reetta Satokari, Kirjala (FI); Satu Vesterlund, Naantali (FI); Matti Kankainen, Helsinki (FI); Tuomas Salusjärvi, Espoo (FI); Soile Tynkkynen, Helsinki (FI)

(73) Assignee: Valio Ltd., Helsinki (FI)

( * ) Notice: Subject to any disclaimer, the term of this patent is extended or adjusted under 35 U.S.C. 154(b) by 963 days.

(21) Appl. No.: 12/364,128

(22) Filed: Feb. 2, 2009

(65) Prior Publication Data

US 2010/0196524 A1    Aug. 5, 2010

(51) Int. Cl.
A61K 35/74    (2006.01)

(52) U.S. Cl.
USPC ......... 514/1.1; 426/656; 435/252.1; 424/780; 530/350

(58) Field of Classification Search
None
See application file for complete search history.

(56) References Cited

U.S. PATENT DOCUMENTS

| 5,843,698 | A | 12/1998 | Sorensen |
| 6,074,815 | A | 6/2000 | Sorensen |
| 6,150,127 | A | 11/2000 | Sorensen |
| 2004/0009490 | A1 | 1/2004 | Glenn et al. |

FOREIGN PATENT DOCUMENTS

| WO | WO 02/060276 A1 | 8/2002 |
| WO | WO 2006/113033 A1 | 10/2006 |

OTHER PUBLICATIONS

Database UniProt, 2006,database accession No. Q03BW3.*
Makarova et al., Proc. Natl. Acad. Sci., USA, 2006, 103(42), 15611-15616.*
Scott et al., Molecular Microbiology, 2006, 62(2), 320-330.*
Ouwehand et al., International Dairy Journal, 1999, 9, 623-630.*
Search Reports in Finnish patent application Nos. 2009/6047 and 2009/6049.
Maze et al, Lactobacillus casei BL23 complete genome sequence, database UniProt, accession B3W7W6 (Feb. 9, 2008). Retrieved from: EBI UniProt [online]; accession B3W7W6 [haettu Jan. 15, 2010] Aminohapot 1-237.
Chaillou et al, Intraspecies Genomic Diversity and Natural Population Structure of the Meat-Borne Lactic Acid Bacterium Lactobacillus sakei, database UniProt, accession B2Y6D6 (Jan. 7, 2008). Retrieved from: EBI Uiprot [online], aminohapot 1-146.
Munoz-Provencio et al, Adhesion properties of Lactobacillus casei strains to resected intestinal fragments and components of the extracellular matrix. Arch. Microbiol., 2009, vol, 191, s. 153-161; s.153, osan "Introduction" ensimmainen kappale—s. 154, vasen palsta; s. 156, osa "Binding to human colon fragments ex vivo"; s. 158, osa "Discussion".
Maze et al, Lactobacillus casei BL23 complete genome sequence, database UniProt, accession B3W7W7 (Feb. 2, 2008). Retrieved from: EBI UniProt [online], aminohapot 1-334.
Database UniProt [online], Nov. 14, 2006, "SubName: Full=Uncharacterized protein encoded in toxicity protection region of plasmid R478, contains von Willebrand factor (VWF) domain;" XP002579086 retrieved from EBI accession No. UNIPROT: Q03BW3.
Database UniProt [Online], Nov. 4, 2008, "SubName: Full=Sortase (Surface protein transpeptidase);" XP002579056 retrieved from EBI accession No. UNIPROT: B5QRG6.
Mandlik et al, "The molecular switch that activates the cell wall anchoring step of pilus assembly in gram-positive bacteria", Proceedings of the National Academy of Sciences of the United States of America, vol. 105, No. 37, Sep. 2008, pp. 14147-14152, XP02579057.
Van Pijkeren et al, "Comparative and functional analysis of sortase-dependent proteins in the predicted secretome of Lactobacillus salivarius UCC118", Applied and Environment Microbiology Jun. 2006 LNKEDed—PUBMED: 16751526, vol. 72, No. 6, Jun. 2006, pp. 4143-4153, XP002579058.
Kankainen et al, "Comparative genomic analysis of Lactobacillus rhamnosus GG reveals pili containing a human-mucus binding protein", Proceedings of the National Academy of Sciences of the United States of America, Oct. 6, 2009 LNKD—PUBMED:19805152, vol. 106, No. 40, pp. 17193-17198 + Sup, XP002579059.
Database UniProt [online] Oct. 13, 2009, "SubName: Full=Pilus specific protein, ancillary protein involved in mucus-adhesion, contains von Willebrand factor (VWF) domain; SubName: Full=Putative cell surface protein;" XP002579087 retrieved from EBI accession No. UNIPROT:C7T9P6.
Partial Search Report in PCT/FI2010/050059 mailed May 11, 2010.
Altschul et al, "Gapped BLAST and PSI-BLAST: a new generation of protein . . . ", Nucleic Acids Research, 1997, vol. 25, No. 17, 3389-3402.
Avall-Jaaskelainen et al, "Surface Display of the Receptor-Binding Region of the . . . ", Applied and Environmental Microbiology, Apr. 2003, vol. 69, No. 4, p. 2230-2236.
Budzik et al, "Amide Bonds Assemble Pili on the Surface of Bacilli", PNAS, Jul. 22, 2008, vol. 105, No. 29, 10215-10220.

(Continued)

*Primary Examiner* — Chris R Tate
*Assistant Examiner* — Roy Teller
(74) *Attorney, Agent, or Firm* — Nixon & Vanderhye P.C.

(57) ABSTRACT

The present invention relates to the fields of life sciences and food, feed or pharmaceutical industry. Specifically, the invention relates to novel peptides, pilus structures, polynucleotides as well as vectors, host cells, products and pharmaceutical compositions comprising the polynucleotides, peptides or pilus structures. The invention also relates to gene clusters and antibodies. Furthermore, the present invention relates to methods for producing the peptides or pilus structures or producing the products comprising the peptides or pilus structures. Furthermore, the present invention relates to treatments as well as uses and methods for screening bacterial strains, for reducing or inhibiting the adhesion of pathogenic bacteria, promoting the adhesion of bacterial cells to the mucus and for modifying immune response in a subject. Still, the present invention relates to methods for detecting probiotic bacterial strains or pathogen strains.

16 Claims, 11 Drawing Sheets

OTHER PUBLICATIONS deRegt et al, "High Acquisition and Environmental Contamination Rates . . . ", Journal of Antimicrobial Chemotherapy (2008) 62, 1401-1406.

Delcher et al, "Identifying Bacterial Genes and Endosymbiont . . . ", BIOORMATICS, vol. 23, No. 6 2007, pp. 673-679.

Finn et al, "The Pfam Protein Families Database", Nucleic Acids Research, 2008, vol. 36, D281-D288.

Fuller, "A Review Probiotics in Man and Animals", Journal of Applied Bacteriology, 1989, 66, 365-378.

Goldin et al, "Clinical Indications for Probiotics: An Overview", Clinical Infectious Diseases 2008:46:S96-100 (Suppl 2).

Haft et al, "The TIGRFAMs Database of Protein Families", Nucleic Acids Research, 203, vol. 31, No. 1, 371-373.

Hendrickx et al, "Expression of Two Distinct Types of Pili by a Hospital-Acquired . . . ", Microbiology (2008), 154, 3212-3223.

Johnston et al, "An Evaluation of Several Adjuvant Emulsion . . . ", Laboratory Animal Science, vol. 41, No. 1, Jan. 1991.

Kang et al, "Stabilizing Isopeptide Bonds Revealed in Gram-Positive . . . ", Science, vol. 318, Dec. 7, 2007.

Kingsford et al, "Rapid, Accurate, Computational Discovery of Rho-Independent . . . ", Genome Biology 2007, vol. 8, Issue 2:R22.

Krishnan et al, "An IgG-like Domain in the Minor Pilin GBS52 . . . ", Structure 15, 893-903, Aug. 2007.

Lee et al, "The Coming of Age of Probiotics", Trends in Food Science & Technology, Jul. 1995, vol. 6.

Ljungh e al, "Lactic Acid Bacteria as Probiotics", Curr. Issues Intestinal Microbiol. vol. 7 (2006): 73-90.

Mandlik et al, "The Molecular Switch that Activates the Cell . . . ", PNAS, Sep. 16, 2008, vol. 105, No. 37, 14147-14152.

Mandlik et al, "Pili in Gram-Positive Bacteria: Assembly . . . ", 2008, Trends Microbiol 16, 33-40.

Manley K.J. et al, "Probiotic Treatment of Vancomycin-Resistant . . . ", 2007 Med J Aust. 186(9):454-457.

Miettinen et al, "Lactobacilli and Streptococci . . . ", 2000, J Immunol 164:3733-3740.

Miettinen et al, "Live *Lactobacillus rhamnosus* and *Streptococcus* . . . ", Journal of Leukocyte Biology, vol. 84, Oct. 2008.

Miettinen et al, "Production of Human Tumor Necrosis Factor . . . ", Infection and Immunity, Dec. 1996, vol. 64, No. 12, p. 5403-5405.

Mulder et al, "New Developments in the InterPro Database", Nucleic Acids Research, 2007, vol. 35, Database issue.

Pearson, "Rapid and Sensitive Sequence Comparison . . . ", Methods in Enzymology, 1990, Methods Enzymol 183:63-98.

Pultz et al, "Adhesion of Vancomycin-Resistant Enterococcus . . . ", Current Microbiology, vol. 52 (2006), pp. 221-224.

Salminen et al, "Functional Food Science and Gastrointestinal . . . ", British Journal of Nutrition (1998), 80, Suppl. 1, S147-S-171.

Scott et al, "Pili with Strong Attachments: Gram-positive . . . ", Molecular Microbiology (2006) 62(2), 320-330.

Tannock, "Studies of the Intestinal Microflora: A Prerequisite . . . ", Int. Dairy Journal 8 (1998) 527-533.

Tatusov et al, "The COG database: a Tool for Genome-Scale . . . ", Nucleic Acids Research, 2000, vol. 28, No. 33-36.

Telford et al, "Pili in Gram-positive Pathogens", Nature Reviews/Microbiology, vol. 4, Jul. 2006, 509-519.

Ton-That et al, "Assembly of Pili in Gram-Positive Bacteria", Trends in Microbiology, vol. 12, No. 5, May 2004.

Ton-That et a, Sortases and Pilin Elements Involved . . . , Molecular Microbiology (2004) 53(1), 251-261.

Veckman et al, "*Lactobacilli* and *Streptococci* Induce . . . ", Journal of Leukocyte Biology, vol. 74, Sep. 2003.

Vesterlund et al, "Measurement of Bacterial Adhesion—In Vitro Evaluation . . . ", Journal of Microbiological Methods 60 (2005) 225-233.

Vesterlund et al, "*Staphylococcus aureus* adheres to human intestinal . . . ", Microbiology (2006), 152, 1819-1826.

Vesterlund et al, "Adhesion of Bacteria to Resected Human Colonic . . . ", Research in Microbiology 156 (2005) 238-244.

Wheeler et al, "Database Resources of the National Center for Biotechnology Information", Nucleic Acids Research, 2008, vol. 36, Database issue.

Yanagawa et al, "Electron Microscopy of Fine Structure . . . ", Japanese Journal of Veterinary Research, 16(1): 31, Mar. 1968.

International Search Report in PCT/FI2010/050059 dated Jul. 13, 2010.

Database UniProt [Online] Sep. 2, 2008, "SubName: Full=Fimbriae subunit;" XP002589126 retrieved from EBI accession No. UNIPROT: B3W7W7, Database accession No. B3W7W7.

Scott et al, "Pili with strong attachments: Gram-positive bacteria do it differently", Molecular Microbiology (2006) 62(2), 320-330.

Database UniProt [Online] Sep. 2, 2008, "SubName: Full=Bee2"; XP002589127 retrieved from EBI accession o. UNIPROT: B3W7W6; Database accession No. B3W7W6.

Database UniProt [Online] Oct. 13, 2009, "SubName: Full=Pilus specific protein, major backbone protein; SubName: Full=Putative uncharacterized protein;" XP002589128 retrieved from EBI accession o. UNIPROT: C7T9P4; database accession No. C7T9P4.

Database UniProt [Online] Oct. 13, 2009, "SubName: Full=Pilus specific protein, minor backbone protein; SubName: Full=Putative uncharacterized protein;"XP002589129 retrieved from EBI accession o. UNIPROT:C7T9P5, database accessionNno. C7T9P5.

Makarova et al, "Uncharacterized protein encoded in toxicity protection region of plasmid R478, contains von Willebrand (vWB) domain [*Lactobacillus casei* ATCC 334]", database GenBank, accession ABJ69309, (Nov. 10, 2007), Retrieved from: CAS Registry [online], accession 912207-07-9.

Kirjavainen et al, "Effects of Orally Administered Viable *Lactobacillus rhamnosus* GG . . . ", Clinical and Diagnostic Laboratory Immunology, Marraskuu 1999, s. 799-802, tiivistelma.

* cited by examiner

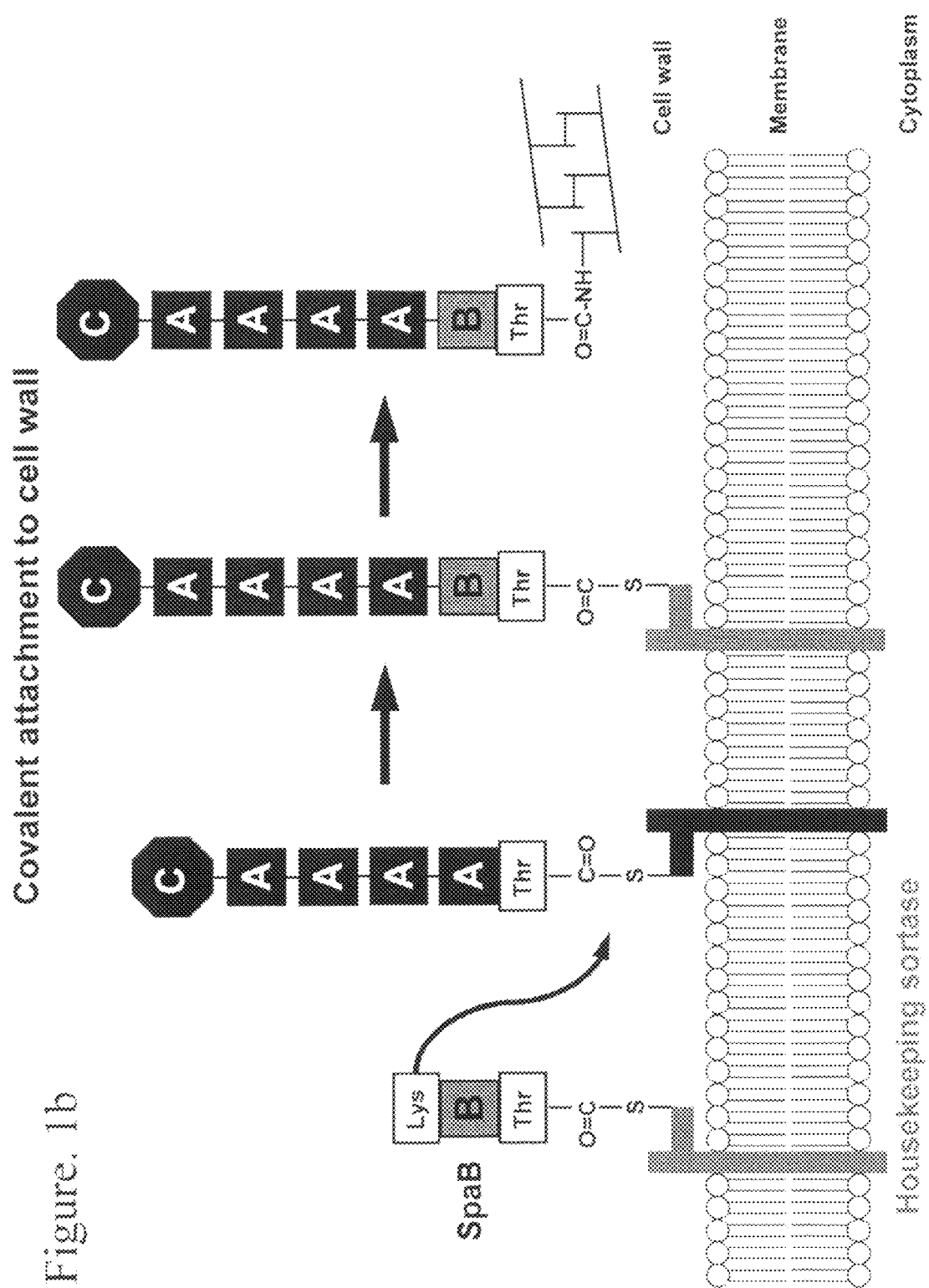

GG00441-GG00444_coding_strand
acgatggttcagtgcggattggactgcttgaatttcaaccagggtaactgctctgagggacttcccttcgggaagaattccct
aagcagtccattggcgttctcgtttgtgccacgctcccaaggcgagtacggatgtgcgaagtaaatctgggttccaacaatct
ctgataacttggcaaactcggaaccattgtcaaaagtgatactctcaaattccttggccccgtagtcgtcgatcgtgtcctgca
aggctttaaggcaggtgtccgcatgatagtcaggaatcttgacgatgatctcagtccggctgtaccgttctgtgagcgtcatt
aatgctggctcatcagctaagcgaataccttgaccaagtcgccttcccaatgtcccacgcctgtgcggtcattcacggccg
caggacgcaactcgattgagtcgccgtatatcttcttattcttgcgcttgtgggcgttcttatagcctttgatgcggcgtcggag
cttcttgggaagtgtcatgttgtctagcgcaagcagcccggcgtcgatgtagcgatacacagttgtcgttgaagggcaagcc
ttgccctggtcgcgatagaagtgtacgaagctatcaacgctgtgtacgcgcggcttacgagtaagctccctggcgagagcc
ttgaagaacgcacggccggtcttaagaaaggcgtagtgaccggttctatcgcgtttacggtcgtgcatggcttgggcagttt
ccgcaagatagacttgatgcgagtgacgcttcgagtcgagctgagttacagatccacgcgtgatttctcgtgagattgtcgct
ttactgcgatgaagcttctgtgcaatcacggtcgcggtgtcaccagcagcctgaagggcctgaa*ttgtag*cacggtcgcta
aaactgagttgtt*ggtaat*gcttgtgggtgttagtctgagagtgggtcatgaagattcctgctttcttgtttagctagcactaaca
agaataggtcttcatggcctttatggtctagtcgtcagggtgttgcacttgaattgtaaactggggttaaaattttacttgag*agg*
*agg*gtaaaatttacgaagatgacagctaaagtggcgagaactgggcatttgttcgcggtcttattgattttgatgagta
tgttaacaggcttagtgacaagtggcagttcagttgtgacagccactgataacattcgcccaacctatcaaaccgat
gctaatggtacctatccgacaaattcgtggcaggtcacgggacaacaaaatgtaatcaatcaacgtggcgggatc
aagtttcagggtgggataataatacaatatggaatggtgatgcgactgataccacgaactcttacctgaaatttggt
gaccccaataatccggattatcagattcgaaaatatgctaaagagacgaatacccctggattgtacgacgtttatttg
aacgtcaaaggcaataaacagcaaaatgtgaagcctgtagatattgtcttagttgttgatatgtctgggtcaatgga
gtcaaacagatggggcacgaatcgagctggtgctgttcgtactggcgttaagaattcttgacttctattcaaaacgc
cggtctgggtaattacgtcaatgttggtttaattgggttttctagtcctggttatatcggtggcaaatcgggttatattag
tgtcaaattaggcaaagcaggtaatgccagccagcaacaagcgattaatggtgcattgagtccaaggtttcaaggg
ggtacgtatacgcagattggtttgcggcaaggatcagccatgctgaatgcggacaccagtggcaataaaaaaatg
atgattttgttaactgatggcgtgccgactttttctaacgaggtgataaattcagagtggataaatggtacattgtatg
gcactaattttggatccagcagagatgaaccagggaacaccgcacgacttcgatggccatacaccgatagttcagg
tcattatatatatgatacttggccagcaacattgggtgaggccaagatagcaaaggatagtggtaatgaggtgcac
gcgttaggcatccaactggctgacgacgaccactacatgacgaaagaaaaaaatacgccaaaacatgcagcttatt
accaattcaccggatttatacgaagatgctgatagtgccgatgctgttgaggcttatttgaacaatcaggcaaagga
cattatcaaaaactttaatactgtcaccgacggcacgatcacagacccgattggtacgcaatttcaatatgcgaaca
accaggcgaccgttacgagtgtcggcaagcaaactgtgccagcaagtgagttgccaagtgcggcgatccaagatg
gtcaattgacggtgaatcacatgaacttgggtcaggatcaggaagttcaaatccattatcaagtacggatcaaaac
agaggatgctggcttcaagcctgattttggtaccaaatgaatggtgaaacattgttgacaccaaaagcgggcgctg
ccgctgttgactttgggattccttcaggcagggcaccagcaactacagtttatgtgcagaagcaatggcgccagtta
agcaatcaatcgttaccggatacgctcaacgtcacggtgcagcgaaaagtggctgacggttcgcttgatccaaattg
gcaacagaccttagtcctaaaaaagctgataactggaaagctagctttacggcacctgcgtataacaatcagggt
caaagttttttcatatgtcgttaagagtgaagatgcctcgggaatttgatttgagttcgtttatcagttctcaaaatatgga
tcagcaaacagcaacgttgactttgacaaatcagcagtatggttttcagtttcagaaaaaaacaaccgatggtactg
atttatcagcagatcagttgaaggccatgcagtttaacttaacccagtacagcgataacagttttcagcaggcatcc
aaaaccaacgccatcacgtcaacggatctgcaggcactagcgccagggtattacggtattcaggaagctgcagca
cctacaggttatcaacttgatgggacaacgtatcttttttcagctaacgtctgatgggcaatggcaataccatggcaca
aaggacaatgtgacatcagggagtgttattaatggccagcagactttgaatcctgttggtgataagtcagatgatttt
acggtgaccggggatcaccagcaaattctgacgctaacgaaatatgatgaaccaaagccatccatgactttgcggg
tcatcaaacaggataatcaaagccaatatcttgcaggtgcagcgttcaccctgcaaccaagtgctggcgaagctga
gacgataacatcatcggcgacatctgagggacaagcgtttgcgacaaaattagttgcagatggtacctatacgatg
tcagaaacaaaagcaccagatggctatcaaagcaatcctgcaaagattgccattcaggtagctacgactggtaaa
gaggcaaccgtcacgattgacggtgaggcattgaagccgggcgaaagtaagaacggatacacattagcgattgat
ggcagcacgatcactttgcaggcgattaatcagccacttgcaattttgccgcatacaggtggtcagggctatcagcg
attgcttggtatcgcactgggattgatcagcgcagcgttccttttattactggttgttttgataaagcgacgggtggtga
agcaacatgactaaatccttccgtccgttagtgattttgaccttttgcttggcactactagtcagtttggcaacgacaa

Figure 7a

```
cgttgcagcagacacaggcggcaactgtgccgaccactgttgatgttgtgttgcataagctgttgtttaaagatacct
tgccaactcaacaagcaaataacgggacaacaaaacccgacttttcgcaggcagatgtgccgttaaacggtgtga
cgttcacagtttatgacgtgaccgctgacttttggcagcttgtctccaaaaatggcggtgcgattgaggtagcacaaa
cgacgttgagtcaagatagctatcagcctgctagctccagccttatcgcacaggttgtgacggctggtcagggagaa
gcgtactttggcgatttaccactccgacaggggcagcatgctgcggtttatcttttaaagaaacggcggcacctaag
aatattgaagccagtcagaatcttgtggttgtcatgtcaagcaaccttcaacatgggaatcaatcacgcattgattta
tttcctaagaacaaaatggtaagtcgtcacaccgatgcccccaaaaaagttccaaagaaaatacgtcaattgttgcc
acaaacgggtgatacagttgcagcttggctttcagtgctcgggttgataatcttcgcgacagtacttgcttttaacata
aaaaaccaaaaaattaataagtgggagagataagaatgaaaaagacaattgccaagaaagtgctgacattaacc
agcacgatcctaatgacattactgatggttctcgggtttaatggcactcgggttcaagcagatacgaatgatacgac
aacacaaaacgttgtccttactaaatacgggtttgacaaagatgttactgccattgatcgtgcgactgatcaaatttg
gaccggcgatggtgctaagcctttacaaggcgttgatttcaccatttacaacgtgacagccaattattgggcatcgcc
taaggattataaaggcagttttgatagtgctccggttgccgcaaccggtacgactaatgacaaggggcaactaacc
caagcattacctatccaatcaaaagatgccagtggtaagactcgtgctgctgtctatcttttccatgaaaccaatccg
cgagctggttataacacgtctgccgatttctggttaaccttaccagccaaggcagcagccgacgggaatgtctatgt
ctacccaaagaatgttcaaaagaccacctatgagcgcacttttgttaagaaagatgctgagactaaagaagtgctt
gaaggagccggctttaagattagcaatagtgatggcaagttttttgaagttgacagataaagatggtcaaagcgtca
gcatcggcgaaggatttatcgatgtattggccaataactatcgattgacgtgggttgctgaaagcgatgctactgtttt
cacgtctgataagagcggtaagtttggcttaaatggatttgctgataacaccacaacttacacggcagttgaaacaa
acgtgccggatggttatgatgctgctgccaatacagactttaaagctgataattcgtctagcgacattctagatgcac
caagcggtattctgccacacactggtggtactggcacagtcattttttgcgatttttgggcgttgccttaattgcatttgga
gcagttgcctatcgcaagcgccgcaatggtttctaaaaagttaataagataaatgagtcaagcaagagcgtcgatggcg
ctcttgttttgatatggcgaggtaatcagagtgacaaaacgaacacgtcgacctttagacttgattgatattgtgattgga
tgtcttcttttagcgggttttggtgttttatgctatccatttgcaagtgatgcttacgtttcttaccaaaatcagcaagtca
tcgacaggtatcgacaacaagaagcgcggaagaatcagatggtgttgcggcgggaatataacgactatcagcaa
aaaaataaacagttggcagcaagtcaacaagtgcccggcgttgccagttttaatcatgctgttaatgatcaaggaa
ccgcaaaaacagcagccaaacgcaatcaacaaatcttgactcggcagacagttgctcagttgacgattcccaaaat
tggccttagtctgccggttttgatcatacaagcgattggcttctacaatttggcgcctgtttattggatggtacaagtt
atccaactggtggtaaaaatacccatgctgtcatttcagcgcatcgtggtgtgccaaacgctgaacttttacccgag
taccagcgttaaaaaaaggcgacaagtttttttattagcataggcaatcataaattggcttaccaagtctttaagcgcc
aggttattgagccaagtgatacccggcagctaagaattgtgccgggacaggatcttgtgaccttaatgacctgcacg
ccttatatgatcaattctcatcgattgttgataacgggtcgccgaattccttacgttaaggcagatgaagaggcttcaa
gttgggcggtttggtggaacaaattaaagctaatagtcgcacttttaggcgcggtgatcattttaggcgtgatcggttt
cgtaatgcgcagtttgatgcttggccgaaagcattatttgctggaagtaccggctgaagccacacaagtcgtggtga
aacgaggtcgacatatacattcttttaaatcagatcaaactggggtgactgacatcagcctgcctggtaatcattatc
gagtcgcaattgtcacaccgcttggccggactaagtacaaggcttatgtcaaaaaaattcgggataaaagctttcaa
ttaaaagaatatcattaagatcttaaaatttgtttaatatccttttgggttaatttaaatgaggaaaggatcaatattttaagactg
atattgagtttaataaactaaaaacgaccaacttattaaaacactatgtctgtatatttcaagcttttgaagtaggacgatgcaac
atgaatgagtattagaaaaccggttcatcaaagatgactttccatagtggaagccgtcttttttgatattaa
```

Figure 7a (continued)

GG02369-GG02372_coding_strand
gcccatggtactgccgagttcactgttgacggggcgcagttgcgtattcatattgagatgtttgatacacctgcaaacgtcca
gcattgggaacacttccatggttttccggatggcaagccagctgagatagccaccgcggcccaagatgctaatggtgacg
gctttgttgatttacctgaaacggaaccggtttccggtacaacgatggtcccgtttgatgccgagcctgctaaaatgcacgta
cccaatgacagctatccagtagccgatgctgacgggcactatgcttatgacaagctcgtggatttaaaagagctgcagaag
gcgttcaaggcagcatttggtagtgaagatttgcaattagataaacgggttgtttacattcatggtgttccggacagtttggaac
ttccagatacggttaaaggaaccgtcatgaactatgatgcacacgtcacactgccaattgccgtgggtaaaattgtccgcgct
tagtagcaaaatataatttaataacgtaggttgttcccgatccgtctgagcgttccagcttagtcaggtcgggatttttgtgcg
ccaaatcctaaaacttataaatactggaatgatcattcatatattcgctgctaattataatttaagaagtaatataccgaagaaaa
ctttatttataaaataacaattattatagttccgtttacgcagttcatcttgttacgcttaattcagcaacaagtgaaaaatgtaacat
gaaaggaggcacccgattgcctaggaaatggattcatatgctgatgttactgctgatgctggtcacgcaaattggca
gtgccgcggtcccggtagccaaaagcgctcagactaatccaaagcacgatgtccgggatgcgtcagtgcagccga
gcactcgtcctgccgcatccgaagctgctgagtttgatctggaagcagcggctagtgcgccatcaaccagcgcggc
cgccaagcaaactacttcaaaagctcggcagcacatcaagctagaagcagggaagtcttggcacggcgatggtca
tacgttaacttacaacgttgacattcagcggtctgaaattcaggttaagttgattttagccaagccacaggatcaaac
ggggcagcaagtcgtcaagttcgctaatgcccaaggattcacgtcccagcctgcacatactaacggtgaaataacg
cgccggcttgcagagaaaacggcagaaaaaggtgaatacctttaaccaaaaagctgcctgatacaaagcagca
agcagctagtgtgaaactcagtctggatggatttaatgacgctgctcaggtattagcgcttgatgttgacttgcagct
gcctgcgcgcctggctaacgatgatgtgcaggaaccggctgcactcagcaaagatgcgcacagtctgattttaccg
ccgtctgcacttgggacgattaaaaattcacgcaactaaagctgatggcgccgcactttcggatgaagaggcgcaaa
tttatcgcaaaccaaatagtagtacccgttcaaaatacggatcacgttgggcgatggagaatggcgtttcatcagat
tatgtgtcgcgttctgatgccaccgccattatttttaaagatgcggttcaaaatcccagtggtccttctaacctgctaga
tgccaagatcaaagtggatattgatcatgttggctcagcaagtgatcttgatggaaaccgttttgagattggtgcttat
gttgaactaacaggtattcgcgtccgtccagtcgaatgggcactaccccctcaggatgtcggcattgattttttccaac
aacttcttttccgggatgtcatttgccaatgttttgtactatgactggcgcgcgtgatttttatgacaaggcaacgagaca
gcgattgaactttattccgcaaagtgaagccaatcaaaattcgaccctgacgtttacttcgttgaatcccggtgagttt
gtctggacggagcaggcggggatgacgcccacttatgacgatcggtttatcacggattggcaatttgaggaaggaa
cctggattacctcagataaagcgacattcgaaaccgaaaaactgggcgctcgcgggaaggaacaacgtgggtac
acctcacagacctggggaaactgggtcgatccaattgatcacgagaatatgacggaatgggaagatcgactaggt
gcgccaacatttgggcgtggtgccgttgcgtttactttaaacggtaccagtcatacctttagacgcggcacttattcca
acggcggcggtacttgggttgccaatgggagtggacaaatcgagttgattgacccaaatgtcaccaacaacaaaa
gcgtgagcgcaaatgccgaagccggtggcggagccgaggaagataaaaccggcaccatctggaccgcaaatgat
ttagacgatcaggtggtcaatcagcattacaacggcgagccatttactactacatcaaccaggaagtatacagtat
gggcgattacgtggtgaagccgaccaaaattgttgtgacggacctgctaccggagcatgtcgagttgattccggac
aataacaacagtcccccgacttatcaaaaagcgttccagctctttaatgcaactgatccggatgcggttggccaaga
tcggaaaatgacgctgactgaggacgtgtcggattttgtcgtgacgcaagaaggcgatcggcagcgaatcacgctg
acaatcggacgtgaagatgtgcagaaaattcattttcatagcggcttttctcacttcgattgaaggtgcggccaaca
aaggatccggacaccctgacaaaacgacttacgctggtcaataaagcgaccgttaaattttcgacactgaggaac
gttacagtaaggaaaccaacgcagtgcaggttcatcttgatccggcaggcagatttccagctgaatttaccaagaa
aaaccagtatggcgcagtgctgccgggtagtcggtttgtcttgaagcaaggagacactcaactgcaaacagcaact
gccgattcgcagggtaaagtctcatttggaacgctaaaaccgcgcgactatcaggtaagcgaaattgccgctgccg
gtcacgagttgcaggctgaatttgatttaaaagtggcagctgacggtactgtgacagtcggccgcaacggcgagat
ttggccagacaccacggtgatcaaccaactgaaacccaccgaacttgagttgatcaaaattgaaaaaggtaaaaa
caaactcgccaatgcaagttttgccttataccgtggcgatcaaaccaccccctgttgctcaaggaacgactgatgaaa
atggccagttgcgattcacacatcagttgaccccgggaacttatcgcttaacggaaaccaaagcgcctgccggattt
gatcggctgaacggatcgtttaccttcaagattaacgcgcatggcacaatggtagatcttgcgtatagtggcagcga
tttaagcagtgatgagtatgggtttgaatttatccctgatgcagaggataagttgaatcggattcgcttcacactgac
gaaccattcgttggaaacactcctaccgaaaactggtggtagcggtatcttgctgtttctcatggtcgcaatcagtgc
gtgtggcggcggctggctgctttacctgtatctgaagcgaaaggaggcccgttaagatgcgacgatttattggtgg
cttgtcccgttgcttctattgattggtatcgtgcttggcaacacaccacattgggttcacgcggctgatcaaactgccg agattgtgatccataagcgaatttatcgggatattcgccaaccggaagacgtttggtatgaaaatgacggtcatcgg
attgacccgaataacccggataaagatggctacaaattattaagcaaaaccagcgggctgaatggtgctaactttg
aggtctatgatgccagctccttattgaaaccgaatatgacgcctgaagcaattcgggctttagttgatcgttatcaga
atatgacgcgtaagcaagcactgaaatttgcgcgggccaacctgaaattagccggtcaagggaacaaaggtatcg
ggctgatgaatacaaaaaacgatccaacactcggtgaagatgggatcagccgaataaccgtttctgtcgatcaaca
ggcaccgactaaagcttatctgatgatcgaggtggcaccggatccttcaaccgaactcaatgtggacttagagcgc
aaaagttcgccgatgttagttgtttttccagtcacggatcctatcagtggcaacccgttacagaccatccatctgtatc
cgaaaaatgtcggttatgtccgcgatccgtatttcttcaagttcggcgtgcaccctgatggtacgagtaaacggttag
ccggtgcgatctttgctatttaccgaattgagaatggtaagaagctttatctcgatatgtcgccagtaaccgacttgcg
caacaaatgggtgagcactactgatccgttgcatgatgaccgcgtgaacaaatttgtttccgatcaagatgggctag
ttaatacaggtgaacgcttttgcccgccggagaatatttctttgaagaattgcaaggcgttcccggctatgaagtgg
atgctaaaagccgcgcgatcaaaatcgagattcctgattcttgggaagacgaagatggcaaccggcgctttgtgtta
attgacggccagccgatgcaggaaaactttggcggggtggtgacaccggaaatgatcagtagcggctaccgcga
gtttataactatgccgataagcaggcgtcgacaaccggtgatcaaaccgcggggccatcaacgacccagcttggca
atcacgggcaggatacgaacggcaccggaacgcgtacacctaagcgtcaatccggttatttgccggccatgtccga
ttggcgcaatttacgctttgtcctttaggagtctgttactactactggccacttacttcttcattaaaaataagaaag
cgaggcaccacgcatgcaagtaacgtttaaaaagatcgggcacagtctcttggcagcgctgatgctcatgagcttc
cttctaccactgcttagtgcgggcaaacccgtacatgccgcgacaacgactgtggatttcacgctgcacaaaatcga
acaaaccagtgacgaacagattcaaaataccggccacgaccttggactgaccgggcgtaaaccggtgcaaggcg
ctcaatttaaaattttcaacgtgacggacgccttttaccaattactggaaaatcatgataagacaaccgctgcgagc
atgatatcgcaaaacctgggtcagtatgtgaatctccaggatcctaatgcagcaactgtcacgactgatgcagacg
gcttggcggcattcaaaggattagccgccaaaaccaatggccggcatagcgtgtacgcatttcacgaagccgtgac
cccgcaaccgtatcaaaaagcagcagatatgatcgtgagtctgccagtgcggcaagacgatggatcggatctgac
caacattcatctttatcctaaagacagtcttgttaccaaaaatctgacggaaatcaatgaacaagcggtggcaacaa
aagatctccatgatgtcgcggttggcgatgtgctcacgtatcaggttcagttccagattccgcatgatattggcgcgct
ggctgatcacagtcaagacactttttaagtacaaccaatttaaagtgctggattatatgaccaaggaaggccttactt
taaggcattgacggcaatcacggttgacggtcaggacattttaaaggcattaaccggaaaaatggccttcatgagtt
ctaatgacgcagcttggcaacaaacacacaactatccattcgggtttgaactggactttctaggcgggaccgatccc
gatgcggtacgaaacctgttgacccaatatgccggcaaacgcgtgaccgttgcctacaccggaatcgtcaatgaga
aaatgatcccagaccaaaaagtcggtaacacggctgaagtgagctttgatcctgacagcaagattaccgtcaatgg
tccggaaatccagactggcgggattcggttcttcaaacacgaagccggatcttccaaaagtttggccaacgcgactt
tcatcttacagcgaatgaacggcaatgtgcgcgaatatgcagttcttgaaggcgttaacggtatggccggaacctac
caaccgaccaagattacctggacaacgaatcaagacgcggcaacgagactcaaaaccagtggagccgagacag
ccaacttaaccattcaagggctgttgccagggcgatataccttggttgaaaccgcggcaccagaaggctatgaaat
ccttgatccgacaacagattttgaagtcattgccggtacttgggggtacgaaaacgattcgcatcgccaacacgccgg
tgaatcaattattgccgatgacaggcggaatcggactcttcgccttcctgatgatcggggccatcttaatgggtggcg
gtcacctaatgaagaaaaagaccagcaagaaagtctaatggcctatgacaaaaaaagcgtcggggacaagtcgg
ctgttacgctggttcgtcatcttacttttactgcgggagccgcgtgtttctgctatccgttcgcggcaacggctattaat
gaattgctactaaccagtcgccgagcagcagcacagcaagaagccaagcaaaatgccgccgcccaagatgagca
acgggcagcggagaaccgtgcacttgcccagactggttttgcgtccgggacaggatccgtttcaaagtaggcagaa
atttaaccaagcctatgtgaaacggcatctgatcgggcgagtggttatcccgaaattagccggttgatctgccccttttt
gacaccaccaacaacacgctgttagatcaaggggcagtggtgttaccaggtactagctatccgcggggaggcaag
aacacgcatacagttgtttcggcacacggcggcttgcccaccaaacgcttttcaccgatctgagcaagttgaaacg
agggcagaagttcttctccaagtcaacggcaaaaagatggcgtatcaggtctttcggatcaaaaccgtgcggccg
gatgaaacccagagcttgcgcattgaaccgggacgcgatttggccacattaatgacctgtaccccgtatatgatcaa
ctcccaccgcctgttagtgaccggcaaacgggtaccttataccgaatcacttgagcacgccgccgagtctgctgatc
gctggcgcttgtggttaagtatcgcggttgtcgtcggagtgctgggattggcattgctgagtttctatctggctcggcg
ctatcttcgccgaccgcgggcgtaatctggaaagagaatgttagaaagtaagaaagttcgccgttgtcaggataggtc
tgtggacggcgggctttttgtgtttcga

PEPTIDES AND METHODS FOR PRODUCING THEM

FIELD OF THE INVENTION

The present invention relates to the fields of life sciences and food, feed or pharmaceutical industry. Specifically, the invention relates to novel peptides, proteins, pilus structures, polynucleotides as well as vectors, host cells, products and pharmaceutical compositions comprising the polynucleotides, peptides, proteins or pilus structures. The invention also relates to gene clusters and antibodies. Furthermore, the present invention relates to methods for producing the peptides proteins or pilus structures or producing the products comprising the peptides proteins or pilus structures. Furthermore, the present invention relates to treatments as well as uses and methods for screening of bacterial strains, for reducing or inhibiting the adhesion of pathogenic bacteria, promoting the adhesion of bacterial cells to the mucus and/or epithelium and/or for modifying immune response in a subject. Still, the present invention relates to methods for detecting probiotic bacterial strains or pathogen strains to be identified and/or inhibited.

BACKGROUND OF THE INVENTION

Invasive adherence to host tissues by bacterial pathogens is often facilitated by means of elongated hairlike proteinaceous fibers called pili or fimbriae that protrude outwardly from the microbial cell surface. In Gram-negative pathogenic bacteria the role of pili as colonization agents in pathogenesis is well recognized and the overall mechanism of pilus assembly is clearly defined from over fifty years of research. The most structurally characterized Gram-negative pili are the type I form, found, for example, in the enteropathogenic *E. coli*, and type IV form, found, for example, in species of *Neisseria* and *Pseudomonas* as well as in *E. coli*. Typically, the Gram-negative pili are long (1 to 4 µm in length) and thin (5 to 8 nm in width), and also display both flexible and robust structural properties. These pili are generally comprised of a series of non-covalently linked multiple protein subunits whose assembly is dependent upon specific chaperone proteins, but independent of any enzymatic activity. Frequently, a protein with adhesive properties is positioned at the tip of the pili. It is generally considered that the intervening length of protein subunits from the microbial surface promotes an unhindered contact between the adhesive tip protein and corresponding host cell receptor sites, which are potentially represented by components of the extracellular matrix (ECM) or specific carbohydrate moieties of glycoproteins and glycolipids (Scott J. R. and Zähner D, 2006, Mol Microbiol 62, 320-330; Telford, J. L., et al. 2006, Nat Rev Microbiol 4, 509-519).

The presence of Gram-positive pilus-like structures was actually first observed in the late 1960's by electron microscopy of *Corynebacterium renale* (Yanagawa, R. et al. 1968, Jpn J Vet Res 16, 31-37), and in the subsequent years pili have been found in several other Gram-positive bacterial species, including the very recent discovery of pili in the three main invasive disease-causing streptococcal pathogens in humans, i.e., *Streptococcus pyogenes, Streptococcus agalactiae*, and *Streptococcus pneumoniae* (Telford, J. L., et al. 2006, Nat Rev Microbiol 4, 509-519). The most detailed characterization studies of Gram-positive pili originate from the corynebacteria, streptococci, and bacilli pathogens.

Unlike in the Gram-negative bacteria, the pili in Gram-positive bacteria are much thinner in width (2 to 3 nm) and more difficult to visibly distinguish which also suggests why the presence of these pili may have been over-looked in many species of Gram-positive bacteria (Kang, H. J. et al. 2007, Science 318, 1625-1628). To date, the most thorough description of the pilus-assembly process, that is also generally representative of all Gram-positive pili, has been carried by in vivo characterization studies of pili biogenesis in *Corynebacterium diphtheriae* (Ton-That, H. and Schneewind, O. 2004, Trends Microbiol 12, 228-234). Structurally, the prototype pili appear as polymers composed of covalently cross-linked protein subunits (called pilins) that are also covalently anchored at the base to the peptidoglycan component of the cell wall, with both of these covalent bonds being enzymatically dependent upon catalysis by different sortase family membrane-bound transpeptidases, i.e., the pilin-specific and the housekeeping sortases, respectively (Mandlik, A. et al. 2008, Trends Microbiol 16, 33-40). The Gram-positive pilus is typically composed of three pilin subunits and, in the case of *C. diphtheriae*, the genes named as SpaA (sortase-mediated pilin assembly) for the major pilin subunit that exclusively forms the shaft or backbone of the pilus, SpaB for an ancillary minor pilin subunit, and SpaC for another minor pilin subunit with adhesive properties located at the tip of the pilus (FIG. 1). The genes encoding these three pilin subunits are localized within the same loci as a pilin gene cluster along with at least one gene encoding a pilin-specific sortase in close proximity. As well, the genes within the pilin cluster are frequently flanked on both ends by transposable elements suggesting an origin by horizontal gene transfer. The transcription of all these genes is in the same direction and indicative of operon regulatory control (Scott J. R. and Zähner D, 2006, Mol Microbiol 62, 320-330).

The revised model of the overall Gram-positive pilus assembly process, which is dependent upon several different conserved motifs and domains within the primary sequence of each pilin subunit, includes four basic stages (Mandlik, A. et al. 2008, Proc Natl Acad Sci USA 105, 14147-14152; Telford, J. L., et al. 2006, Nat Rev Microbiol 4, 509-519)-(FIG. 1). In the first stage, the pilin proteins, each of which contain a N-terminal signal peptide, are secreted through the bacterial cell membrane by the Sec-dependent pathway and then retained in the cell membrane by the presence of a C-terminal membrane-spanning domain consisting of a hydrophobic region of about 20 residues and a positively charged tail.

In the second stage of the assembly process, the cell wall sorting signal (CWSS), preferably the LPXTG-motif, which also immediately precedes the membrane-spanning domain, becomes available for sortase-dependent cleavage of the cell membrane-anchored pilin proteins. The pilin-specific sortase cleaves this five residue motif between the threonine (T) and glycine (G) residues and forms an acyl-enzyme intermediate involving a covalent thioester bond between the carboxyl group of the threonine residue and a cysteinyl thiol found within the catalytic pocket of the sortase.

The third stage represents the polymerization of the pilin subunits by isopeptide bond formation and involves the cleavage of the thioester bond and the release of the sortase from the pilin subunit by the nucleophilic attack of the ε-amino group from the side chain of a lysine (K) residue conserved in the pilin-motif (WXXXVXVYPKN) of a second pilin subunit. An amide bond is thought to form between the C-terminal carboxyl of the threonine residue in the first pilin subunit and the side chain amino group of the pilin-motif lysine from a second pilin subunit still bound as a covalent thioester with an another pilin-specific sortase (Budzik, J. M. et al. 2008, Proc Natl Acad Sci USA 105, 10215-10220). In this model of pilus assembly, the growing polymeric structure is fed by additional pilin subunits at the base of the pilus and the overall length governed by the amount of available pilin subunits associated with pilin-specific sortases. Since the pilin-motif is a characteristic feature of the major (SpaA) and ancillary minor (SpaB) pilin subunits, but missing in the primary sequence of the minor pilin subunits (SpaC) displaying adhesive properties, this pilin subunit is likely located at the tip of the pilus shaft and the first pilin subunit to initiate pilus polymerization.

The attachment of the polymerized pilus to the cell wall represents the fourth stage of the assembly process. Herein, the ancillary minor pilin subunit (SpaB) signals the cessation of pilus polymerization, but only when presented in association with a housekeeping sortase, whose gene is encoded somewhere else on the genome. In this final stage, the growing polymeric structure of major pilin subunits (SpaA) is transferred from a thioester linkage with a pilin-specific sortase to form an amide bond with the side chain of the lysine in the pilin-motif of SpaB minor pilin subunit, which is coupled as a housekeeping sortase acyl-enzyme intermediate. The nucleophilic attack by the amino group of the pentapeptide of the peptidoglycan lipid II precursor then permits the housekeeping sortase to catalyze the attachment of the SpaB pilin-linked pilus polymer to the cell wall. The E-box represents a third and less characterized conserved primary sequence motif (YXLXETXAPXGY) found between the LPXTG- and pilin-motifs of the pilin subunits from many Gram-positive bacteria.

Thus far, three-dimensional (3-D) structure determinations by x-ray crystallography have revealed structural insights into the assembly and function for only two Gram-positive pilin subunit proteins. Krishnan et al. (2007, Structure 15:893-903) had solved the crystal structure for the minor pilin GBS52 of *Streptococcus agalactiae* and revealed the presence of two IgG-like domain folds that share a structural similarity with the *S. aureus* collagen-binding protein Cna which also indicates how this minor pilin subunit could facilitate pilus adherence to a specific host tissue. The crystal structure of the major pilin Spy0128 from *Streptococcus pyogenes*, solved by Kang et al. (2007, Science 318, 1625-1628), had demonstrated how self-generated intramolecular isopeptide bonds between the side chains of lysine and asparagine residues within the pilin subunit could also complement the sortase-catalyzed intermolecular isopeptide bonds for maintaining the overall strength and stability of pili.

The majority of probiotic microbes are members of the Gram-positive lactobacilli and bifidobacteria and have a long tradition of use in fermented foods and dairy products (Goldin, B. R. and Gorbach, S. L. 2008, Clin Infect Dis 46, S96-S100; Ljungh, A. and Wadstrom, T. 2006, Curr Issues Intest Microbiol 7, 73-89; Salminen, S. et al. 1998, Br J Nutr 80, S147-S171). Pilus structures of probiotic lactobacilli or genes encoding these pilus structures have not been described in the literature. The presence of pilus-like structures or polynucleotides has never been shown in *Lactobacillus rhamnosus*.

BRIEF DESCRIPTION OF THE INVENTION

The object of the present invention is to provide novel pilus polypeptides as well as polynucleotides encoding them. Furthermore, the object of the invention is to provide novel pilus structures. Still, the object of the invention is to provide novel methods, uses and products related to the above-mentioned peptides, polypeptides, proteins, pilus structures, and polynucleotides.

The present invention relates to peptides comprising a sequence having at least 94% sequence identity with seq id no 1 (GG00441), at least 94% sequence identity with seq id no 2 (GG00442), at least 84% sequence identity with seq id no 3 (GG00443), at least 91% sequence identity with seq id no 4 (GG00444), at least 83% sequence identity with seq id no 5 (GG02369), at least 94% sequence identity with seq id no 6 (GG02370), at least 93% sequence identity with seq id no 7 (GG02371) or at least 93% sequence identity with seq id no 8 (GG02372), or fragments or variants thereof.

The present invention also relates to a pilus structure comprising at least one of the peptides of the invention, a product comprising at least one peptide or pilus structure of the invention and to a pharmaceutical or nutritional composition comprising at least one peptide or pilus structure of the invention.

Furthermore, the present invention relates to a product comprising at least one peptide or pilus structure of the invention for use as a medicament or for the prevention or treatment of diarrhea, arterial hypertension, vascular diseases, allergies, cancer, atopic diseases, viral diseases, infectious diseases, urinary tract infections, respiratory infections, dental caries, irritable bowel syndrome (IBS), inflammatory bowel disease (IBD), mucosal inflammation, gut permeability disorders, obesity, metabolic syndrome, oxidative stress or abdominal pain.

Furthermore, the present invention relates to the use of at least one peptide or pilus structure of the invention in the manufacture of a medicament for treating or preventing diarrhea, arterial hypertension, vascular diseases, allergies, cancer, atopic diseases, viral diseases, infectious diseases, urinary tract infections, respiratory-infections, dental caries, IBS, IBD, mucosal inflammation, gut permeability disorders, obesity, metabolic syndrome, oxidative stress or abdominal pain.

Still, the present invention relates to a polynucleotide comprising a sequence of any one of seq id nos 9-16 or a degenerate thereof, or encoding a peptide of the invention, to a vector comprising the polynucleotide of the invention, to a host cell comprising the polynucleotide or the peptide of the invention, and to a gene cluster comprising at least one polynucleotide of the invention.

Also, the present invention relates to an antibody/antibodies against the peptides of the invention or their functional domains.

The present invention also relates to a method of treating or preventing diarrhea, arterial hypertension, vascular diseases, allergies, cancer, atopic diseases, viral diseases, infectious diseases, urinary tract infections, respiratory infections, dental caries, IBS, IBD, mucosal inflammation, gut permeability disorders, obesity, metabolic syndrome, oxidative stress or abdominal pain comprising administration of at least one peptide or pilus structure of the invention to a subject.

The present invention relates to a method for screening of bacterial strains, which comprise at least one polynucleotide of the invention or a fragment thereof, wherein the method comprises:

i) providing DNA or RNA from bacterial strains;

ii) hybridizing primers or probes specific to the polynucleotide of the invention or a fragment thereof with DNA or RNA from step i) and optionally amplifying the polynucleotide or the fragment thereof;

iii) detecting at least one polynucleotide or a fragment thereof homologous to the polynucleotide of the invention or the fragment thereof.

The present invention relates to a use of at least one polynucleotide of the invention or fragment thereof or at least one antibody of the invention for screening of bacterial strains.

The present invention relates to a method of screening bacterial strains, which comprise at least one peptide or pilus structure of the invention, using at least one antibody of the invention, wherein the method comprises:
  i) providing proteins of bacterial strains;
  ii) detecting at least one polypeptide, pilus structure or a fragment thereof using the antibody/antibodies.

The present invention relates to a method of reducing or inhibiting the adhesion of pathogenic bacteria to the gastrointestinal tract, to the epithelium or to the mucus of a subject, wherein the method comprises administering at least one peptide and/or pilus structure of the invention to the subject.

The present invention relates to a use of at least one peptide and/or pilus structure of the invention for reducing or inhibiting the adhesion of pathogenic bacteria to the gastrointestinal tract, to the epithelium or to the mucus of a subject.

The present invention relates to a method of promoting the adhesion of a bacterial cell or the adhesion of any other agent to the mucus or epithelium, wherein the method comprises:
  i) producing at least one peptide or pilus structure of the invention or a fragment thereof;
  ii) displaying the peptide, pilus structure and/or fragment thereof on the bacterial cell or on any other agent;
  iii) bringing the bacterial cells or any other agent into contact with the mucus or epithelium.

The present invention relates to a use of at least one peptide or pilus structure of the invention for promoting the adhesion of a bacterial cells or the adhesion of any other agent to the mucus or epithelium.

The present invention relates to a method of modifying immune response in a subject, wherein the methods comprise:
  i) producing at least one peptide or pilus structure of the invention or a fragment thereof;
  ii) displaying the peptide, pilus structure and/or fragment thereof on a host cell;
  iii) optionally bringing the host cell into contact with the mucus or another host cell.

The present invention relates to a use of at least one peptide or pilus structure of the invention for modifying immune response.

The present invention relates to a method of producing a product of the invention, wherein the method comprises a step of generating at least one peptide or pilus structure of the invention to a product.

The present invention also relates to a method of producing at least one peptide or pilus structure of the invention, wherein the method comprises the following steps:
  i) providing at least one polynucleotide of the invention;
  ii) transforming a host cell with the polynucleotide(s);
  iii) culturing the host cell from step ii) to produce the peptide(s) or pilus structure;
  iv) optionally recovering the peptide(s) or pilus structure.

In addition, the present invention relates to a method of producing at least one peptide or pilus structure of the invention, wherein the method comprises the following steps:
  i) disrupting a cell producing or comprising at least one peptide or pilus structure of the invention;
  ii) optionally, recovering the peptide(s) or pilus structure.

Also, the present invention relates to a method of producing at least one peptide of the invention, wherein the method comprises the following steps:
  i) providing amino acids;
  ii) manufacturing at least one peptide of the invention from the amino acids of step i) with synthetizing at least one peptide.

The present invention relates to a method of detecting potential probiotic bacterial strains by using bioinformatic approaches, wherein the method comprises the following steps:
  i) providing a sequence of at least one peptide, polynucleotide or fragment thereof;
  ii) comparing the sequence of step i) against sequences of sequence collections;
  iii) detecting sequences having biologically congruent fragments to sequences of step i) or having high identity to the sequence of step i).

The present invention also relates to a method of detecting pathogen strains, against which the peptides or pilus structures of the invention are effective, by using bioinformatic approaches, wherein the method comprises:
  i) providing a sequence of at least one peptide, polynucleotide of fragment thereof;
  ii) comparing the sequence of step i) against sequences of sequence collections;
  iii) detecting sequences having biologically congruent fragments to the sequence of step I) or having high identity to the sequence of step i).

The peptides, pilus structures and polynucleotides of the invention provide tools for further developments in food, feed, cosmetics and pharmaceutical industries. The present invention enables rapid and efficient screening methods and reliable and accurate, either qualitative or quantitative analysis of a multitude of bacterial strains. Therefore, the methods and means of the invention enable the discovery of novel probiotic bacterial strains as well as discoveries of new products (incl. ingredients, supplements, and nutritional products), medicaments and therapeutic methods. Furthermore, by the present invention more effective and specific treatments become available.

There is a continued, evident need to offer the consumers new products having clearly demonstrated effects on health and produced in a form that allows them to be used as such or as a part of another product, such as a pharmaceutical or a food or feed product. In accordance with the present invention, products are also applicable as capsules, pills or tablets that allow the use as convenient part or supplement, for example, of the every-day diet or medication.

BRIEF DESCRIPTION OF THE FIGURES

FIGS. 1a and 1b show the models of pilus assembly and covalent attachment to the cell wall in Gram-positive Corynebacteria.

FIG. 6a shows the presence of SpaA-containing pili and SpaA monomers in LGG and FIG. 6b shows the presence of SpaC-containing pili and SpaC monomers in LGG. Lane 1: recombinant SpaA/SpaC pilin protein; Lane 2: LGG grown in mTSB; Lane 3: LGG grown in MRS+0.6% ox gall bile; Lane 4: LC705 grown in mTSB; Lane 5: LC705 grown in MRS+0.6% ox gall bile. The antibody used is indicated on a top of each picture. In FIG. 6b, Panel A: lanes 1 to 5 are exposed for 1 second; Panel B: lanes 2-5 are exposed separately for 60 seconds. The positions of the molecular weight standards are indicated on the left as kilodaltons. HMW indicates high molecular weight ladder.

FIGS. 7a and 7b show nucleotide sequences encoding the pili operons presented in FIG. 2. FIG. 7A shows the operon encoding GG00441-GG00444 genes (bold). The putative conserved elements −35 sequence (underlined), −10 sequence (double underlined), ribosomal binding site (underlined italics) and rho terminator (dotted underline). FIG. 7B shows the operon encoding GG02369-GG02372 genes (bold). The putative conserved elements −35 sequence (underlined), −10 sequence (double underlined), ribosomal binding site (underlined italics) and rho terminator (dotted underline).

DETAILED DESCRIPTION OF THE INVENTION

Lactic acid bacteria have been utilized in food industry for a long time and today they are used in various food supplies such as milk products. For example lactobacilli and bifidobacteria are known to have probiotic effects, but the ways by which probiotic bacteria affect the health are not fully understood. Therefore, further investigations of probiotics are warranted.

This invention resides in the finding that also Gram-positive bacteria has pilus structures. Furthermore, the invention resides in the finding of novel pilus peptides and structures in Gram-positive bacteria, specifically in lactobacilli, more specifically in *Lactobacillus rhamnosus*.

Peptides of the Pilus Structure

Generally a Gram-positive bacterial pilus extends out from the outer membrane of the bacteria, usually being 1-4 µm long and 2-8 nm wide and appearing in low numbers. Pili is considered to promote adherence of the bacteria to target surfaces. Indeed, as used herein, the expression "pilus structure" refers to an elongated hair or hairlike proteinaceous fiber, comprising multiple protein subunits (preferably more than one subunits). The assembly of these proteins may be dependent on specific proteins, i.e. sortases. A protein having adhesive properties is usually located at the top of the pili. Also the other proteins of the heteromeric pilus structure may be adhesive. As used herein, the expression "part of a pilus structure" refers to any component of a pilus, preferably any protein or any fragment or any variant of the pilus. In a preferred embodiment of the invention, the pilus structure is located on the surface of a microorganism or originates therefrom.

As used herein, the expression "peptide" refers to any peptide such as a dipeptide, polypeptide, protein and/or pilin protein.

In a specific embodiment of the invention, characteristic features of the pilin are major (SpaA), ancillary minor (SpaB) and capping (SpaC) pilin subunits.

Figure 1A:
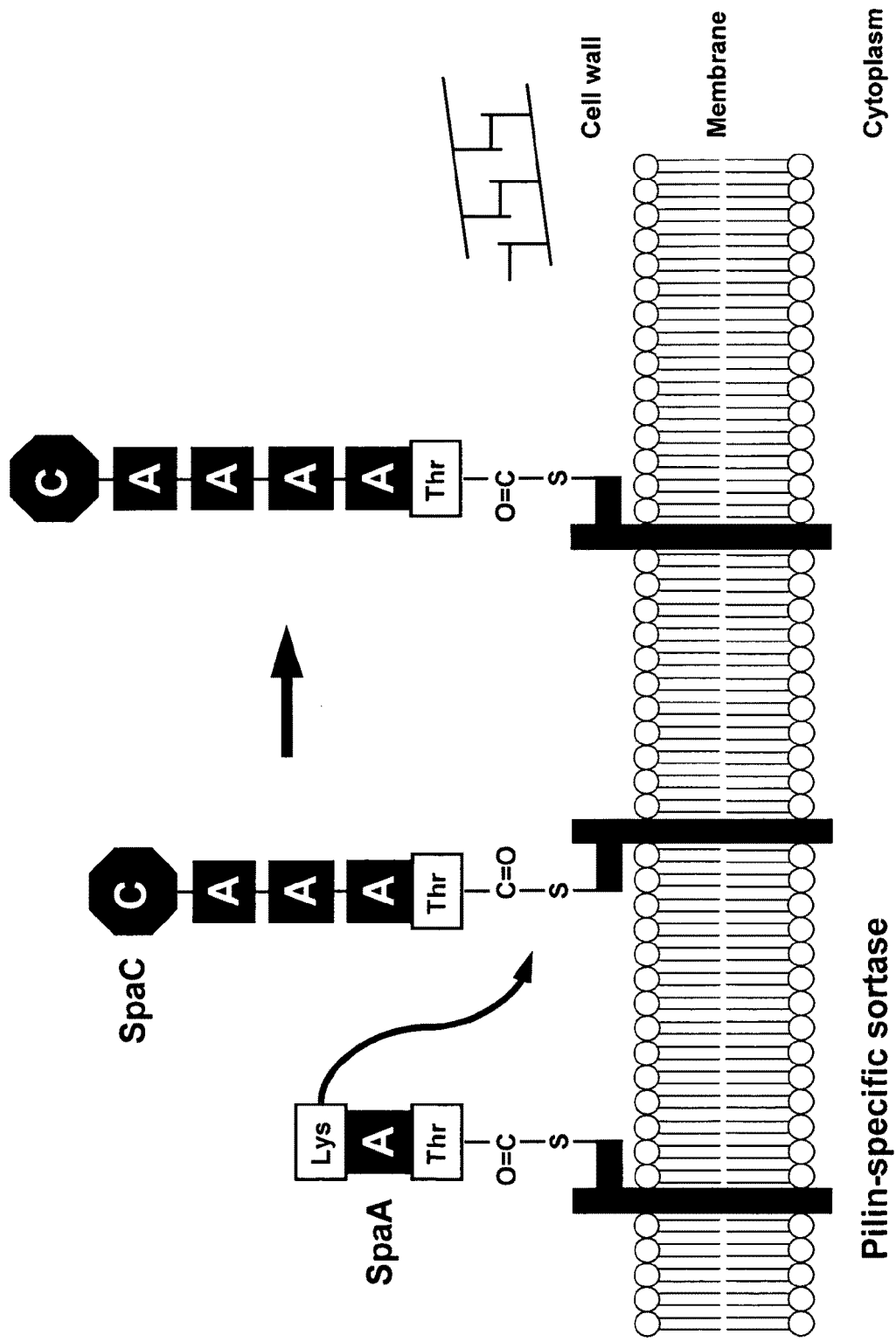
Figure 2:
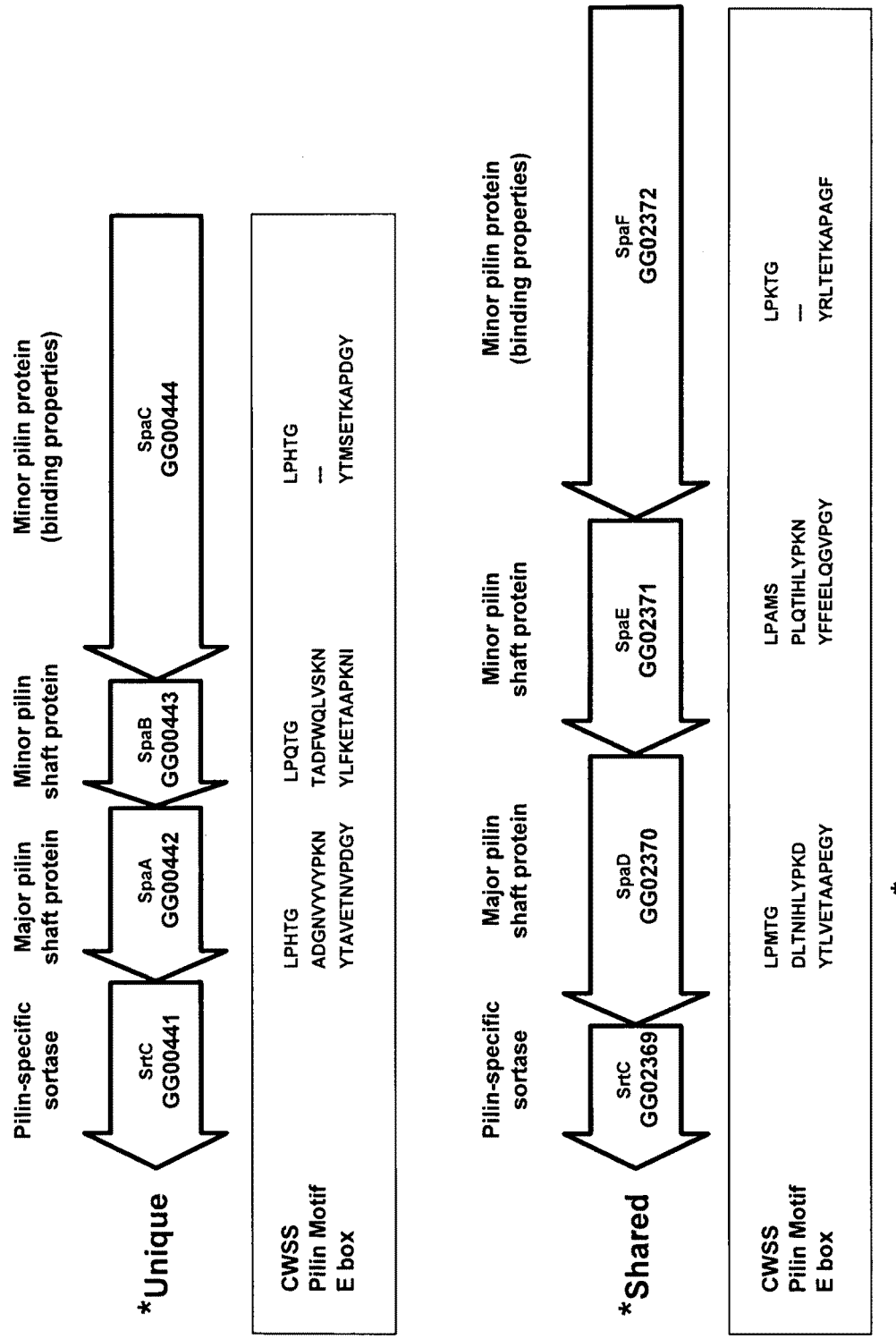
FIG. 2 shows the *Lactobacillus rhamnosus* GG (LGG) pili clusters including genes encoding pilin-specific sortases, major pilus shaft protein, minor pilus shaft protein and capping pilus proteins. CWSS indicates a cell wall sorting signal, i.e. a conserved motif found in many Gram-positive bacteria, Pilin Motif and E-box also indicate conserved motifs found in many Gram-positive bacteria.

Pilin specific sortases act by transferring SpaA to SpaC in a growing polymeric structure of pilin (FIG. 1). In a preferred embodiment of the invention, the peptide comprising a sequence having at least 94% sequence identity with seq id no 1 (GG00441) or a sequence having at least 83% sequence identity with seq id no 5 (GG002369) is a pilin specific sortase (FIG. 2).

SpaA likely forms a back-bone of the pilus structure. The length of the different pilus structures depends on the amount of SpaA in the back-bone (FIG. 1). In a preferred embodiment of the invention, the peptide comprising a sequence having at least 94% sequence identity with seq id no 2 (GG00442) or a sequence having at least 94% sequence identity with seq id no 6 (GG002370) is a major pilus shaft protein, i.e. a major pilin subunit (FIG. 2). GG00442 and GG02370 contain the sortase-recognition site, thus being substrates of the sortases.

SpaB is likely added to the pilus structure at the latest state (terminal stage) of the pilus formation and it forms a link of the pilus to the cell wall (FIG. 1). In a preferred embodiment of the invention, the peptide comprising a sequence having at least 84% sequence identity with seq id no 3 (GG00443) or a sequence having at least 93% sequence identity with seq id no 7 (GG002371) is a minor pilus shaft protein (FIG. 2). GG00443 and GG002371 contain the sortase-recognition site, thus being substrates of the sortases.

SpaC is likely located at the tip of the pilus shaft and the first pilin subunit to initiate pilus polymerization (FIG. 1). In a preferred embodiment of the invention, the peptide comprising a sequence having at least 91% sequence identity with seq id no 4 (GG00444) or a sequence having at least 93% sequence identity with seq id no 8 (GG002372) is a binding pilus protein (FIG. 2). GG00444 protein contains a von Willebrand factor (vWF) domain, and GG00444 and GG02372 contain the sortase-recognition sites, thus being substrates of the sortases.

In a specific embodiment of the invention, the peptide or polypeptide of the invention comprises a sequence having at least 60, 65, 70, 75, 80, 81, 82, 83, 84, 85, 86, 87, 88, 89, 90, 91, 92, 93, 94, 95, 96, 97, 98, 99, 99.5, 99.8, 99.9 or 100% identity to amino acid sequence of Seq ID No. 1, 2, 3, 4, 5, 6, 7 or 8, or fragments or variants thereof.

According to a specific embodiment of the invention, the peptide has at least 60, 65, 70, 75, 80, 81, 82, 83, 84, 85, 86, 87, 88, 89, 90, 91, 92, 93, 94, 95, 96, 97, 98, 99, 99.5, 99.8, 99.9 or 100% identity to any one of the amino acid sequences of Seq ID No. 1, 2, 3, 4, 5, 6, 7 or 8, or fragments or variants thereof.

In another specific embodiment of the invention the peptide has a sequence shown in any one of the sequences Seq ID No 1, 2, 3, 4, 5, 6, 7 or 8, or fragments or variants thereof.

Identity of any sequence or fragments thereof compared to the sequence of this invention refers to the identity of any sequence compared to the entire sequence of the present invention. Sequence identity may be determined for example by using BLAST (Basic Local Alignment Search Tools) or FASTA (FAST-All). In the searches, setting parameters "gap penalties" and "matrix" are typically selected as default.

As used herein, a fragment or variant of a peptide refers to any part or variant of a peptide, which may have the biological function. A variant refers to a peptide having small alterations in the peptide sequence, e.g. small deletions, mutations or insertions.

In a preferred embodiment of the invention, a peptide having seq id no 2-4 or 6-8 is a part of a pilus structure. In another preferred embodiment of the invention, the pilus structure of the invention comprises at least one of the peptides of the invention, more preferably at least two, or at least three peptides of the invention. Furthermore, in a preferred embodiment of the invention, the pilus structure comprises peptides GG00442 (Seq ID No 2), GG00443 (Seq ID No 3) and GG00444 (Seq ID No 4) and/or peptides GG02370 (Seq ID No 6), GG02371 (Seq ID No 7) and GG02372 (Seq ID No 8).

Gram-Positive and Probiotic Bacteria

The peptides or pilus structures of the invention can be from any bacteria, such as Gram-positive or Gram-negative bacteria. However, in a preferred embodiment of the invention, the peptides or pilus structures are from gram-positive bacteria. Gram-positive bacteria, which may comprise the peptides or pilus structures of the invention, include but are not limited to lactobacilli, lactococci, bifidobacteria, propionibacteria, leuconostoc, streptococci corynebacteria, actinomyces and mycobacteria.

In a preferred embodiment of the invention, the peptide or pilus structure is from probiotic bacteria such as probiotic lactobacilli, lactococci, bifidobacteria, enterococci, propionibacteria, leuconostoc, streptococci or yeast. Probiotics are live micro-organisms, preferably non-pathogenic microbes which, when administered in adequate amounts to man or animal, promote the well being of the host (Fuller, R. 1989, J. Appl. Microbiol. 66:365-378). Probiotics will result in a beneficial health advantage to the host, when consumed as a food or a food supplement in adequate amounts.

Health claims of probiotics in humans or animals include the possible prevention and treatment of many ailments. The health-promoting effects of probiotics include for example the balancing and maintenance of intestinal flora, stimulation of the immune system and anti-carcinogenic activity. The useful effects of probiotics in human intestines are based on several independent factors caused by live bacterial cells, their cell structures and metabolic products.

A bacterium may be referred to as a probiotic if it essentially meets the following requirements (Lee, Y-K and Salminen, S. 1995 Trend Food Sci Technol, 6:241-245): it remains viable in the demanding conditions prevailing in the digestive tract (low pH of the stomach, acids of the digestive system, etc.); attaches to the walls of the intestine; colonizes the GIT; metabolizes in the intestine; is technologically applicable (endures processing); exhibits clinically tested and reported health effects; and is safe to consume.

There are huge differences in microbial content between the different parts of the gastrointestinal tract, about 95% of all the intestinal bacteria appearing in the colon. Over 400 bacterial species have been estimated to thrive in the colon in addition to transient microbes. The dominating species are the following: *Bacteroides, Bifidobacterium, Coprococcus, Peptostreptococcus, Eubacterium* and *Ruminococcus*. The number of species *Lactobacillus, Streptococcus, Fusobacterium, Veillonella, Propionibacterium* and *Enterobacteriaceae* is slightly less. Some of the species represent useful microbes, whereas others may even be harmful (Tannock, G. W. 1998, Int. Dairy J. 8:527-533). Changes in the composition of the intestinal flora or a sudden reduction in the amount of it (due to severe diarrhea, antibiotics treatment, etc.) increase the infectivity of potentially pathogenic species, which may have serious consequences (outbreak of allergies, intestinal diseases, cancer).

In a preferred embodiment of the invention, the peptide or pilus structure binds to the gastrointestinal tract (GIT), most preferably to the epithelium of the gastrointestinal tract. In another preferred embodiment of the invention, the peptide or pilus structure binds to the mucus. Mucus is a slippery secretory product, a viscous colloid, from mucus-producing cells. Mucus protects epithelial cells for example in the GIT. In addition to antiseptic enzymes and immunoglobulins mucus also contains mucins and inorganic salts. As used herein, gastrointestinal tract refers to a tube from the mouth to the anus, which participates in digesting food. The GIT comprises the mouth, esophagus, stomach, duodenum, jejunum, ileum, small intestine, large intestine (colon), cecum, rectum and anus.

The best-documented probiotics include *L. rhamnosus* GG, *L. johnsonii* LA1, *L. casei* Shirota and *Bifidobacterium lactis* Bb12. In addition, a number of other probiotics have been described in the literature of the art. In a preferred embodiment of the invention, the peptide or pilus structure is from *Lactobacillus rhamnosus*, most preferably from *Lactobacillus rhamnosus* GG (LGG, LGG®) strain, which is a non-pathogenic Gram-positive isolate originally from the USA (U.S. Pat. No. 4,839,281A). LGG strain is isolated from human feces, it is able to grow well in pH 3 and survives even lower pH values as well as high bile acid contents. The strain exhibits excellent adhesion to both mucus and epithelial cells, and colonizes GIT. Lactic acid yield from glucose is good: when grown in MRS broth, the strain produces 1.5-2% of lactic acid. The strain does not ferment lactose and thus it does not produce lactic acid from lactose. The strain ferments following carbohydrates: D-arabinose, ribose, galactose, D-glucose, D-fructose, D-mannose, rhamnose, dulcitol, inositol, mannitol, sorbitol, N-acetylglucosamine, amygdalin, arbutin, esculin, salicin, cellobiose, maltose, saccharose, trehalose, melezitose, gentibiose, D-tagatose, L-fucose, and gluconate. The strain grows well at 15-45° C., the optimum temperature being 30-37° C. LGG has been deposited with the depository authority American Type Culture Collection under accession number ATCC 53103.

Pilus Genes

The genes encoding the pilin proteins of a pilus structure are clustered on the same loci in the LGG genome. Altogether two different gene clusters encoding the pilus peptides were found by bioinformatic methods in the LGG genome (FIG. 2).

In one preferred embodiment of the invention, the polynucleotide has a sequence of any one of seq id nos 9-16 or a degenerate or fragment thereof, or it encodes the peptide of the invention or a fragment thereof. A polynucleotide that has a degenerate of a sequence shown in any one of seq id nos 9-16 means that it contains one or more different nucleotides, but still encodes for a same amino acids. A "polynucleotide" as used herein is a sequence of nucleotides such as DNA or RNA sequence, and may be a single or double stranded polynucleic acid. The term polynucleotide encompasses genomic DNA, cDNA and mRNA. Also, the polynucleotide may be isolated DNA.

In another preferred embodiment of the invention, the gene cluster comprises at least one polynucleotide of the invention. In another preferred embodiment of the invention, the gene cluster comprises at least two, at least three or at least four polynucleotides of the invention. Most preferably the gene cluster comprises polynucleotides shown in Seq ID Nos 9-12 or Seq ID Nos 13-16. As used herein, "a gene cluster" refers to a group of at least two genes that encode for peptides/proteins needed for a joint function (concerted action), here e.g. for the pilus structure. The genes of the same cluster are usually grouped together on the same genetic locus.

According to a specific embodiment of the invention, the polynucleotide has at least 30, 35, 40, 45, 50, 55, 60, 65, 70, 75, 80, 81, 82, 83, 84, 85, 86, 87, 88, 89, 90, 91, 92, 93, 94, 95, 96, 97, 98, 99, 99.5, 99.8, 99.9 or 100% identity to any one of the nucleotide sequences of Seq ID No. 9, 10, 11, 12, 13, 14, 15 or 16, or fragments thereof.

In another specific embodiment of the invention the polynucleotide has a sequence shown in any one of the sequences Seq ID No 9, 10, 11, 12, 13, 14, 15 or 16.

Products and Pharmaceutical Compositions

In one preferred embodiment of the invention, the product comprises at least one peptide or pilus structure of the invention. The product may also comprise at least two or at least three peptides of the invention. In one preferred embodiment, a product comprises at least one fragment of the peptide of the invention. The products of the invention may be selected from but are not limited to the group consisting of food products, animal feed, nutritional products, food supplements, food ingredients, health food, pharmaceutical products and cosmetics. In one preferred embodiment of the invention, the product is a food or feed product. In another embodiment of the invention the product is functional food, i.e. food having any health promoting and/or disease preventing or treating properties. Preferably a food product of the invention is selected from the group consisting of dairy products, bakery product, chocolate and confectionary, sugar and gum confectionary, cereal products, snacks, berry or fruit based products and drinks/beverages. Dairy products include but are not limited to milk, sour milk, yogurts and other fermented milk products such as cheeses and spreads, milk powders, children's food, baby food, toddler's food, infant formula, juices and soups. In addition to the peptides or pilus structures of the invention, the product may also contain other starters, probiotics etc.

In a preferred embodiment of the invention the product is a pharmaceutical composition. In one preferred embodiment of the invention, the pharmaceutical composition comprises at least one peptide or pilus structure of the invention, and in another embodiment, at least two, or at least three peptides of the invention. The pharmaceutical compositions may be used for example in solid, semisolid or liquid form such as in the form of tablets, pellets, capsules, solutions, emulsions or suspensions. Preferably the composition is for oral administration or for enteral applications.

In addition to at least one peptide or pilus structure of the invention, the pharmaceutical composition may comprise prebiotics, pharmaceutically acceptable carrier(s) (e.g. water, glucose or lactose), adjuvant(s), excipient(s), auxiliary excipient(s), antiseptic(s), stabilizing, thickening or coloring agent(s), perfume(s), binding agent(s), filling agent(s), lubricating agent(s), suspending agent(s), sweetener(s), flavoring agent(s), gelatinizer(s), anti-oxidant(s), preservative(s), buffer(s), pH regulator(s), wetting agent(s) or components normally found in corresponding products.

The product or pharmaceutical composition of the invention comprises the peptide or pilus structure in an amount sufficient to produce the desired effect. Other ingredients as well as other specific components of the products or pharmaceutical compositions are either obtained commercially or prepared by conventional techniques known in the art.

The products or pharmaceutical compositions may be manufactured by any conventional processes known in the art. Generating the peptide or pilus structure to a product means that the peptide or pilus structure may for example be added to any products or mixed with any agents. The peptide or pilus structure may also be generated in a product for example by expression in appropriate conditions. The peptide or pilus structure may be added or mixed either in connection with the preparation or thereafter, during the finishing of the end product. In a preferred embodiment of the invention, the peptide or pilus structure of the invention is added to a product.

Production Methods

The peptide or pilus structure of the invention can be produced for example by synthetic methods e.g. peptide synthesis or by recombinant production with genetically modified organism. In a preferred embodiment of the invention, the peptide or pilus structure is recombinant. As used herein, "recombinant" genetic material refers to a material, which is typically a combination of one or more genetic material, e.g. DNA strands of various origin, and it has been produced by combining or inserting the sequences. Recombinant production enables achieving specific and/or special traits into a gene or gene product or for example into expression of a gene (e.g. over- or underexpression). The polynucleotide of the invention may for example be put under the control of any endogenous or exogenous regulators, such as promoters. Recombinant protein is derived from recombinant DNA.

At least one polynucleotide of interest may be isolated from a cell or produced synthetically. This nucleotide can be transformed to a host cell. A suitable host cell for producing any peptide of the invention may be any eukaryotic cell or micro-organism, preferably bacteria, most preferably lactic acid bacteria such as lactobacilli, lactococci, bifidobacteria, enterococci, leuconostoc, and streptococci, or propionibacteria or yeast.

As used herein, "transformation" refers to a genetic alteration of a cell by foreign genetic material, preferably DNA, resulting in expression of this genetic material. The foreign genetic material can be introduced as such or as incorporated into any other genetic material such as vectors, plasmids etc. Any method of genetic engineering or any molecular cloning methods can be used for transforming a host cell with the polynucleotide of the invention. There are various methods of introducing foreign material into a eukaryotic cell. Materials such as polymers (e.g. DEAE-dextran or polyethylenimine), liposomes and nanoparticles (e.g. gold) have been used as carriers for transformation. Genetic material can also be introduced into cells by using for example viruses or vectors as carriers. Other methods for introducing foreign material into a cell include but are not limited to nucleofection, electroporation, conjugation, transfection, sonoporation, heat shock and magnetofection. The use of various transfection reagents such as calcium phosphate or lipofectamine is well known in the art. Preferable method for introducing foreign material into a bacterial cell is electroporation.

The peptide or pilus structure of the invention may also be produced by cells expressing the peptides or pilus structures naturally.

After a natural cell or transformed host cell has produced the peptide of the invention in appropriate conditions, the peptide can for example be purified from the cell or a secreted form of the peptide can be recovered e.g. from culture media. In order to purify the peptide, the cell may be disrupted for example by sonication, radiation, heating, lysis, mechanical agitation (sharing), enzymatic methods, 'cell pomb' or chemical agents (hypotonic shock, detergents, and solvents) or mixtures thereof. The peptide or pilus structure is obtainable from growing or metabolically active, i.e. live and/or lyophilized, or non-viable e.g., heat-killed, irradiated or lysed organisms. The peptide or pilus structure is obtainable from a dead cell or a living cell.

The peptide or pilus structure can be produced in one cell and then displayed on the same cell, or the peptide or pilus structure may be produced in another cell than on which it is displayed.

Figure 3:
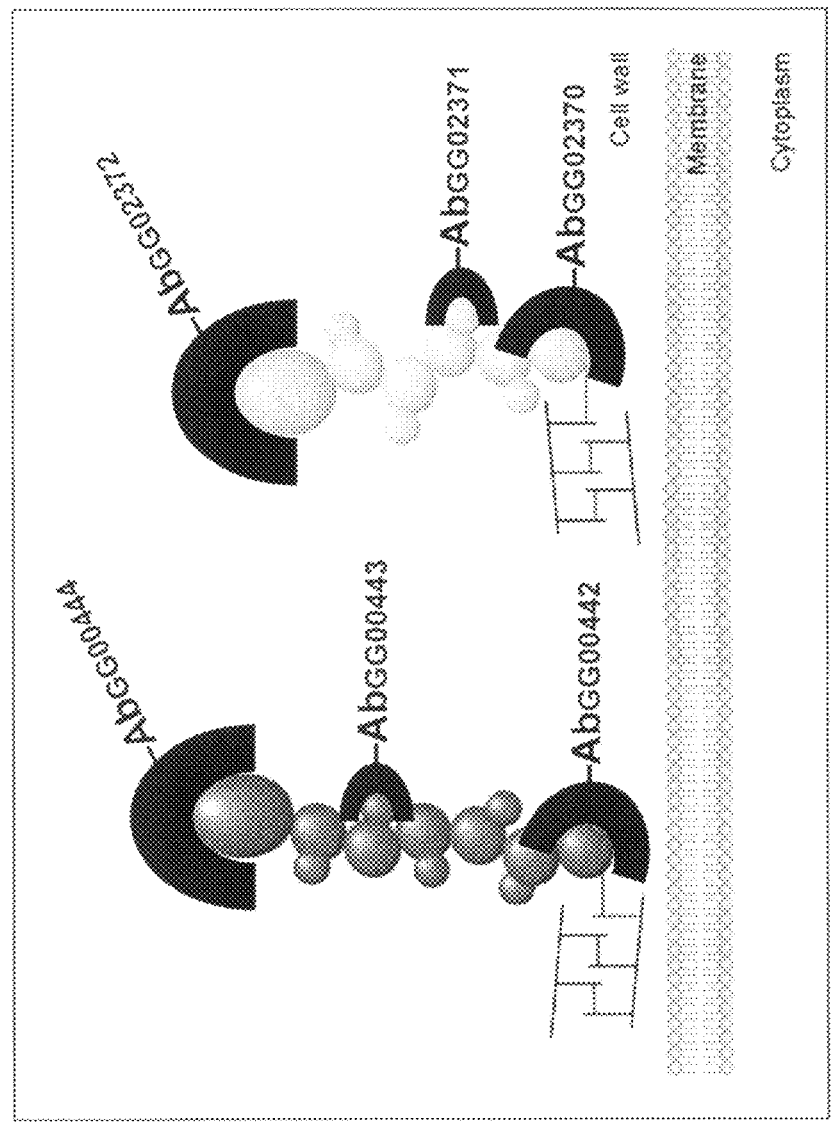
FIG. 3 shows examples of polyclonal antibodies binding to peptides GG00442, GG00443, GG00444, GG02370, GG02371 and GG02372 of the LGG pilus structure.

Any known methods such as immunization can be used for producing antibodies against the peptides of the invention. Antibodies can be generated against any epitopes or functional domains of the peptides and they can be either monoclonal or polyclonal. In a preferred embodiment of the invention, the antibodies are polyclonal (FIG. 3). As used herein, "functional domain of a peptide" refers to any part of the peptide, which has a biological function.

Treatments

Bacteria, a large group of unicellular micro-organisms, cause various diseases in eukaryotes, such as human beings, animals and plants. However, it is only within recent years that the presence of pili on the surface of important pathogens has gained interest among researches. Because GIT and its microbiota affect the well being of the subjects, utility of the pili of the bacteria potentiates novel treatments. The peptides, pilus structures or polynucleotides of the invention can be utilized in a method of treating or preventing diseases either caused by micro-organisms, such as bacteria or virus, or caused by any other reason, such as unbalanced nutrition, stressed life style or genetic pre-disposition. Diseases or ailments, which can be prevented or treated with the peptides, pilus structures, polynucleotides or with the pharmaceutical products of the invention include but are not limited to diarrhea such as traveler's diarrhea, arterial hypertension, vascular diseases, allergy, atopic diseases, urinary tract infections, respiratory infections, dental caries, irritable bowel syndrome, inflammatory bowel disease as well as remedying minor bowel discomfort and enhancing/promoting one's overall well-being. The composition of the invention is also useful for the prevention and treatment of gastrointestinal disorders and diseases, and for promoting general health. The disorders or diseases are preferably selected from the group consisting of mucosal inflammation, gut permeability disorders, IBD, IBS, and other gastrointestinal disorders. In a special embodiment of the invention peptides or pilus structures are used as vaccines (immunological response).

The method of reducing or inhibiting the adhesion of pathogenic bacteria to the GIT of a subject results in preventing or alleviating the symptoms caused by the pathogen. The pathogen is displaced from the epithelia or surface of the GIT by competition with the peptide or pilus structure of the invention. The preferred pathogens to be displaced include but are not limited to *Escherichia coli, salmonella, bacilli*, bacteroides, listeria, *staphylococci, enterococci, clostridia* and *streptococci*. As used herein, "pathogenic bacteria" refers to any bacteria causing any disease or any harmful effect. As used herein "adhesion" refers to anchoring of at least two molecules or structures to each other by chemical or physical bonds/forces or without them. Different types of adhesion such as mechanical adhesion, chemical adhesion, dispersive adhesion, electrostatic adhesion and diffusive adhesion are known. Adhesion can be a reversible or irreversible event, but in a biochemical system, adhesion is usually reversible.

*Enterococcus faecalis* and *Enterococcus faecium* are intestinal bacteria that are emerging nosocomial pathogens, including vancomycin-resistant enterococci (VRE) that are highly resistant to the important clinical antibiotic vancomycin (de Regt M. J. et al. 2008, J Antimicrob Chemother. 62(6):1401-1406). Recently, it has been described that *E. faecium* isolates contain surface located pili and remarkably, the vast majority (71%) of the hospital-acquired and an important fraction (43%) of the non-hospital strains of *E. faecium* contain pilus genes (Hendricks A. P. et al. 2008, Microbiology 154:3212-3223). In a double-blind and placebo-controlled study it has been described that consumption of *Lactobacillus rhamnosus* GG effectively cleared enterococci from infection in VRE-positive patients (Manley K. J. et al. 2007 Med J Aust. 186(9):454-457). Molecular support for the competition between pili-containing *Lactobacillus rhamnosus* GG and VRE originates from binding studies that showed that *Lactobacillus rhamnosus* has 20-130 fold higher binding to human gastrointestinal mucus than vancomycin-resistant *E. faecium* (Pultz N J. et al. 2006 Curr Microbiol. 52(3):221-224). Surprisingly, in a binding assay of this invention, the purified His-Tag labelled LGG proteins SpaA, SpaB and SpaC inhibit pathogens e.g. vancomycin-resistant *E. faecium* from binding to the mucus.

The method of reducing or inhibiting the adhesion of pathogenic bacteria to the gastrointestinal tract, to the epithelium or to the mucus of a subject may comprise the following steps: i) producing at least one peptide of the invention or fragment thereof or pilus structure; ii) displaying the peptide and/or pilus structure on the cell or mucus.

In addition to reducing adherence of harmful or pathogenic bacteria, the present invention also offers the possibility to promote the adhesion of beneficial cells or other agents such as enzyme(s), recombinant cells, microcapsule, nanocapsule or medicament(s) to the GIT. The method of promoting the adhesion of a bacterial cell to the mucus and to the GIT or a use of a peptide or a pilus structure of the invention for promoting the adhesion of a bacterial cell to the gastrointestinal mucus relates to a surprising ability of the novel peptides or pilus structures to adhere to the GIT in vivo, ex vivo or in vitro. The pilus peptide or structure functions as a tool for linking a cell or any other agent such as medicaments, enzyme(s), micro-organism(s), recombinant cells, microcapsule or nanocapsule to the GIT.

The method of modifying the immune response in a subject and use of the peptides or pilus structure for modifying the immune response are based on a surprising finding that the peptides or the pilus structure of the invention cause changes in the immune response. Immune response refers to a response to an antigen in the body, in ex vivo or in vitro system or to a response to another modulator. This response can be mediated by lymphocytes and/or recognition of antigens by specific antibodies. One goal of the immune response is to destroy the antigen, which usually is of foreign origin, or to neutralize it. As used herein, "modifying" refers to any alteration of the immune response such as increase or decrease. Alterations of an immune response can be monitored by any suitable medical, physiological or biological test including but not limited to those, which are based on detecting activation of signalling pathways as well as detecting a transcription or translation level of marker genes or the amount of proteins, e.g. antibodies or receptors. A single marker is not currently available for determining the immune response in a cell or organism. However, preferable markers include but are not limited to tumor necrosis factor alpha (TNF-α), interleukin 12 (IL-12), IL-10, IL-1 β, and interferon alpha (IFN-α). Other possible markers are IL-1α, IL-6, IL-18, IFN-γ, IL-4, TGF-β, IL-I Ra and IL-18BP. In a preferred embodiment of the invention, the marker(s) is/are selected from a group consisting of TNF-α, Th1 cytokines, IL-10 and IL-12.

Alterations of immune response can be checked by in vitro, ex vivo or in vivo tests from any biological sample or subject. The properties of probiotic strains may be investigated in cell cultures (in vitro) utilizing for example peripheral blood mononuclear cells (PBMC), human monocytes, macrophages and dendritic cells. Examples of ex vivo experiments include determination of phagocytosis of neutrophils and monocytes, oxidative burst i.e. superoxide generation of neutrophils and monocytes, NK cell activity, lymphocyte proliferation and production of cytokines by peripheral blood mononuclear cells, monocytes or lymphocytes. In vivo experiments include but are not limited to determination of a response to vaccines (e.g. vaccine specific antibodies or vaccine-specific antibody forming cells), delayed type hypersensitivity and response to attenuated pathogens.

As an alternative to probiotic effects, the peptides or pilus structures of the invention may cause any other effects in a cell or a subject. These other effects may also occur alone or in addition to probiotic effects. Probiotic effect may be a combination of other immunomodulator(s) and peptides or pilus structures.

In the present invention, the subject for treatments or preventions can be any eukaryotic organism, preferably a human being or an animal, especially pets and production animals. The animal may be selected from a group consisting of production animals and pets, such as cows, horses, pigs, goats, sheep, poultry, dogs, cats, rabbits, reptiles and snakes.

Screening Methods

Any polynucleotide of the invention or any fragment thereof can be used for screening bacterial strains having similar pilus structures. In the method of screening bacterial strains, at least one polynucleotide or fragments thereof encoding for pilus peptides or fragments thereof can be determined for example by PCR based methods, such as conventional PCR and sequencing or minisequencing; hybridisation methods, such as Southern or Northern hybridizations; any bioinformatic methods utilizing different programs and parameters; and any antibody based methods by using antibodies against peptides of the invention, flow cytometry, immunoprecipitation co-immunoprecipitation, immunohisto-chemistry, immunofluorescence, ELISA and ELISPOT techniques. Therefore, in a preferred embodiment of the invention new bacterial strains having pilus structures are screened by PCR using primers designed on LGG pilus-genes. In another preferred embodiment of the invention, new bacterial strains having pilus structures are screened by Southern hybridization using amplification products of LGG genes of the invention as probes.

Stringent hybridisation conditions for primers or probes are preferred in the methods for screening homologous sequences or fragments to the polynucleotide of the invention. As used herein "homologous sequence" or "sequence having high identity" refers to a sequence, which may be identical but does not have to be identical to the other sequence. However, the sequences are similar and they have high identity %.

In another preferred embodiment of the invention, new bacterial strains and meta-populations having pilus structures are screened by computational approaches from existing or newly created sequence listings or data-bases.

The sample to be screened can be taken from any organism or any matter, and may be e.g. bacterial culture, tissue sample, blood sample (serum or plasma sample), food sample or environmental sample. In a preferred embodiment of the invention the bacterial strain to be screened is a potential probiotic bacterial strain.

In the present invention, screening can be carried out in vivo, in vitro, in silico or ex vivo conditions.

The present invention is illustrated by the following examples, which are not intended to be limiting in any way.

Example 1

Cloning, Expression, and Purification of Recombinant LGG Pilin Proteins

The coding sequences for SpaA (GG00442), SpaB (GG00443), SpaC (GG00444), SpaD (GG02370), SpaE (GG02371), and SpaF (GG02372), excluding the region encoding the N-terminal signal peptide and the C-terminal cell wall sorting signal (CWSS), were PCR amplified from LGG genomic DNA using pairs of flanking 5'- and 3'-end oligonucleotide primers, one containing an EcoRI site (a SacI site for GG02372) and another with a XhoI site (see Table 1). The amplified PCR fragments were cleaved with EcoRI (or SacI for GG02372) and XhoI restriction endonucleases, then ligated into the corresponding sites in the T7-regulated expression vector pET28b+, and the resulting recombinant plasmids (pKTH5319 for GG00442, pKTH5320 for GG00443, pKTH5321 for GG00444, pKTH5324 for GG02370, pKTH5379 for GG02371, and pKTH5341 for GG02372) propagated in the $E.\ coli$ strain BL21 (DE3) pLysS for the expression of intracellular C-terminal hexahistidine-tagged proteins. Established procedures were employed in all DNA manipulations using standard protocols. For protein production, $E.\ coli$ was grown at 37° C. to midlog phase in Luria-Bertani medium supplemented with 50 µg/ml kanamycin, protein expression induced for three hours by 1 mM IPTG, the cells harvested by centrifugation, and the cell pellet resupended in lysis buffer [50 mM $NaH_2PO_4$(pH 8.0), 300 mM NaCl, 10 mM imidazole]. The cells were disrupted by sonication, clarified by centrifugation, and the cell-free lysates passed through a 0.45 µm filter. The hexahistidine-tagged pilin proteins were then purified by $Ni^{2+}$-chelating affinity chromatography. Briefly, the cell-free lysates were each applied to a column of Ni-NTA agarose (Qiagen), washed with wash buffer [50 mM $NaH_2PO_4$(pH 8.0), 300 mM NaCl, 20 mM imidazole], and the proteins eluted from the column with elution buffer [50 mM $NaH_2PO_4$(pH 8.0), 300 mM NaCl, 250 mM imidazole]. Column fractions containing purified proteins were pooled, buffer-exchanged to 10 mM Tris-HCl (pH 8.0) for the SpaA (GG00442), SpaC (GG00444), SpaD (GG02370), SpaE (GG02371), and SpaF (GG02372) proteins and to 50 mM sodium acetate (pH 5.1) for the SpaB (GG00443) protein using a BioRad EconoPac 10 DG desalting column, and concentrated using a 30 kDa Microsep filter (Pall Life Sciences). The purity of the recombinant pilin proteins were monitored by SDS-PAGE and the protein concentrations estimated by $A_{280}$ measurements.

Example 2

Generation of Recombinant LGG Pilin Protein-Specific Polyclonal Antibodies

Rabbit polyclonal antibodies specific for the SpaA (GG00442), SpaB (GG00443), SpaC (GG00444), SpaD (GG02370), SpaE (GG02371), and SpaF (GG02372) pilin proteins were produced according to the immunization protocol described by Johnston B. A. et al. (1991, Laboratory of Animal Science 41: 15-21). In brief, a subcutaneous (SC) injection (1 ml) of a 1:1 mix of 400 µg purified recombinant pilin protein in Freud's complete adjuvant was initially administered, followed by three sets of booster injections (SC) of 1:1 mixes of 200 µg protein in Freud's incomplete adjuvant at three-week intervals. The final blood collection was made two weeks after the last booster injection. The preparation of anti-sera from the blood was carried out using standard protocols.

TABLE 1

| Gene | Forward oligonucleotide primer* | Reverse oligonucleotide primer** |
|---|---|---|
| SpaA (GG00442) | 5'-TCGGGTTCAGAATTCTACGAATGATACGAC | 5'-TGCCAGTACCACCCTCGAGTGGCAGAATAC |
| SpaB (GG00443) | 5'-GCAGACACAGAATTCAACTGTGCCGACC | 5'-CAACTGTATCACCCTCGAGTGGCAACAATTGACG |

TABLE 1-continued

| Gene | Forward oligonucleotide primer* | Reverse oligonucleotide primer** |
|------|-------------------------------|--------------------------------|
| SpaC (GG00444) | 5'-CAGTTCAGTTGTGAATTCCACTGATAACATTCG | 5'-AGCCCTGACCACCCTCGAGCGGCAAAATTGC |
| SpaD (GG02370) | 5'-ACCCGTACAGAATTCGACAACGACTGTG | 5'-GTCCGATTCCGCCCTCGAGCGGCAATAATTG |
| SpaE (GG02371) | 5'-CCACATTGGGTTCAGAATTCTGATCAAACTG | 5'-TGCGCCAATCGGACTCGAGCGGCAAATAAC |
| SpaF (GG02372) | 5'-GCAAATTGGCAGGAGCTCGGTCCCGGTAG | 5'-CCGCTACCACCCTCGAGCGGTAGGAGTG | and
**Restriction endonucleases, EcoRI and SacI in the forward and XhoI in the reverse oligonucleotide primers, are underlined and in boldfaced type Example 3

Prediction of Protein-Encoding Sequences by Bioinformatic Methods

Prediction of protein-encoding sequences was accomplished using Glimmer3 (Delcher A. L. et al. 2007, Bioinformatics. 23:673-679) and analysing the completed genome sequence of LGG. Glimmer3 was applied using the iteration-mode script (g3-iterated.csh) with following modifications to default parameters: minimum gene length (150 bp) and maximum over lap (50 bp). Start sites of the initial predictions were rectified using BLAST (Altschul S. F. et al. 1997, Nucleic Acids Res. 25(17):3389-3402) and searching for putative ribosomal binding sites. The Glimmer3 predictions for GG00441, GG00442, GG00443, GG00444, GG02369, GG02370 and GG02371 were accepted as such, whereas the prediction of GG02372 was manually rectified to start 21 bp more downstream. Rho-dependent stops sites were predicted using TransTermHP (Kingsford C. L. et al. 2007, Genome Biol. 8:R22.) which showed that GG00441, GG00442, GG00443 and GG00444; GG02369, GG02370, GG02371 and GG02372 are transcribed as single transcript and thus form own operons.

Annotations were obtained by converting the predicted protein-encoding sequences to protein sequences and by performing a homology search against the public sequence database (Wheeler D. L. et al. 2008, Nucleic Acids Res. 36: D13-21). Annotations were accepted only from those sequences of which local alignments between the query had >=35% amino acid identity and covered >=80% of the sequence of the subject. Based on this search, GG00441 and GG02369 were annotated as sortase-enzymes; GG00444 as a von Willebrand factor domain containing protein; GG02370 and GG02371 as a conserved hypothetical protein and GG02372 as an outer membrane protein. No annotations were obtained for GG00442 and GG00443.

Further annotation and information about the sequences were obtained by integrating information of InterPro and COG analyses (Mulder N. J. et al. 2007, Nucleic Acids Res. 35:D224-D228; Tatusov R. L. et al. 2000, Nucleic Acids Res. 28:33-36) and doing specific domain analyses. The specific domain searches were performed using Hmmsearch tool of the Hmmer-package and using sortase associated domain models, obtained from public databases of PFAM and TIGR-FAM (Finn R. D. et al. 2008, Nucleic Acids Res. 36:D281-288; Haft D. H. et al. 2003, Nucleic Acids Res. 31:371-373). Following models were used to search for sortase-recognition sites: TIGR01167, TIGR03063, TIGR03065, TIGR03068 and PF00746 and the following models to search for sortases: TIGR01076, TIGR03064, PF04203 and PF07170. Both fs- and ls-models of the PFAM models were searched and the full length models of the TIGR models. Both search-types, the sequence and the domain search, were used. Matches scoring higher than the recorded trusted cut-off given by the database were considered significant. In cases, where the sequence-model was significant, every domain hit was accepted. These searches indicated that GG00441 and GG02369 are sortase-enzymes and that GG00442, GG00443, GG02370 and GG02372 contain the sortase-recognition site, thus being their likely substrates. Sortase-recognition sites were also searched for using regular expression searches (with the patterns LPXTG and LVNTG (Ton-That H et al. 2004, Mol Microbiol. 53:251-261), where X denotes any amino acid) revealing following matches: GG00442 and GG00443, GG00444, GG02370, GG02371 and GG02372. E-boxes were searched using YXXXETXXPX(G/N)X as the regular expression that was derived from the original YXLXETX-APXGY-pattern (Ton-That H et al. 2004, Mol Microbiol. 53:251-261). The E-box search revealed hits on GG00442, GG00443, GG00444, GG02370 and GG02372 verifying the likeliness of these sequences to be sortase-substrates. The existence of possible secretion signals was tested using SignalP3-tool using both the hidden Markov model and the neural network methods. In all cases both methods predicted that the peptide sequences of GG00441, GG00442, GG00443, GG02370, GG02371 and GG02372 contained a signal suitable for the secretion.

Example 4

Bioinformatic Screens on Public Databases

Peptide sequences, fragments thereof, variants thereof, polynucleotide sequences, fragments thereof or variants thereof according to the present invention can be used for performing computational searches against public and private sequence collections and thereby for detecting bacterial strains comprising similar peptide sequences, polynucleotide sequences or pilus structures. Another preferred use of bioinformatic screening methods is for selecting bacterial communities enriched by the peptide sequences, polynucleotide sequences or pilus structures. Bioinformatic searches offer a plausible method for the detection of strains having sequences, which are in public sequence collections but have never been annotated or curated by an expert.

Bioinformatic searches are performed using algorithms such as BLAST (Altschul S. F. et al. 1997, Nucleic Acids Res. 25(17): 3389-3402) or FASTA (Pearson W R, 1990, Methods Enzymol 183:63-98) (preferably default parameters are used). BLAST and FASTA algorithms are used to compare the selected sequences against a set of other sequences and to report statistically significant hits. Peptide sequences, polynucleotide sequences or pilus structures are searched from, for example, the following public sequence collections offered by the National Center for Biotechnology Information (NCBI): non-redundant protein sequences, environmental samples, whole-genome shotgun read and Genomic survey sequences; or preferably from a private sequence collection generated, for example, using high-throughput sequencing methods.

The peptide sequences of seq id no 1-8 or fragments thereof are used to screen for significant matches of peptides by performing a standard Blast search against the non-redundant protein sequence collection of NCBI. When a significant peptide match is found, a bacteria encoding this peptide of interest is classified as a putative probiotic strain or as a putative pathogen, against which the peptide is effective.

Example 5

Atomic Force Microscopy Showing LGG Pili

Figure 4:
FIG. 4 shows a phase contrast Atomic Force Microscope micrograph picture of protruding pili structures of LGG.

LGG strain was grown on a MRS (LabM) agar plate at 37° C. for 20 hours anaerobically. Bacterial cells were diluted in sterile water, fixed to Mica i slide and air dried. Both topographic and phase contrast figures of bacteria were obtained by Nanoscope IIIa Multimode AFM (Atomic force microscope, Digital Instruments, Santa Barbara)—microscope and J scanner (FIG. 4).

Example 6

Figure 5A:
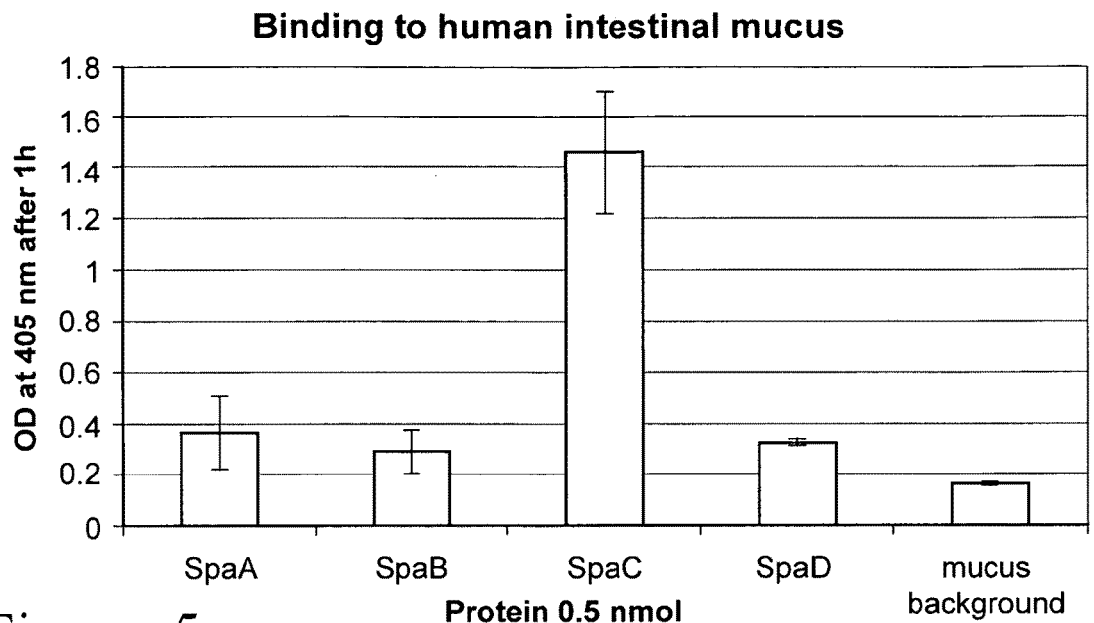
FIGS. 5a and 5b show in vitro binding of recombinant histidine-tagged LGG proteins, i.e. SpaA, SpaB, SpaC, SpaD and SpaF pilin proteins, to human intestinal mucus. Resected human intestinal tissue was used as a source of mucus on a polystyrene microtiter plate. The bound proteins were detected by enzyme-linked immunosorbent assay.
Figure 5B:
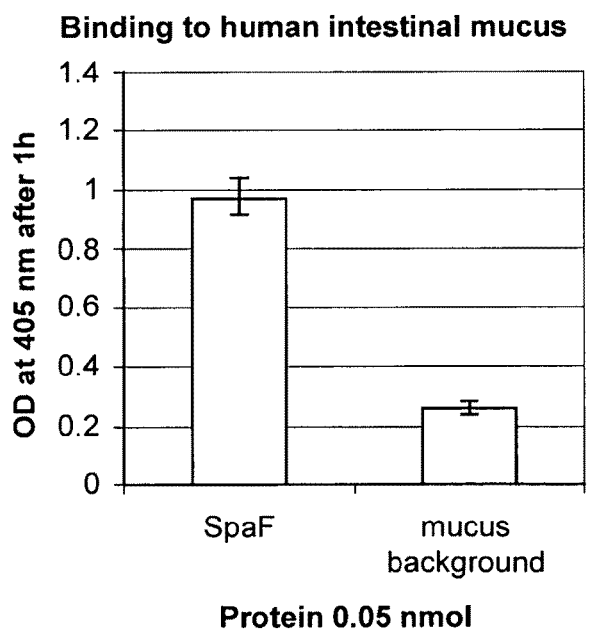

Binding of Recombinant LGG Proteins to Human Intestinal Mucus as Assessed by Non-Quantitative ELISA-Assay The binding of recombinant hexahistidine-tagged SpaA, SpaB, SpaC, SpaD, SpaF pilin proteins to human intestinal mucus was assessed in vitro. Resected human intestinal tissue was used as a source of mucus. The use of resected human intestinal tissue was approved by the joint ethical committee of the University of Turku and Turku University Central Hospital (both in Turku, Finland) and informed written consent was obtained from the patients. The mucus was isolated from the healthy part of tissue obtained from patients undergoing colonic surgery e.g. due to colorectal cancer. The processing of intestinal tissue and the isolation of mucus was done as described previously (Vesterlund S. et al 2005; Res Microbiol. 156(2):238-244; J Microbiol Methods 60(2):225-233?). Mucus was passively immobilized on a polystyrene microtiter plate (Maxisorp, Nunc, Denmark) by overnight incubation at 4° C. The wells were washed three times with phosphate-buffered saline (PBS; pH 7.2) and blocked with 0.5% (w/v) bovine serum albumin (Sigma A7030) in PBS for 1 h at room temperature. The blocking solution was removed and 0.5 or 0.05 nmol of the hexahistidine-tagged pilin proteins in BSA-PBS was added followed by 1 h incubation at 37° C. After incubation and washes the bound proteins was detected by enzyme-linked immunosorbent assay. The pilin proteins was detected by a mouse Tetra-His antibody (Qiagen, 34670) and a goat anti-mouse IgG Fab specific alkaline phosphatase conjugate (Sigma, A1293) as the secondary antibody. Dilutions 1:2000 and 1:5000 (v/v) were used for the primary and secondary antibodies, respectively. The substrate 4-nitrophenyl phosphate disodium salt (pNPP, Sigma, A7030) in diethanolamine-MgCl-buffer (Reagena, 170057, Finland) was added in concentration of 2 mg/ml and the color development was measured after 1 h at 405 nm. Results are average ±stdev from three parallel measurements (FIGS. 5a-b).

Example 7

Extraction of Cell Wall-Associated Pilus Proteins and Western Blot

Fresh 10 h cultures of LGG and LC705 (negative control) cells in MRS (LabM) were inoculated (1%) in mTSB medium (15 g/l TSB medium, BD Biosciences) enriched with 20 g/l Bacto peptone (Difco), or MRS medium supplemented with 0.6% ox gall bile (Sigma) and cultivated at 37° C. Growth was monitored by measuring optical density ($OD_{600}$) and cells in stationary growth phase were collected by centrifugation.

The fractionation of the bacterial cells was done essentially as described elsewhere (Åvall-Jääskeläinen S. et al. 2003, Appl Environ Microbiol 69:2230-2236). Briefly, the bacteria ($10^9$ cfu) were washed once with PBS and homogenized by beating three times for two minutes with glass beads in a cell mill (Bühler Vibrogen-Zellmühle). The bacterial homogenates were resuspended in 500 μl PBS and centrifuged five minutes at 1,000 g. The supernatant was centrifuged at 16,000 g for 30 minutes at +4° C. to collect the cell walls. The resulting pellets were resuspended in 50 μl of 50 mM Tris-Cl (pH 8.0) supplemented with 5 mM $MgCl_2$, 5 mM $CaCl_2$, 10 mg/ml lysozyme, and 42 U/ml mutanolysin. The resuspended cell wall pellets were incubated 3 hours at 37° C. to release the cell wall associated polypeptides.

The enzymatically treated cell wall fractions were run on a 4-15% gradient gel (Bio-Rad) and transferred to a Immobilon-P PVDF membrane (Millipore). The membrane was subjected to Western analysis with the ECL Advance™ Western Blotting Detection Kit (Amersham) according to manufacturer's instructions. The SpaA, SpaB, and SpaC pilin protein-specific polyclonal primary antibodies were diluted 1:25,000, and the Goat Anti-Rabbit IgG (H+L)-HRP-Conjugate (Bio-Rad) secondary antibody was diluted 1:100,000.

Figure 6A:
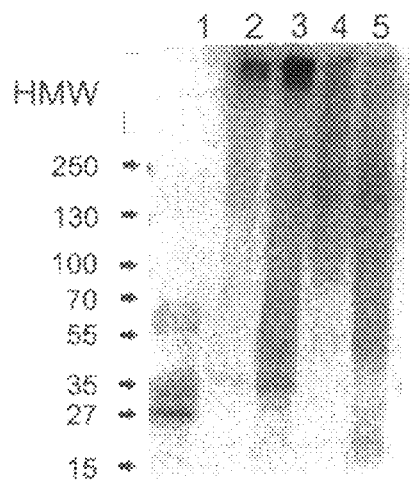
FIGS. 6a and 6b show Western blots of cell wall fractions of LGG and as a negative control *L. rhamnosus* LC705 (LC705) grown in mTSB-medium or MRS+0.6% ox gall bile medium using SpaA and SpaC pilin protein-specific polyclonal antibodies, respectively.
Figure 6B:
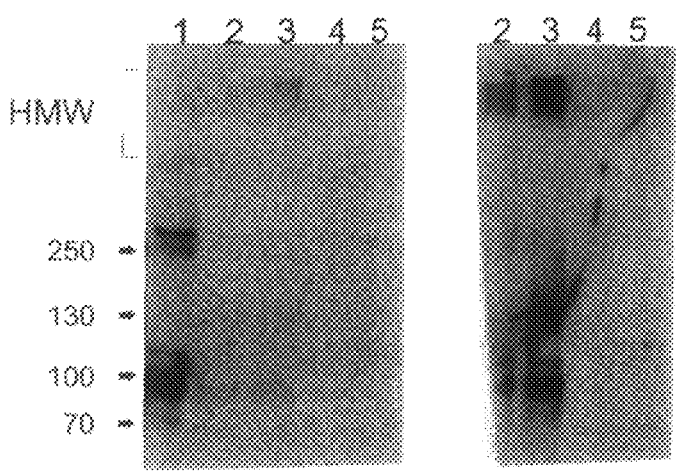

The pili in gram-positive bacteria are composed pilin subunits covalently linked to one another. The monomeric pilin subunits are added to the growing pili one by one by the action of sortases, and as a consequence, at a given time point each individual cell carries pili of different lengths on its surface (Scott J. R. and Zahner D. 2006, Mol Microbiol 62:320-330). Thus, a classical way to show the existence of pili is to subject a mutanolysin/lysozyme treated cell wall fraction to Western analysis: if pili are present, a high molecular weight ladder (HMW) will be detected on the blot, and in many instances also a pilin monomers will be observed (Scott J. R. and Zahner D. 2006, Mol Microbiol 62:320-330). The presence of SpaA and SpaC containing pili in LGG is clearly evident from FIGS. 6a and 6b, since both the monomeric SpaA and SpaC pilin subunits and HMWs can be identified from the LGG cell wall extracts using SpaA and SpaC-specific antibodies, whereas LC705 cells are deficient of SpaA and SpaC moieties. The exposure time needed to record chemiluminescent signal from the SpaC blot was 60 seconds, whereas exposure time of 1 second was sufficient for the SpaA blot, implying the SpaA to be present at higher numbers in the pili as SpaC. This difference in relative numbers might suggest the SpaA to be the shaft forming pilin subunit, whereas SpaC could serve as a pilus tip adhesin. Also of notice is that pili are found in LGG cells grown in a medium supplemented with bile, indicating that pili might be expressed in the human gastrointestinal tract.

Example 8

Screening of New Probiotic Strains Having Pili Structures by PCR

Lactobacilli are grown anaerobically in MRS broth at +37° C. for 10 hours. The genomic DNA is isolated as follows. 1 ml of the culture is centrifuged at 14 000 g for 2 min. The collected cells are resuspended in 480 µl of 50 mM EDTA, 100 µl of 50 mg/ml lysozyme (Amresco, Solon, Ohio, USA) and 20 µl of 50 U/µl mutanolysine (Sigma) is added and the mixture is incubated at 37° C. for 1 h. The mixture is centrifuged for 2 min at 14 000 g, the supernatant is discarded and the bacterial pellet is extracted with a Wizard® Genomic DNA Purification Kit (Promega) according to the manufacturer's instructions. The purified DNA is suspended in 200 µl of Tris-EDTA (TE) buffer. About 200 ng of genomic DNA is used as a template in PCR reaction. PCR is performed using Dynazyme polymerase (Finnzymes, Espoo, Finland) and oligonucleotide primers based on sequences GG00442, GG00443, GG00444 and GG02370, GG02371, GG02372 genes. The PCR reaction is performed with a PCT-200 apparatus (MJ Research, Waltham, Mass., USA) and contains 10 mM Tris-HCl, 1.5 mM $MgCl_2$, 50 mM KCl and 0.1% Triton-X 100 (pH 8.8). The primers are used at 1-µM and the deoxynucleotides at 200-µM concentrations. Initial denaturation is at 94° C. for 2 min. The first cycle is 1 min each at 95° C., 65° C. and 72° C., the next five cycles are 1 min each at 95° C., 60° C. and 72° C., and the last 25 cycles are 1 min each at 95° C., 55° C. and 72° C. To terminate cycling the reaction mixture is maintained at 72° C. for 5 min and at 4° C. for 15 min. The amplified DNA bands are separated in 0.7% agarose gel by gel electrophoresis.

twice in 0.1×SSC-0.1% SDS for 15 minutes at 68° C. Hybridization with lower stringency is performed at 60° C., and the last two washes are in 0.5×SSC-0.1% SDS at 50° C. for 15 minutes. Hybridization is detected with alkaline-phosphatase-conjugated antibody and NBT/BCIP color reaction (DIG-system, Roche).

Example 10

Immunomodulation by Purified LGG Pilus Proteins

Human macrophages are isolated from blood of healthy volunteers (buffy coat fraction) as documented previously (Miettinen M. et al. 2000, J Immunol 164:3733-3740; Miettinen M. et al. 2008, J Leuk Biol 84:1092-1100). Essentially, this is done using freshly collected, leukocyte-rich buffy coats from 4 healthy blood donors (supplied by the Finnish Red Cross Blood Transfusion Service, Helsinki Fla.) and isolating peripheral blood monocuclear cells (PBMCs) by Ficoll-Paque (Amersham Pharmacia Biotech, Uppsala SE) gradient centrifugation. Monocytes are purified from PBMCs by adherence on six-well plastic plates (Falcon Becton Dickinson, Franklin Lakes N.J., US) and cultured for 7 days in macrophage—serum-free medium (Gibco Invitrogen, Grand Island N.Y., US) in the presence of 10 ng/ml recombinant human (rh) GM-CSF (Leucomax, Schering-Plough, Innishannon, IRL) to obtain macrophages. Macrophages are incu-

TABLE 2

| Gene | Forward oligonucleotide primer | Reverse oligonucleotide primer |
|---|---|---|
| SpaA (GG00442) | 5'-TCTCGGGTTTAATGGCACTC | 5'-TCTGTATTGGCAGCAGCATC |
| SpaB (GG00443) | 5'-TCCTTCCGTCCGTTAGTGAT | 5'-CGTTTGTGGCAACAATTGAC |
| SpaC (GG00444) | 5'-CCAAATTGGCAACAGACCTT | 5'-GCCATCTGGTGCTTTTGTTT |
| SpaD (GG02370) | 5'-CGGACGCCTTTTACCAATTA | 5'-AACAGGTTTCGTACCGCATC |
| SpaE (GG02371) | 5'-TATGACGCGTAAGCAAGCAC | 5'-TGGCCGTCAATTAACACAAA |
| SpaF (GG02372) | 5'-CTACCGGAGCATGTCGAGTT | 5'-GGCCATTTTCATCAGTCGTT |

Example of the primers for amplification of pili genes are shown in Table 2, but are not limited to those. The sizes of the amplified PCR-products using L. rhamnosus GG DNA as a template and Table 2 primers are 780 bp, 612 bp and 801 bp for SpaA, SpaB, SpaC, respectively, and for SpaD, SpaE and SpaF 688 bp, 705 bp and 799 bp.

Example 9

Screening of New Probiotics Having Pili Genes by Southern Hybridization

New probiotic strains having pili structures are screened by Southern hybridization using LGG amplification products from Example 8 as probes. Hybridization conditions can be adjusted to stringent, enabling probe hybridization only to identical sequences, or to low stringent, allowing some amount of sequence discrepancy. The PCR amplification products of SpaA, B, C, D, E and F are purified in NuSieve low melt agarose (FMC Bioproducts, Rockland, Me., USA) and labelled with DIG-system (Roche Diagnostics). The total DNA of the bacterial strains is digested with EcoRI and the resulting fragments are separated in 0.7% agarose gel. The DNA fragments in agarose are blotted onto nylon membranes and hybridized according to standard procedure of DIG-system. Stringent hybridization is performed at 68° C., washes are twice in 2×SSC-0.1% SDS at room temperature, and bated at a concentration of approximately 4 million cells per well in a 6-well microtiter plate and stimulated with an equivalent number of live bacteria (LGG and *Streptococcus pyogenes* T1M1) or approximately 3, 100, 3000 or 10000, etc., fmol of purified His-Tag labelled LGG proteins SpaA and SpaC. After incubation for 6 h and 24 h, the modulation of the amounts of immune markers or activation of signalling pathways or receptor expression is determined as described previously (Miettinen M. et al. 1996, Infec immunol 64:5403-5405; Miettinen M. et al. 2000, J Immunol 164:3733-3740; Miettinen M. et al. 2008, J Leuk Biol 84:1092-1100).

Typically, cells of the probiotic LGG and the pathogen *S. pyogenes* T1M1 show immunomodulatory activities and induce a specific Th1-like response in PBMCs or macrophages (Miettinen M. et al. 2000, J Immunol 164: 3733-3740; Veckman V. et al. 2003, J Leuk Biol 74:395-402). Remarkably, the purified LGG pili proteins also induce a response in macrophages, demonstrating their functionality in immunomodulation. Moreover, these experiments show that the LGG pili proteins signal to human host cells.

Example 11

Competition Assay with LGG Pilus Proteins

The processing of intestinal tissue and the isolation of mucus was done as described in Example 6.

The competition assay is carried out according to Vesterlund S. et al. 2006 (Microbiology 152(6):1819-1826). Mucus (Sigma), at a concentration 0.5 mg/ml, is passively immobilized on a polystyrene microtiter plate (Maxisorp, Nunc, Denmark) by overnight incubation at 4° C. The wells are washed three times with phosphate-buffered saline (PBS; pH 7.2) and blocked with 0.5% (w/v) bovine serum albumin (Sigma A7030) in PBS for 1 h at room temperature. The blocking solution is removed and 5.0 or 0.05 nmol of the histidine-tagged pilin protein or pili structure in BSA-PBS is added followed by 1 h incubation at 37° C. The unbound pili proteins or pili structures are washed away as described above.

The pathogenic bacterial cells are added to the wells in a volume of 100 μl, four parallel wells are used in each experiment. Bacteria are allowed to adhere for 1 h at 37° C. and the wells are washed three times with 250 μl PBS to remove the nonadherent bacteria. The bacteria bound to mucus are released and the genomic DNA extracted by Wizard Genomic kit (Promega). The number of bacteria in a sample is determined by quantitative PCR using species specific primers and SYBR Green detection. The adhesion ratio (%) of bacteria is calculated by comparing the number of adhered bacteria to that of added bacteria. LGG pili proteins and pili structures inhibit adhesion of pathogenic bacterium to the mucus.

The invention claimed is:

1. An isolated peptide comprising a sequence having at least 94% sequence identity with SEQ ID NO: 4 (GG00444).

2. The peptide according to claim 1, which is a recombinant peptide.

3. The peptide according to claim 1, which is from bacteria.

4. The peptide according to claim 3, which is from *Lactobacillus rhamnosus*.

5. The peptide according to claim 4, which is from *Lactobacillus rhamnosus* GG (LGG) strain.

6. The peptide according to claim 1, which binds to the gastrointestinal tract.

7. The peptide according to claim 1, which binds to the mucus.

8. A product comprising the peptide according to claim 1.

9. The product according to claim 8, which is a food or feed product.

10. The food product according to claim 9, wherein the food product is selected from the group consisting of a dairy products, a bakery product, a chocolate, a confectionary, a sugar confectionary, a gum confectionary, a cereal product, a snack, a berry based product, a fruit based product, a drink and a beverage.

11. The food product according to claim 10, wherein the food product is selected from the group consisting of a milk product, a sour milk product, a yogurt, a cheese, a spread, a milk powder, a children's food, a baby food, a toddler's food, an infant formula, a juice and a soup.

12. A pharmaceutical composition comprising the peptide according to claim 1.

13. A method of treating a disorder selected from the group consisting of diarrhea, arterial hypertension, vascular disease, allergy, cancer, atopic disease, viral disease, infectious disease, urinary tract infection, respiratory infection, dental caries, irritable bowel syndrome, inflammatory bowel disease, mucosal inflammation, gut permeability disorder, obesity, metabolic syndrome, oxidative stress and abdominal pain in a subject in need thereof, comprising administering the peptide of claim 1 to the subject.

14. A method of reducing or inhibiting the adhesion of pathogenic bacteria to the gastrointestinal tract, to the epithelium or to the mucus of a subject, comprising administering the peptide according to claim 1 to the subject.

15. The peptide according to claim 1 comprising a sequence having at least 95% sequence identity with SEQ ID NO:4 (GG00444).

16. The peptide according to claim 1, which is a purified peptide.

* * * * *

SEQUENCE LISTING

<160> NUMBER OF SEQ ID NOS: 42

<210> SEQ ID NO 1
<211> LENGTH: 359
<212> TYPE: PRT
<213> ORGANISM: Lactobacillus rhamnosus

<400> SEQUENCE: 1

```
Met Thr Lys Arg Thr Arg Arg Pro Leu Asp Leu Ile Asp Ile Val Ile
1               5                   10                  15

Gly Cys Leu Leu Leu Ala Gly Phe Gly Val Leu Cys Tyr Pro Phe Ala
            20                  25                  30

Ser Asp Ala Tyr Val Ser Tyr Gln Asn Gln Val Ile Asp Arg Tyr
        35                  40                  45

Arg Gln Gln Glu Ala Arg Lys Asn Gln Met Val Leu Arg Arg Glu Tyr
    50                  55                  60

Asn Asp Tyr Gln Gln Lys Asn Lys Gln Leu Ala Ala Ser Gln Gln Val
65                  70                  75                  80

Pro Gly Val Ala Ser Phe Asn His Ala Val Asn Asp Gln Gly Thr Ala
                85                  90                  95

Lys Thr Ala Ala Lys Arg Asn Gln Gln Ile Leu Thr Arg Gln Thr Val
            100                 105                 110

Ala Gln Leu Thr Ile Pro Lys Ile Gly Leu Ser Leu Pro Val Phe Asp
        115                 120                 125

His Thr Ser Asp Trp Leu Leu Gln Phe Gly Ala Cys Leu Leu Asp Gly
    130                 135                 140

Thr Ser Tyr Pro Thr Gly Gly Lys Asn Thr His Ala Val Ile Ser Ala
145                 150                 155                 160

His Arg Gly Val Pro Asn Ala Glu Leu Phe Thr Arg Val Pro Ala Leu
                165                 170                 175

Lys Lys Gly Asp Lys Phe Phe Ile Ser Ile Gly Asn His Lys Leu Ala
            180                 185                 190

Tyr Gln Val Phe Lys Arg Gln Val Ile Glu Pro Ser Asp Thr Arg Gln
        195                 200                 205

Leu Arg Ile Val Pro Gly Gln Asp Leu Val Thr Leu Met Thr Cys Thr
    210                 215                 220

Pro Tyr Met Ile Asn Ser His Arg Leu Leu Ile Thr Gly Arg Arg Ile
225                 230                 235                 240

Pro Tyr Val Lys Ala Asp Glu Glu Ala Ser Ser Trp Ala Val Trp Trp
                245                 250                 255

Asn Lys Leu Lys Leu Ile Val Ala Leu Leu Gly Ala Val Ile Ile Leu
            260                 265                 270

Gly Val Ile Gly Phe Val Met Arg Ser Leu Met Leu Gly Arg Lys His
```

```
            275                 280                 285
Tyr Leu Leu Glu Val Pro Ala Glu Ala Thr Gln Val Val Lys Arg
    290                 295                 300

Gly Arg His Ile His Ser Phe Lys Ser Asp Gln Thr Gly Val Thr Asp
305                 310                 315                 320

Ile Ser Leu Pro Gly Asn His Tyr Arg Val Ala Ile Val Thr Pro Leu
                325                 330                 335

Gly Arg Thr Lys Tyr Lys Ala Tyr Val Lys Lys Ile Arg Asp Lys Ser
            340                 345                 350

Phe Gln Leu Lys Glu Tyr His
            355

<210> SEQ ID NO 2
<211> LENGTH: 334
<212> TYPE: PRT
<213> ORGANISM: Lactobacillus rhamnosus

<400> SEQUENCE: 2

Met Lys Lys Thr Ile Ala Lys Lys Val Leu Thr Leu Thr Ser Thr Ile
1               5                   10                  15

Leu Met Thr Leu Leu Met Val Leu Gly Phe Asn Gly Thr Arg Val Gln
                20                  25                  30

Ala Asp Thr Asn Asp Thr Thr Thr Gln Asn Val Val Leu Thr Lys Tyr
            35                  40                  45

Gly Phe Asp Lys Asp Val Thr Ala Ile Asp Arg Ala Thr Asp Gln Ile
        50                  55                  60

Trp Thr Gly Asp Gly Ala Lys Pro Leu Gln Gly Val Asp Phe Thr Ile
65              70                  75                  80

Tyr Asn Val Thr Ala Asn Tyr Trp Ala Ser Pro Lys Asp Tyr Lys Gly
                85                  90                  95

Ser Phe Asp Ser Ala Pro Val Ala Thr Gly Thr Thr Asn Asp Lys
            100                 105                 110

Gly Gln Leu Thr Gln Ala Leu Pro Ile Gln Ser Lys Asp Ala Ser Gly
        115                 120                 125

Lys Thr Arg Ala Ala Val Tyr Leu Phe His Glu Thr Asn Pro Arg Ala
    130                 135                 140

Gly Tyr Asn Thr Ser Ala Asp Phe Trp Leu Thr Leu Pro Ala Lys Ala
145                 150                 155                 160

Ala Ala Asp Gly Asn Val Tyr Val Tyr Pro Lys Asn Val Gln Lys Thr
                165                 170                 175

Thr Tyr Glu Arg Thr Phe Val Lys Lys Asp Ala Glu Thr Lys Glu Val
            180                 185                 190

Leu Glu Gly Ala Gly Phe Lys Ile Ser Asn Ser Asp Gly Lys Phe Leu
        195                 200                 205

Lys Leu Thr Asp Lys Asp Gly Gln Ser Val Ser Ile Gly Glu Gly Phe
    210                 215                 220

Ile Asp Val Leu Ala Asn Asn Tyr Arg Leu Thr Trp Val Ala Glu Ser
225                 230                 235                 240

Asp Ala Thr Val Phe Thr Ser Asp Lys Ser Gly Lys Phe Gly Leu Asn
                245                 250                 255

Gly Phe Ala Asp Asn Thr Thr Tyr Thr Ala Val Glu Thr Asn Val
            260                 265                 270

Pro Asp Gly Tyr Asp Ala Ala Ala Asn Thr Asp Phe Lys Ala Asp Asn
        275                 280                 285

Ser Ser Ser Asp Ile Leu Asp Ala Pro Ser Gly Ile Leu Pro His Thr
```

```
                290                 295                 300
Gly Gly Thr Gly Thr Val Ile Phe Ala Ile Leu Gly Val Ala Leu Ile
305                 310                 315                 320

Ala Phe Gly Ala Val Ala Tyr Arg Lys Arg Arg Asn Gly Phe
                325                 330

<210> SEQ ID NO 3
<211> LENGTH: 241
<212> TYPE: PRT
<213> ORGANISM: Lactobacillus rhamnosus

<400> SEQUENCE: 3

Met Thr Lys Ser Phe Arg Pro Leu Val Ile Leu Thr Phe Cys Leu Ala
1               5                   10                  15

Leu Leu Val Ser Leu Ala Thr Thr Thr Leu Gln Gln Thr Gln Ala Ala
                20                  25                  30

Thr Val Pro Thr Thr Val Asp Val Leu His Lys Leu Leu Phe Lys
            35                  40                  45

Asp Thr Leu Pro Thr Gln Gln Ala Asn Asn Gly Thr Thr Lys Pro Asp
        50                  55                  60

Phe Ser Gln Ala Asp Val Pro Leu Asn Gly Val Thr Phe Thr Val Tyr
65                  70                  75                  80

Asp Val Thr Ala Asp Phe Trp Gln Leu Val Ser Lys Asn Gly Gly Ala
                85                  90                  95

Ile Glu Val Ala Gln Thr Thr Leu Ser Gln Asp Ser Tyr Gln Pro Ala
            100                 105                 110

Ser Ser Ser Leu Ile Ala Gln Val Val Thr Ala Gly Gln Gly Glu Ala
        115                 120                 125

Tyr Phe Gly Asp Leu Pro Leu Arg Gln Gly Gln His Ala Ala Val Tyr
130                 135                 140

Leu Phe Lys Glu Thr Ala Ala Pro Lys Asn Ile Glu Ala Ser Gln Asn
145                 150                 155                 160

Leu Val Val Val Met Ser Ser Asn Leu Gln His Gly Asn Gln Ser Arg
                165                 170                 175

Ile Asp Leu Phe Pro Lys Asn Lys Met Val Ser Arg His Thr Asp Ala
            180                 185                 190

Pro Lys Lys Val Pro Lys Lys Ile Arg Gln Leu Leu Pro Gln Thr Gly
        195                 200                 205

Asp Thr Val Ala Ala Trp Leu Ser Val Leu Gly Leu Ile Ile Phe Ala
210                 215                 220

Thr Val Leu Ala Phe Asn Ile Lys Asn Gln Lys Ile Asn Lys Trp Glu
225                 230                 235                 240

Arg

<210> SEQ ID NO 4
<211> LENGTH: 895
<212> TYPE: PRT
<213> ORGANISM: Lactobacillus rhamnosus

<400> SEQUENCE: 4

Met Thr Ala Lys Val Ala Arg Thr Gly His Leu Phe Ala Val Leu Leu
1               5                   10                  15

Ile Leu Met Ser Met Leu Thr Gly Leu Val Thr Ser Gly Ser Ser Val
                20                  25                  30

Val Thr Ala Thr Asp Asn Ile Arg Pro Thr Tyr Gln Thr Asp Ala Asn
            35                  40                  45
```

```
Gly Thr Tyr Pro Thr Asn Ser Trp Gln Val Thr Gly Gln Gln Asn Val
 50                  55                  60

Ile Asn Gln Arg Gly Asp Gln Val Ser Gly Trp Asp Asn Asn Thr
 65                  70                  75                  80

Ile Trp Asn Gly Asp Ala Thr Asp Thr Asn Ser Tyr Leu Lys Phe
                     85                  90                  95

Gly Asp Pro Asn Asn Pro Asp Tyr Gln Ile Arg Lys Tyr Ala Lys Glu
                100                 105                 110

Thr Asn Thr Pro Gly Leu Tyr Asp Val Tyr Leu Asn Val Lys Gly Asn
            115                 120                 125

Lys Gln Gln Asn Val Lys Pro Val Asp Ile Val Leu Val Val Asp Met
130                 135                 140

Ser Gly Ser Met Glu Ser Asn Arg Trp Gly Thr Asn Arg Ala Gly Ala
145                 150                 155                 160

Val Arg Thr Gly Val Lys Asn Phe Leu Thr Ser Ile Gln Asn Ala Gly
                165                 170                 175

Leu Gly Asn Tyr Val Asn Val Gly Leu Ile Gly Phe Ser Ser Pro Gly
                180                 185                 190

Tyr Ile Gly Gly Lys Ser Gly Tyr Ile Ser Val Lys Leu Gly Lys Ala
                195                 200                 205

Gly Asn Ala Ser Gln Gln Ala Ile Asn Gly Ala Leu Ser Pro Arg
210                 215                 220

Phe Gln Gly Gly Thr Tyr Thr Gln Ile Gly Leu Arg Gln Gly Ser Ala
225                 230                 235                 240

Met Leu Asn Ala Asp Thr Ser Gly Asn Lys Lys Met Met Ile Leu Leu
                245                 250                 255

Thr Asp Gly Val Pro Thr Phe Ser Asn Glu Val Ile Asn Ser Glu Trp
                260                 265                 270

Ile Asn Gly Thr Leu Tyr Gly Thr Asn Phe Gly Ser Ser Arg Asp Glu
                275                 280                 285

Pro Gly Asn Thr Ala Arg Leu Arg Trp Pro Tyr Thr Asp Ser Ser Gly
            290                 295                 300

His Tyr Ile Tyr Asp Thr Trp Pro Ala Thr Leu Gly Glu Ala Lys Ile
305                 310                 315                 320

Ala Lys Asp Ser Gly Asn Glu Val His Ala Leu Gly Ile Gln Leu Ala
                325                 330                 335

Asp Asp Asp His Tyr Met Thr Lys Glu Lys Ile Arg Gln Asn Met Gln
                340                 345                 350

Leu Ile Thr Asn Ser Pro Asp Leu Tyr Glu Asp Ala Asp Ser Ala Asp
                355                 360                 365

Ala Val Glu Ala Tyr Leu Asn Asn Gln Ala Lys Asp Ile Ile Lys Asn
370                 375                 380

Phe Asn Thr Val Thr Asp Gly Thr Ile Thr Asp Pro Ile Gly Thr Gln
385                 390                 395                 400

Phe Gln Tyr Ala Asn Asn Gln Ala Thr Val Thr Ser Val Gly Lys Gln
                405                 410                 415

Thr Val Pro Ala Ser Glu Leu Pro Ser Ala Ala Ile Gln Asp Gly Gln
                420                 425                 430

Leu Thr Val Asn His Met Asn Leu Gly Gln Asp Gln Glu Val Gln Ile
                435                 440                 445

His Tyr Gln Val Arg Ile Lys Thr Glu Asp Ala Gly Phe Lys Pro Asp
                450                 455                 460

Phe Trp Tyr Gln Met Asn Gly Glu Thr Leu Leu Thr Pro Lys Ala Gly
465                 470                 475                 480
```

-continued

```
Ala Ala Ala Val Asp Phe Gly Ile Pro Ser Gly Arg Ala Pro Ala Thr
            485                 490                 495
Thr Val Tyr Val Gln Lys Gln Trp Arg Gln Leu Ser Asn Gln Ser Leu
            500                 505                 510
Pro Asp Thr Leu Asn Val Thr Val Gln Arg Lys Val Ala Asp Gly Ser
            515                 520                 525
Leu Asp Pro Asn Trp Gln Gln Thr Leu Val Leu Lys Lys Ala Asp Asn
            530                 535                 540
Trp Lys Ala Ser Phe Thr Ala Pro Ala Tyr Asn Asn Gln Gly Gln Ser
545                 550                 555                 560
Phe Ser Tyr Val Val Lys Ser Glu Asp Ala Ser Gly Ile Asp Leu Ser
                565                 570                 575
Ser Phe Ile Ser Ser Gln Asn Met Asp Gln Gln Thr Ala Thr Leu Thr
            580                 585                 590
Leu Thr Asn Gln Gln Tyr Gly Phe Gln Phe Gln Lys Lys Thr Thr Asp
            595                 600                 605
Gly Thr Asp Leu Ser Ala Asp Gln Leu Lys Ala Met Gln Phe Asn Leu
            610                 615                 620
Thr Gln Tyr Ser Asp Asn Ser Phe Gln Gln Ala Ser Lys Thr Asn Ala
625                 630                 635                 640
Ile Thr Ser Thr Asp Leu Gln Ala Leu Ala Pro Gly Tyr Tyr Gly Ile
                645                 650                 655
Gln Glu Ala Ala Ala Pro Thr Gly Tyr Gln Leu Asp Gly Thr Thr Tyr
            660                 665                 670
Leu Phe Gln Leu Thr Ser Asp Gly Gln Trp Gln Tyr His Gly Thr Lys
            675                 680                 685
Asp Asn Val Thr Ser Gly Ser Val Ile Asn Gly Gln Gln Thr Leu Asn
            690                 695                 700
Pro Val Gly Asp Lys Ser Asp Asp Phe Thr Val Thr Gly Asp His Gln
705                 710                 715                 720
Gln Ile Leu Thr Leu Thr Lys Tyr Asp Glu Pro Lys Pro Ser Met Thr
                725                 730                 735
Leu Arg Val Ile Lys Gln Asp Asn Gln Ser Gln Tyr Leu Ala Gly Ala
            740                 745                 750
Ala Phe Thr Leu Gln Pro Ser Ala Gly Glu Ala Glu Thr Ile Thr Ser
            755                 760                 765
Ser Ala Thr Ser Glu Gly Gln Ala Phe Ala Thr Lys Leu Val Ala Asp
770                 775                 780
Gly Thr Tyr Thr Met Ser Glu Thr Lys Ala Pro Asp Gly Tyr Gln Ser
785                 790                 795                 800
Asn Pro Ala Lys Ile Ala Ile Gln Val Ala Thr Gly Lys Glu Ala
                805                 810                 815
Thr Val Thr Ile Asp Gly Glu Ala Leu Lys Pro Gly Glu Ser Lys Asn
            820                 825                 830
Gly Tyr Thr Leu Ala Ile Asp Gly Ser Thr Ile Thr Leu Gln Ala Ile
            835                 840                 845
Asn Gln Pro Leu Ala Ile Leu Pro His Thr Gly Gly Gln Gly Tyr Gln
            850                 855                 860
Arg Leu Leu Gly Ile Ala Leu Gly Leu Ile Ser Ala Ala Phe Leu Leu
865                 870                 875                 880
Leu Leu Val Val Leu Ile Lys Arg Arg Val Val Lys Gln His Asp
                885                 890                 895
```

```
<210> SEQ ID NO 5
<211> LENGTH: 274
<212> TYPE: PRT
<213> ORGANISM: Lactobacillus rhamnosus

<400> SEQUENCE: 5

Met Thr Lys Lys Ala Ser Gly Thr Ser Arg Leu Leu Arg Trp Phe Val
1               5                   10                  15

Ile Leu Leu Phe Thr Ala Gly Ala Ala Cys Phe Cys Tyr Pro Phe Ala
            20                  25                  30

Ala Thr Ala Ile Asn Glu Leu Leu Thr Ser Arg Arg Ala Ala Ala
        35                  40                  45

Gln Gln Glu Ala Lys Gln Asn Ala Ala Ala Gln Asp Glu Gln Arg Ala
    50                  55                  60

Ala Glu Asn Arg Ala Leu Ala Gln Thr Gly Leu Arg Pro Gly Gln Asp
65                  70                  75                  80

Pro Phe Gln Ser Arg Gln Lys Phe Asn Gln Ala Tyr Val Lys Arg His
                85                  90                  95

Leu Ile Gly Arg Val Val Ile Pro Lys Leu Ala Val Asp Leu Pro Leu
            100                 105                 110

Phe Asp Thr Thr Asn Asn Thr Leu Leu Asp Gln Gly Ala Val Val Leu
        115                 120                 125

Pro Gly Thr Ser Tyr Pro Arg Gly Gly Lys Asn Thr His Thr Val Val
130                 135                 140

Ser Ala His Gly Gly Leu Pro Thr Lys Arg Phe Phe Thr Asp Leu Ser
145                 150                 155                 160

Lys Leu Lys Arg Gly Gln Lys Phe Phe Leu Gln Val Asn Gly Lys Lys
                165                 170                 175

Met Ala Tyr Gln Val Phe Arg Ile Lys Thr Val Arg Pro Asp Glu Thr
            180                 185                 190

Gln Ser Leu Arg Ile Glu Pro Gly Arg Asp Leu Ala Thr Leu Met Thr
        195                 200                 205

Cys Thr Pro Tyr Met Ile Asn Ser His Arg Leu Leu Val Thr Gly Lys
210                 215                 220

Arg Val Pro Tyr Thr Glu Ser Leu Glu His Ala Ala Glu Ser Ala Asp
225                 230                 235                 240

Arg Trp Arg Leu Trp Leu Ser Ile Ala Val Val Val Gly Val Leu Gly
                245                 250                 255

Leu Ala Leu Leu Ser Phe Tyr Leu Ala Arg Arg Tyr Leu Arg Arg Pro
            260                 265                 270

Arg Ala

<210> SEQ ID NO 6
<211> LENGTH: 517
<212> TYPE: PRT
<213> ORGANISM: Lactobacillus rhamnosus

<400> SEQUENCE: 6

Met Gln Val Thr Phe Lys Lys Ile Gly His Ser Leu Leu Ala Ala Leu
1               5                   10                  15

Met Leu Met Ser Phe Leu Leu Pro Leu Leu Ser Ala Gly Lys Pro Val
            20                  25                  30

His Ala Ala Thr Thr Thr Val Asp Phe Thr Leu His Lys Ile Glu Gln
        35                  40                  45

Thr Ser Asp Glu Gln Ile Gln Asn Thr Gly His Asp Leu Gly Leu Thr
    50                  55                  60
```

-continued

```
Gly Arg Lys Pro Val Gln Gly Ala Gln Phe Lys Ile Phe Asn Val Thr
 65                  70                  75                  80

Asp Ala Phe Tyr Gln Leu Leu Glu Asn His Asp Lys Thr Thr Ala Ala
                 85                  90                  95

Ser Met Ile Ser Gln Asn Leu Gly Gln Tyr Val Asn Leu Gln Asp Pro
            100                 105                 110

Asn Ala Ala Thr Val Thr Thr Asp Ala Asp Gly Leu Ala Ala Phe Lys
        115                 120                 125

Gly Leu Ala Ala Lys Thr Asn Gly Arg His Ser Val Tyr Ala Phe His
    130                 135                 140

Glu Ala Val Thr Pro Gln Pro Tyr Gln Lys Ala Ala Asp Met Ile Val
145                 150                 155                 160

Ser Leu Pro Val Arg Gln Asp Asp Gly Ser Asp Leu Thr Asn Ile His
                165                 170                 175

Leu Tyr Pro Lys Asp Ser Leu Val Thr Lys Asn Leu Thr Glu Ile Asn
            180                 185                 190

Glu Gln Ala Val Ala Thr Lys Asp Leu His Asp Val Ala Val Gly Asp
        195                 200                 205

Val Leu Thr Tyr Gln Val Gln Phe Gln Ile Pro His Asp Ile Gly Ala
    210                 215                 220

Leu Ala Asp His Ser Gln Asp Thr Phe Lys Tyr Asn Gln Phe Lys Val
225                 230                 235                 240

Leu Asp Tyr Met Thr Lys Glu Gly Leu Thr Phe Lys Ala Leu Thr Ala
                245                 250                 255

Ile Thr Val Asp Gly Gln Asp Ile Leu Lys Ala Leu Thr Gly Lys Met
            260                 265                 270

Ala Phe Met Ser Ser Asn Asp Ala Ala Trp Gln Gln Thr His Asn Tyr
        275                 280                 285

Pro Phe Gly Phe Glu Leu Asp Phe Leu Gly Gly Thr Asp Pro Asp Ala
    290                 295                 300

Val Arg Asn Leu Leu Thr Gln Tyr Ala Gly Lys Arg Val Thr Val Ala
305                 310                 315                 320

Tyr Thr Gly Ile Val Asn Glu Lys Met Ile Pro Asp Gln Lys Val Gly
                325                 330                 335

Asn Thr Ala Glu Val Ser Phe Asp Pro Asp Ser Lys Ile Thr Val Asn
            340                 345                 350

Gly Pro Glu Ile Gln Thr Gly Gly Ile Arg Phe Phe Lys His Glu Ala
        355                 360                 365

Gly Ser Ser Lys Ser Leu Ala Asn Ala Thr Phe Ile Leu Gln Arg Met
    370                 375                 380

Asn Gly Asn Val Arg Glu Tyr Ala Val Leu Glu Gly Val Asn Gly Met
385                 390                 395                 400

Ala Gly Thr Tyr Gln Pro Thr Lys Ile Thr Trp Thr Thr Asn Gln Asp
                405                 410                 415

Ala Ala Thr Arg Leu Lys Thr Ser Gly Ala Glu Thr Ala Asn Leu Thr
            420                 425                 430

Ile Gln Gly Leu Leu Pro Gly Arg Tyr Thr Leu Val Glu Thr Ala Ala
        435                 440                 445

Pro Glu Gly Tyr Glu Ile Leu Asp Pro Thr Thr Asp Phe Glu Val Ile
    450                 455                 460

Ala Gly Thr Trp Gly Thr Lys Thr Ile Arg Ile Ala Asn Thr Pro Val
465                 470                 475                 480

Asn Gln Leu Leu Pro Met Thr Gly Gly Ile Gly Leu Phe Ala Phe Leu
                485                 490                 495
```

```
Met Ile Gly Ala Ile Leu Met Gly Gly Gly His Leu Met Lys Lys Lys
              500                 505                 510

Thr Ser Lys Lys Val
              515

<210> SEQ ID NO 7
<211> LENGTH: 451
<212> TYPE: PRT
<213> ORGANISM: Lactobacillus rhamnosus

<400> SEQUENCE: 7

Met Arg Arg Phe Tyr Trp Trp Leu Val Pro Leu Leu Leu Leu Ile Gly
 1               5                  10                  15

Ile Val Leu Gly Asn Thr Pro His Trp Val His Ala Ala Asp Gln Thr
             20                  25                  30

Ala Glu Ile Val Ile His Lys Arg Ile Tyr Arg Asp Ile Arg Gln Pro
         35                  40                  45

Glu Asp Val Trp Tyr Glu Asn Asp Gly His Arg Ile Asp Pro Asn Asn
     50                  55                  60

Pro Asp Lys Asp Gly Tyr Lys Leu Leu Ser Lys Thr Ser Gly Leu Asn
 65                  70                  75                  80

Gly Ala Asn Phe Glu Val Tyr Asp Ala Ser Ser Leu Leu Lys Pro Asn
                 85                  90                  95

Met Thr Pro Glu Ala Ile Arg Ala Leu Val Asp Arg Tyr Gln Asn Met
            100                 105                 110

Thr Arg Lys Gln Ala Leu Lys Phe Ala Arg Ala Asn Leu Lys Leu Ala
        115                 120                 125

Gly Gln Gly Asn Lys Gly Ile Gly Leu Met Asn Thr Lys Asn Asp Pro
    130                 135                 140

Thr Leu Gly Glu Asp Gly Ile Ser Arg Ile Thr Val Ser Val Asp Gln
145                 150                 155                 160

Gln Ala Pro Thr Lys Ala Tyr Leu Met Ile Glu Val Ala Pro Asp Pro
                165                 170                 175

Ser Thr Glu Leu Asn Val Asp Leu Glu Arg Lys Ser Ser Pro Met Leu
            180                 185                 190

Val Val Phe Pro Val Thr Asp Pro Ile Ser Gly Asn Pro Leu Gln Thr
        195                 200                 205

Ile His Leu Tyr Pro Lys Asn Val Gly Tyr Val Arg Asp Pro Tyr Phe
    210                 215                 220

Phe Lys Phe Gly Val His Pro Asp Gly Thr Ser Lys Arg Leu Ala Gly
225                 230                 235                 240

Ala Ile Phe Ala Ile Tyr Arg Ile Glu Asn Gly Lys Lys Leu Tyr Leu
                245                 250                 255

Asp Met Ser Pro Val Thr Asp Leu Arg Asn Lys Trp Val Ser Thr Thr
            260                 265                 270

Asp Pro Leu His Asp Asp Arg Val Asn Lys Phe Val Ser Asp Gln Asp
        275                 280                 285

Gly Leu Val Asn Thr Gly Glu Arg Phe Leu Pro Ala Gly Glu Tyr Phe
    290                 295                 300

Phe Glu Glu Leu Gln Gly Val Pro Gly Tyr Glu Val Asp Ala Lys Ser
305                 310                 315                 320

Arg Ala Ile Lys Ile Glu Ile Pro Asp Ser Trp Glu Asp Glu Asp Gly
                325                 330                 335

Asn Arg Arg Phe Val Leu Ile Asp Gly Gln Pro Met Gln Glu Asn Phe
            340                 345                 350
```

```
Gly Gly Val Val Thr Pro Glu Met Ile Ser Ser Gly Tyr Pro Arg Val
            355                 360                 365

Tyr Asn Tyr Ala Asp Lys Gln Ala Ser Thr Thr Gly Asp Gln Thr Ala
            370                 375                 380

Gly Pro Ser Thr Thr Gln Leu Gly Asn His Gly Gln Asp Thr Asn Gly
385                 390                 395                 400

Thr Gly Thr Arg Thr Pro Lys Arg Gln Ser Gly Tyr Leu Pro Ala Met
                405                 410                 415

Ser Asp Trp Arg Asn Leu Arg Phe Val Leu Leu Gly Ser Leu Leu Leu
                420                 425                 430

Leu Leu Ala Thr Tyr Phe Phe Ile Lys Asn Lys Lys Ala Arg His His
            435                 440                 445

Ala Cys Lys
    450

<210> SEQ ID NO 8
<211> LENGTH: 983
<212> TYPE: PRT
<213> ORGANISM: Lactobacillus rhamnosus

<400> SEQUENCE: 8

Met Pro Arg Lys Trp Ile His Met Leu Met Leu Leu Met Leu Val
1               5                   10                  15

Thr Gln Ile Gly Ser Ala Ala Val Pro Val Ala Lys Ser Ala Gln Thr
                20                  25                  30

Asn Pro Lys His Asp Val Arg Asp Ala Ser Val Gln Pro Ser Thr Arg
            35                  40                  45

Pro Ala Ala Ser Glu Ala Ala Glu Phe Asp Leu Glu Ala Ala Ala Ser
        50                  55                  60

Ala Pro Ser Thr Ser Ala Ala Lys Gln Thr Thr Ser Lys Ala Arg
65                  70                  75                  80

Gln His Ile Lys Leu Glu Ala Gly Lys Ser Trp His Gly Asp Gly His
                85                  90                  95

Thr Leu Thr Tyr Asn Val Asp Ile Gln Arg Ser Glu Ile Gln Val Lys
            100                 105                 110

Leu Ile Leu Ala Lys Pro Gln Asp Gln Thr Gly Gln Gln Val Val Lys
        115                 120                 125

Phe Ala Asn Ala Gln Gly Phe Thr Ser Gln Pro Ala His Thr Asn Gly
    130                 135                 140

Glu Ile Thr Arg Arg Leu Ala Glu Lys Thr Ala Glu Lys Gly Glu Tyr
145                 150                 155                 160

Leu Leu Thr Lys Lys Leu Pro Asp Thr Lys Gln Gln Ala Ala Ser Val
                165                 170                 175

Lys Leu Ser Leu Asp Gly Phe Asn Asp Ala Ala Gln Val Leu Ala Leu
            180                 185                 190

Asp Val Asp Leu Gln Leu Pro Ala Arg Leu Ala Asn Asp Val Gln
        195                 200                 205

Glu Pro Ala Ala Leu Ser Lys Asp Ala His Ser Leu Ile Leu Pro Pro
    210                 215                 220

Ser Ala Leu Gly Thr Ile Lys Ile His Ala Thr Lys Ala Asp Gly Ala
225                 230                 235                 240

Ala Leu Ser Asp Glu Glu Ala Gln Ile Tyr Arg Lys Pro Asn Ser Ser
                245                 250                 255

Thr Arg Ser Lys Tyr Gly Ser Arg Trp Ala Met Glu Asn Gly Val Ser
            260                 265                 270
```

-continued

```
Ser Asp Tyr Val Ser Arg Ser Asp Ala Thr Ala Ile Ile Phe Lys Asp
        275                 280                 285

Ala Val Gln Asn Pro Ser Gly Pro Ser Asn Leu Leu Asp Ala Lys Ile
        290                 295                 300

Lys Val Asp Ile Asp His Val Gly Ser Ala Ser Asp Leu Asp Gly Asn
305                 310                 315                 320

Arg Phe Glu Ile Gly Ala Tyr Val Glu Leu Thr Gly Ile Arg Val Arg
                325                 330                 335

Pro Val Glu Trp Gly Thr Thr Pro Gln Asp Val Gly Ile Asp Phe Ser
                340                 345                 350

Asn Asn Phe Phe Ser Gly Met Ser Phe Ala Asn Val Leu Tyr Tyr Asp
            355                 360                 365

Trp Arg Val Ile Phe Tyr Asp Lys Ala Thr Arg Gln Arg Leu Asn Phe
        370                 375                 380

Ile Pro Gln Ser Glu Ala Asn Gln Asn Ser Thr Leu Thr Phe Thr Ser
385                 390                 395                 400

Leu Asn Pro Gly Glu Phe Val Trp Thr Glu Ala Gly Met Thr Pro
                405                 410                 415

Thr Tyr Asp Asp Arg Phe Ile Thr Asp Trp Gln Phe Glu Glu Gly Thr
                420                 425                 430

Trp Ile Thr Ser Asp Lys Ala Thr Phe Glu Thr Glu Lys Leu Gly Ala
            435                 440                 445

Arg Gly Lys Glu Gln Arg Gly Tyr Thr Ser Gln Thr Trp Gly Asn Trp
        450                 455                 460

Val Asp Pro Ile Asp His Glu Asn Met Thr Glu Trp Glu Asp Arg Leu
465                 470                 475                 480

Gly Ala Pro Thr Phe Gly Arg Gly Ala Val Ala Phe Thr Leu Asn Gly
                485                 490                 495

Thr Ser His Thr Phe Arg Arg Gly Thr Tyr Ser Asn Gly Gly Gly Thr
            500                 505                 510

Trp Val Ala Asn Gly Ser Gly Gln Ile Glu Leu Ile Asp Pro Asn Val
        515                 520                 525

Thr Asn Asn Lys Ser Val Ser Ala Asn Ala Glu Ala Gly Gly Gly Ala
        530                 535                 540

Glu Glu Asp Lys Thr Gly Thr Ile Trp Thr Ala Asn Asp Leu Asp Asp
545                 550                 555                 560

Gln Val Val Asn Gln His Tyr Asn Gly Glu Pro Phe Tyr Tyr Tyr Ile
                565                 570                 575

Asn Gln Glu Val Tyr Ser Met Gly Asp Tyr Val Val Lys Pro Thr Lys
            580                 585                 590

Ile Val Val Thr Asp Leu Leu Pro Glu His Val Glu Leu Ile Pro Asp
        595                 600                 605

Asn Asn Asn Ser Pro Pro Thr Tyr Gln Lys Ala Phe Gln Leu Phe Asn
610                 615                 620

Ala Thr Asp Pro Asp Ala Val Gly Gln Asp Arg Lys Met Thr Leu Thr
625                 630                 635                 640

Glu Asp Val Ser Asp Phe Val Thr Gln Glu Gly Asp Arg Gln Arg
                645                 650                 655

Ile Thr Leu Thr Ile Gly Arg Glu Asp Val Gln Lys Ile His Phe His
            660                 665                 670

Ser Gly Phe Phe Ser Leu Arg Leu Lys Val Arg Pro Thr Lys Asp Pro
        675                 680                 685

Asp Thr Leu Thr Lys Arg Leu Thr Leu Val Asn Lys Ala Thr Val Lys
```

```
                    690                 695                  700
Phe Phe Asp Thr Glu Glu Arg Tyr Ser Lys Glu Thr Asn Ala Val Gln
705                 710                 715                  720

Val His Leu Asp Pro Ala Gly Arg Phe Pro Ala Glu Phe Thr Lys Lys
                725                 730                 735

Asn Gln Tyr Gly Ala Val Leu Pro Gly Ser Arg Phe Val Leu Lys Gln
            740                 745                 750

Gly Asp Thr Gln Leu Gln Thr Ala Thr Ala Asp Ser Gln Gly Lys Val
        755                 760                 765

Ser Phe Gly Thr Leu Lys Pro Gly Asp Tyr Gln Val Ser Glu Ile Ala
    770                 775                 780

Ala Ala Gly His Glu Leu Gln Ala Glu Phe Asp Leu Lys Val Ala Ala
785                 790                 795                  800

Asp Gly Thr Val Thr Val Gly Arg Asn Gly Glu Ile Trp Pro Asp Thr
                805                 810                 815

Thr Val Ile Asn Gln Leu Lys Pro Thr Glu Leu Glu Leu Ile Lys Ile
            820                 825                 830

Glu Lys Gly Lys Asn Lys Leu Ala Asn Ala Ser Phe Ala Leu Tyr Arg
        835                 840                 845

Gly Asp Gln Thr Thr Pro Val Ala Gln Gly Thr Thr Asp Glu Asn Gly
    850                 855                 860

Gln Leu Arg Phe Thr His Gln Leu Thr Pro Gly Thr Tyr Arg Leu Thr
865                 870                 875                  880

Glu Thr Lys Ala Pro Ala Gly Phe Asp Arg Leu Asn Gly Ser Phe Thr
                885                 890                 895

Phe Lys Ile Asn Ala His Gly Thr Met Val Asp Leu Ala Tyr Ser Gly
            900                 905                 910

Ser Asp Leu Ser Ser Asp Glu Tyr Gly Phe Glu Phe Ile Pro Asp Ala
        915                 920                 925

Glu Asp Lys Leu Asn Arg Ile Arg Phe Thr Leu Thr Asn His Ser Leu
    930                 935                 940

Glu Thr Leu Leu Pro Lys Thr Gly Gly Ser Gly Ile Leu Leu Phe Leu
945                 950                 955                  960

Met Val Ala Ile Ser Ala Cys Gly Gly Gly Trp Leu Leu Tyr Leu Tyr
                965                 970                 975

Leu Lys Arg Lys Glu Ala Arg
            980

<210> SEQ ID NO 9
<211> LENGTH: 1080
<212> TYPE: DNA
<213> ORGANISM: Lactobacillus rhamnosus

<400> SEQUENCE: 9
gtgacaaaac gaacacgtcg acctttagac ttgattgata ttgtgattgg atgtcttctt      60
ttagcgggtt ttggtgtttt atgctatcca tttgcaagtg atgcttacgt ttcttaccaa     120
aatcagcaag tcatcgacag gtatcgacaa caagaagcgc ggaagaatca gatggtgttg     180
cggcgggaat ataacgacta tcagcaaaaa aataaacagt tggcagcaag tcaacaagtg     240
cccggcgttg ccagttttaa tcatgctgtt aatgatcaag gaccgcaaa acagcagcc      300 aaacgcaatc aacaaatctt gactcggcag acagttgctc agttgacgat tcccaaaatt     360
ggccttagtc tgccggtttt tgatcataca agcgattggc ttctacaatt ggcgcctgt      420 ttattggatg gtacaagtta tccaactggt ggtaaaaata cccatgctgt catttcagcg     480
```

| | |
|---|---|
| catcgtggtg tgccaaacgc tgaactttt acccgagtac cagcgttaaa aaaaggcgac | 540 |
| aagttttta ttagcatagg caatcataaa ttggcttacc aagtctttaa gcgccaggtt | 600 |
| attgagccaa gtgatacccg gcagctaaga attgtgccgg acaggatct tgtgaccta | 660 |
| atgacctgca cgcctatat gatcaattct catcgattgt tgataacggg tcgccgaatt | 720 |
| ccttacgtta aggcagatga agaggcttca agttgggcgg tttggtggaa caaattaaag | 780 |
| ctaatagtcg cacttttagg cgcggtgatc attttaggcg tgatcggttt cgtaatgcgc | 840 |
| agtttgatgc ttggccgaaa gcattatttg ctggaagtac cggctgaagc cacacaagtc | 900 |
| gtggtgaaac gaggtcgaca tatacattct ttaaatcag atcaaactgg ggtgactgac | 960 |
| atcagcctgc ctggtaatca ttatcgagtc gcaattgtca caccgcttgg ccggactaag | 1020 |
| tacaaggctt atgtcaaaaa aattcgggat aaaagctttc aattaaaaga atatcattaa | 1080 |

<210> SEQ ID NO 10
<211> LENGTH: 1005
<212> TYPE: DNA
<213> ORGANISM: Lactobacillus rhamnosus

<400> SEQUENCE: 10

| | |
|---|---|
| atgaaaaga caattgccaa gaaagtgctg acattaacca gcacgatcct aatgacatta | 60 |
| ctgatggttc tcgggtttaa tggcactcgg gttcaagcag atacgaatga tacgacaaca | 120 |
| caaaacgttg tccttactaa atacgggttt gacaaagatg ttactgccat tgatcgtgcg | 180 |
| actgatcaaa tttggaccgg cgatggtgct aagccttac aaggcgttga tttcaccatt | 240 |
| tacaacgtga cagccaatta ttgggcatcg cctaaggatt ataaaggcag ttttgatagt | 300 |
| gctccggttg ccgcaaccgg tacgactaat gacaaggggc aactaaccca agcattacct | 360 |
| atccaatcaa aagatgccag tggtaagact cgtgctgctg tctatctttt ccatgaaacc | 420 |
| aatccgcgag ctggttataa cacgtctgcc gatttctggt taaccttacc agccaaggca | 480 |
| gcagccgacg ggaatgtcta tgtctaccca agaatgttc aaaagaccac ctatgagcgc | 540 |
| acttttgtta agaaagatgc tgagactaaa gaagtgcttg aaggagccgg ctttaagatt | 600 |
| agcaatagtg atggcaagtt tttgaagttg acagataaag atggtcaaag cgtcagcatc | 660 |
| ggcgaaggat ttatcgatgt attggccaat aactatcgat tgacgtgggt tgctgaaagc | 720 |
| gatgctactg ttttcacgtc tgataagagc ggtaagtttg gcttaaatgg atttgctgat | 780 |
| aacaccacaa cttacacggc agttgaaaca aacgtgccgg atggttatga tgctgctgcc | 840 |
| aatacagact ttaaagctga taattcgtct agcgacattc tagatgcacc aagcggtatt | 900 |
| ctgccacaca ctggtggtac tggcacagtc attttttgcga ttttgggcgt tgccttaatt | 960 |
| gcatttggag cagttgccta tcgcaagcgc cgcaatggtt tctaa | 1005 |

<210> SEQ ID NO 11
<211> LENGTH: 726
<212> TYPE: DNA
<213> ORGANISM: Lactobacillus rhamnosus

<400> SEQUENCE: 11

| | |
|---|---|
| atgactaaat ccttccgtcc gttagtgatt ttgaccttt gcttggcact actagtcagt | 60 |
| ttggcaacga caacgttgca gcagacacag gcggcaactg tgccgaccac tgttgatgtt | 120 |
| gtgttgcata agctgttgtt taaagatacc ttgccaactc aacaagcaaa taacgggaca | 180 |
| acaaaacccg acttttcgca ggcagatgtg ccgttaaacg gtgtgacgtt cacagtttat | 240 |
| gacgtgaccg ctgactttg gcagcttgtc tccaaaaatg gcggtgcgat tgaggtagca | 300 |

```
caaacgacgt tgagtcaaga tagctatcag cctgctagct ccagccttat cgcacaggtt     360
gtgacggctg gtcagggaga agcgtacttt ggcgatttac cactccgaca ggggcagcat     420
gctgcggttt atcttttaa agaaacggcg gcacctaaga atattgaagc cagtcagaat      480
cttgtggttg tcatgtcaag caaccttcaa catgggaatc aatcacgcat tgatttattt     540
cctaagaaca aaatggtaag tcgtcacacc gatgcccca aaaagttcc aaagaaaata      600 cgtcaattgt tgccacaaac gggtgataca gttgcagctt ggctttcagt gctcgggttg     660
ataatcttcg cgacagtact tgcttttaac ataaaaaacc aaaaaattaa taagtgggag    720
agataa                                                              726
```

```
<210> SEQ ID NO 12
<211> LENGTH: 2688
<212> TYPE: DNA
<213> ORGANISM: Lactobacillus rhamnosus

<400> SEQUENCE: 12
atgacagcta aagtggcgag aactgggcat tgttcgcgg tcttattgat tttgatgagt      60
atgttaacag gctagtgac aagtggcagt tcagttgtga cagccactga taacattcgc     120
ccaacctatc aaaccgatgc taatggtacc tatccgacaa attcgtggca ggtcacggga     180
caacaaaatg taatcaatca acgtggcggg gatcaagttt cagggtggga taataataca    240
atatggaatg gtgatgcgac tgataccacg aactcttacc tgaaatttgg tgaccccaat    300
aatccggatt atcagattcg aaaatatgct aagagacga ataccctgg attgtacgac      360 gtttatttga acgtcaaagg caataaacag caaaatgtga agcctgtaga tattgtctta    420
gttgttgata tgtctgggtc aatggagtca aacagatggg gcacgaatcg agctggtgct    480
gttcgtactg gcgttaagaa tttcttgact tctattcaaa acgccggtct gggtaattac    540
gtcaatgttg gtttaattgg gttttctagt cctggttata tcggtggcaa atcgggttat    600
attagtgtca aattaggcaa agcaggtaat gccagccagc aacaagcgat taatggtgca    660
ttgagtccaa ggtttcaagg gggtacgtat acgcagattg gtttgcggca aggatcagcc    720
atgctgaatg cggacaccag tggcaataaa aaaatgatga tttttgttaac tgatggcgtg    780 ccgacttttt ctaacgaggt gataaaattca gagtggataa atggtacatt gtatggcact    840
aattttggat ccagcagaga tgaaccaggg aacaccgcac gacttcgatg ccatacacc     900 gatagttcag gtcattatat atatgatact tggccagcaa cattgggtga ggccaagata    960
gcaaaggata gtggtaatga ggtgcacgcg ttaggcatcc aactggctga cgacgaccac   1020
tacatgacga agaaaaaat acgccaaaac atgcagctta ttaccaattc accggattta   1080
tacgaagatg ctgatagtgc cgatgctgtt gaggcttatt tgaacaatca ggcaaaggac   1140
attatcaaaa actttaatac tgtcaccgac ggcacgatca cagacccgat tggtacgcaa   1200
tttcaatatg cgaacaacca ggcgaccgtt acgagtgtcg gcaagcaaac tgtgccagca   1260
agtgagttgc caagtgcggc gatccaagat ggtcaattga cggtgaatca catgaacttg   1320
ggtcaggatc aggaagttca aatccattat caagtacgga tcaaaacaga ggatgctggc   1380
ttcaagcctg atttttggta ccaaatgaat ggtgaaacat tgttgacacc aaaagcgggc   1440
gctgccgctg ttgactttgg gattccttca ggcagggcac cagcaactac agtttatgtg   1500
cagaagcaat ggcgccagtt aagcaatcaa tcgttaccgg atacgctcaa cgtcacggtg   1560
cagcgaaaag tggctgacgg ttcgcttgat ccaaattggc aacagacctt agtccttaaa   1620
aaagctgata actggaaagc tagctttacg gcacctgcgt ataacaatca gggtcaaagt   1680
```

```
ttttcatatg tcgttaagag tgaagatgcc tcgggaattg atttgagttc gtttatcagt    1740
tctcaaaata tggatcagca aacagcaacg ttgactttga caaatcagca gtatggtttt    1800
cagtttcaga aaaaacaac cgatggtact gatttatcag cagatcagtt gaaggccatg    1860
cagtttaact taacccagta cagcgataac agttttcagc aggcatccaa aaccaacgcc    1920
atcacgtcaa cggatctgca ggcactagcg ccagggtatt acggtattca ggaagctgca    1980
gcacctacag gttatcaact tgatgggaca acgtatcttt ttcagctaac gtctgatggg    2040
caatggcaat accatggcac aaaggacaat gtgacatcag ggagtgttat taatggccag    2100
cagactttga atcctgttgg tgataagtca gatgatttta cggtgaccgg ggatcaccag    2160
caaattctga cgctaacgaa atatgatgaa ccaaagccat ccatgacttt gcgggtcatc    2220
aaacaggata tcaaagcca atatcttgca ggtgcagcgt tcaccctgca accaagtgct    2280
ggcgaagctg agacgataac atcatcggcg acatctgagg acaagcgtt tgcgacaaaa    2340 ttagttgcag atggtaccta tacgatgtca gaaacaaaag caccagatgg ctatcaaagc    2400
aatcctgcaa agattgccat tcaggtagct acgactggta agaggcaac cgtcacgatt    2460 gacggtgagg cattgaagcc gggcgaaagt aagaacggat acacattagc gattgatggc    2520
agcacgatca ctttgcaggc gattaatcag ccacttgcaa ttttgccgca tacaggtggt    2580
cagggctatc agcgattgct tggtatcgca ctgggattga tcagcgcagc gttccttta    2640 ttactggttg ttttgataaa gcgacgggtg gtgaagcaac atgactaa                2688

<210> SEQ ID NO 13
<211> LENGTH: 825
<212> TYPE: DNA
<213> ORGANISM: Lactobacillus rhamnosus

<400> SEQUENCE: 13
atgacaaaaa aagcgtcggg gacaagtcgg ctgttacgct ggttcgtcat cttactttt      60 actgcgggag ccgcgtgttt ctgctatccg ttcgcggcaa cggctattaa tgaattgcta    120
ctaaccagtc gccgagcagc agcacagcaa gaagccaagc aaaatgccgc cgcccaagat    180
gagcaacggg cagcggagaa ccgtgcactt gcccagactg gtttgcgtcc gggacaggat    240
ccgtttcaaa gtaggcagaa atttaaccaa gcctatgtga acggcatct gatcgggcga     300 gtggttatcc cgaaattagc ggttgatctg cccctttttg acaccaccaa caacacgctg    360
ttagatcaag gggcagtggt gttaccaggt actagctatc gcggggagg caagaacacg    420 catacagttg tttcggcaca cggcggcttg cccaccaaac gctttttcac cgatctgagc    480
aagttgaaac gagggcagaa gttctttctc caagtcaacg gcaaaaagat ggcgtatcag    540
gtctttcgga tcaaaaccgt gcggccggat gaaacccaga gcttgcgcat tgaaccggga    600
cgcgatttgg ccacattaat gacctgtacc ccgtatatga tcaactccca ccgcctgtta    660
gtgaccggca acgggtacc ttataccgaa tcacttgagc acgccgccga gtctgctgat     720
cgctggcgct tgtggttaag tatcgcggtt gtcgtcggag tgctgggatt ggcattgctg    780
agtttctatc tggctcggcg ctatcttcgc cgaccgcggg cgtaa                    825

<210> SEQ ID NO 14
<211> LENGTH: 1554
<212> TYPE: DNA
<213> ORGANISM: Lactobacillus rhamnosus

<400> SEQUENCE: 14
atgcaagtaa cgtttaaaaa gatcgggcac agtctcttgg cagcgctgat gctcatgagc      60
```

-continued

| | |
|---|---|
| ttccttctac cactgcttag tgcgggcaaa cccgtacatg ccgcgacaac gactgtggat | 120 |
| ttcacgctgc acaaaatcga acaaaccagt gacgaacaga ttcaaaatac cggccacgac | 180 |
| cttggactga ccgggcgtaa accggtgcaa ggcgctcaat ttaaaatttt caacgtgacg | 240 |
| gacgcctttt accaattact ggaaaatcat gataagacaa ccgctgcgag catgatatcg | 300 |
| caaaacctgg gtcagtatgt gaatctccag gatcctaatg cagcaactgt cacgactgat | 360 |
| gcagacggct tggcggcatt caaaggatta gccgccaaaa ccaatggccg gcatagcgtg | 420 |
| tacgcatttc acgaagccgt gaccccgcaa ccgtatcaaa aagcagcaga tatgatcgtg | 480 |
| agtctgccag tgcggcaaga cgatggatcg gatctgacca acattcatct ttatcctaaa | 540 |
| gacagtcttg ttaccaaaaa tctgacggaa atcaatgaac aagcggtggc aacaaaagat | 600 |
| ctccatgatg tcgcggttgg cgatgtgctc acgtatcagg ttcagttcca gattccgcat | 660 |
| gatattggcg cgctggctga tcacagtcaa gacacttttaa agtacaacca atttaaagtg | 720 |
| ctggattata tgaccaagga aggccttact tttaaggcat tgacggcaat cacggttgac | 780 |
| ggtcaggaca ttttaaaggc attaaccgga aaaatggcct tcatgagttc taatgacgca | 840 |
| gcttggcaac aaaacacaca ctatccattc gggtttgaac tggactttct aggcgggacc | 900 |
| gatcccgatg cggtacgaaa cctgttgacc caatatgccg gcaaacgcgt gaccgttgcc | 960 |
| tacaccggaa tcgtcaatga gaaaatgatc ccagaccaaa aagtcggtaa cacggctgaa | 1020 |
| gtgagctttg atcctgacag caagattacc gtcaatggtc cggaaatcca gactggcggg | 1080 |
| attcggttct tcaaacacga agccggatct tccaaaagtt tggccaacgc gactttcatc | 1140 |
| ttacagcgaa tgaacggcaa tgtgcgcgaa tatgcagttc ttgaaggcgt taacggtatg | 1200 |
| gccggaacct accaaccgac caagattacc tggacaacga atcaagacgc ggcaacgaga | 1260 |
| ctcaaaacca gtggagccga gacagccaac ttaaccattc aagggctgtt gccagggcga | 1320 |
| tataccttgg ttgaaaccgc ggcaccagaa ggctatgaaa tccttgatcc gacaacagat | 1380 |
| tttgaagtca ttgccggtac ttggggtacg aaaacgattc gcatcgccaa cacgccggtg | 1440 |
| aatcaattat tgccgatgac aggcggaatc ggactcttcg ccttcctgat gatcggggcc | 1500 |
| atcttaatgg gtggcggtca cctaatgaag aaaaagacca gcaagaaagt ctaa | 1554 |

<210> SEQ ID NO 15
<211> LENGTH: 1356
<212> TYPE: DNA
<213> ORGANISM: Lactobacillus rhamnosus

<400> SEQUENCE: 15

| | |
|---|---|
| atgcgacgat tttattggtg gcttgtcccg ttgcttctat tgattggtat cgtgcttggc | 60 |
| aacacaccac attgggttca cgcggctgat caaactgccg agattgtgat ccataagcga | 120 |
| atttatcggg atattcgcca accggaagac gtttggtatg aaaatgacgg tcatcggatt | 180 |
| gacccgaata acccggataa agatggctac aaattattaa gcaaaaccag cgggctgaat | 240 |
| ggtgctaact ttgaggtcta tgatgccagc tccttattga aaccgaatat gacgcctgaa | 300 |
| gcaattcggg ctttagttga tcgttatcag aatatgacgc gtaagcaagc actgaaattt | 360 |
| gcgcgggcca acctgaaatt agccggtcaa gggaacaaag gtatcgggct gatgaataca | 420 |
| aaaaacgatc caacactcgg tgaagatggg atcagccgaa taccgtttc tgtcgatcaa | 480 |
| caggcaccga ctaaagctta tctgatgatc gaggtggcac cggatccttc aaccgaactc | 540 |
| aatgtggact agagcgcaa aagttcgccg atgttagttg ttttttccagt cacggatcct | 600 |
| atcagtggca acccgttaca gaccatccat ctgtatccga aaaatgtcgg ttatgtccgc | 660 |

```
gatccgtatt tcttcaagtt cggcgtgcac cctgatggta cgagtaaacg gttagccggt        720
gcgatctttg ctatttaccg aattgagaat ggtaagaagc tttatctcga tatgtcgcca        780
gtaaccgact tgcgcaacaa atgggtgagc actactgatc cgttgcatga tgaccgcgtg        840
aacaaatttg tttccgatca agatgggcta gttaatacag gtgaacgctt tttgcccgcc        900
ggagaatatt tctttgaaga attgcaaggc gttcccggct atgaagtgga tgctaaaagc        960
cgcgcgatca aaatcgagat tcctgattct tgggaagacg aagatggcaa ccggcgcttt       1020
gtgttaattg acggccagcc gatgcaggaa aactttggcg gggtggtgac accggaaatg       1080
atcagtagcg gctacccgcg agtttataac tatgccgata agcaggcgtc gacaaccggt       1140
gatcaaaccg cggggccatc aacgacccag cttggcaatc acgggcagga tacgaacggc       1200
accggaacgc gtacacctaa gcgtcaatcc ggttatttgc cggccatgtc cgattggcgc       1260
aatttacgct ttgtcctttt agggagtctg ttactactac tggccactta cttcttcatt       1320
aaaaataaga aagcgaggca ccacgcatgc aagtaa                                 1356

<210> SEQ ID NO 16
<211> LENGTH: 2952
<212> TYPE: DNA
<213> ORGANISM: Lactobacillus rhamnosus

<400> SEQUENCE: 16
ttgcctagga aatggattca tatgctgatg ttactgctga tgctggtcac gcaaattggc         60
agtgccgcgg tcccggtagc caaaagcgct cagactaatc caaagcacga tgtccgggat        120
gcgtcagtgc agccgagcac tcgtcctgcc gcatccgaag ctgctgagtt tgatctggaa        180
gcagcggcta gtcgccatc aaccagcgcg ccgccaagc aaactacttc aaaagctcgg         240
cagcacatca agctagaagc agggaagtct tggcacggcg atggtcatac gttaacttac        300
aacgttgaca ttcagcggtc tgaaattcag gttaagttga ttttagccaa gccacaggat        360
caaacggggc agcaagtcgt caagttcgct aatgcccaag gattcacgtc ccagcctgca        420
catactaacg gtgaaataac gcgccggctt gcagagaaaa cggcagaaaa aggtgaatac        480 ctttttaacca aaaagctgcc tgatacaaag cagcaagcag ctagtgtgaa actcagtctg        540
gatggattta atgacgctgc tcaggtatta gcgcttgatg ttgacttgca gctgcctgcg        600
cgcctggcta acgatgatgt gcaggaaccg gctgcactca gcaaagatgc gcacagtctg        660 atttttaccgc cgtctgcact tgggacgatt aaaattcacg caactaaagc tgatggcgcc        720
gcactttcgg atgaagaggc gcaaatttat cgcaaaccaa atagtagtac ccgttccaaaa       780 tacggatcac gttgggcgat ggagaatggc gtttcatcag attatgtgtc gcgttctgat        840
gccaccgcca ttatttttaa agatgcggtt caaaatccca gtggtccttc taacctgcta        900
gatgccaaga tcaaagtgga tattgatcat gttggctcag caagtgatct tgatggaaac        960
cgttttgaga ttggtgctta tgttgaacta acaggtattc gcgtccgtcc agtcgaatgg       1020
ggcactaccc ctcaggatgt cggcattgat ttttccaaca acttctttc cgggatgtca       1080 tttgccaatg ttttgtacta tgactggcgc gtgatttttt atgacaaggc aacgagacag       1140
cgattgaact ttattccgca aagtgaagcc aatcaaaatt cgaccctgac gtttacttcg       1200
ttgaatcccg gtgagtttgt ctggacgag caggcgggga tgacgcccac ttatgacgat       1260
cggtttatca cggattggca atttgaggaa ggaacctgga ttacctcaga taaagcgaca       1320
ttcgaaaccg aaaaactggg cgctcgcggg aaggaacaac gtgggtacac ctcacagacc       1380
tggggaaact gggtcgatcc aattgatcac gagaatatga cggaatggga agatcgacta       1440
```

-continued

```
ggtgcgccaa catttgggcg tggtgccgtt gcgtttactt taaacggtac cagtcatacc    1500
tttagacgcg gcacttattc caacggcggc ggtacttggg ttgccaatgg gagtggacaa    1560
atcgagttga ttgacccaaa tgtcaccaac aacaaaagcg tgagcgcaaa tgccgaagcc    1620
ggtggcggag ccgaggaaga taaaaccggc accatctgga ccgcaaatga tttagacgat    1680
caggtggtca atcagcatta aacggcgag ccattttact actacatcaa ccaggaagta    1740
tacagtatgg gcgattacgt ggtgaagccg accaaaattg ttgtgacgga cctgctaccg    1800
gagcatgtcg agttgattcc ggacaataac aacagtcccc cgacttatca aaaagcgttc    1860
cagctcttta atgcaactga tccggatgcg gttggccaag atcggaaaat gacgctgact    1920
gaggacgtgt cggattttgt cgtgacgcaa gaaggcgatc ggcagcgaat cacgctgaca    1980
atcggacgtg aagatgtgca gaaaattcat tttcatagcg gctttttctc acttcgattg    2040
aaggtgcggc caacaaagga tccggacacc ctgacaaaac gacttacgct ggtcaataaa    2100
gcgaccgtta aattttcga cactgaggaa cgttacagta aggaaaccaa cgcagtgcag    2160
gttcatcttg atccggcagg cagatttcca gctgaattta ccaagaaaaa ccagtatggc    2220
gcagtgctgc cgggtagtcg gtttgtcttg aagcaaggag acactcaact gcaaacagca    2280
actgccgatt cgcagggtaa agtctcattt ggaacgctaa aacccggcga ctatcaggta    2340
agcgaaattg ccgctgccgg tcacgagttg caggctgaat ttgatttaaa agtggcagct    2400
gacggtactg tgacagtcgg ccgcaacggc gagatttggc cagacaccac ggtgatcaac    2460
caactgaaac ccaccgaact tgagttgatc aaaattgaaa aggtaaaaa caaactcgcc    2520 aatgcaagtt ttgccttata ccgtggcgat caaaccaccc ctgttgctca aggaacgact    2580
gatgaaaatg ccagttgcg attcacacat cagttgaccc cgggaactta tcgcttaacg    2640
gaaaccaaag cgcctgccgg atttgatcgg ctgaacggat cgtttacctt caagattaac    2700
gcgcatggca caatggtaga tcttgcgtat agtggcagcg atttaagcag tgatgagtat    2760
gggtttgaat ttatccctga tgcagaggat aagttgaatc ggattcgctt cacactgacg    2820
aaccattcgt tggaaacact cctaccgaaa actggtggta gcggtatctt gctgtttctc    2880
atggtcgcaa tcagtgcgtg tggcggcggc tggctgcttt acctgtatct gaagcgaaag    2940
gaggcccgtt aa    2952
```

<210> SEQ ID NO 17
<211> LENGTH: 6894
<212> TYPE: DNA
<213> ORGANISM: Lactobacillus rhamnosus

<400> SEQUENCE: 17

```
acgatggttc agtgcggatt ggactgcttg aatttcaacc agggtaactg ctctgaggga     60
cttccctttc gggaagaatt ccctaagcag tccattggcg ttctcgtttg tgccacgctc    120
ccaaggcgag tacggatgtg cgaagtaaat ctgggttcca acaatctctg ataacttggc    180
aaactcggaa ccattgtcaa agtgatact ctcaaattcc ttggccccgt agtcgtcgat    240
cgtgtcctgc aaggctttaa ggcaggtgtc cgcatgatag tcaggaatct tgacgatgat    300
ctcagtccgg ctgtaccgtt ctgtgagcgt cattaatgct ggctcatcag ctaagcgaat    360
acctttgacc aagtcgcctt cccaatgtcc cacgcctgtg cggtcattca cggccgcagg    420
acgcaactcg attgagtcgc cgtatatctt cttattcttg cgcttgtggg cgttcttata    480
gcctttgatg cggcgtcgga gcttcttggg aagtgtcatg ttgtctagcg caagcagccc    540
ggcgtcgatg tagcgataca cagttgtcgt tgaagggcaa gccttgccct ggtcgcgata    600
```

-continued

| | |
|---|---|
| gaagtgtacg aagctatcaa cgctgtgtac gcgcggctta cgagtaagct ccctggcgag | 660 |
| agccttgaag aacgcacggc cggtcttaag aaaggcgtag tgaccggttc tatcgcgttt | 720 |
| acggtcgtgc atggcttggg cagtttccgc aagatagact tgatgcgagt gacgcttcga | 780 |
| gtcgagctga gttacagatc cacgcgtgat ttctcgtgag attgtcgctt tactgcgatg | 840 |
| aagcttctgt gcaatcacgg tcgcggtgtc accagcagcc tgaagggcct gaattgtagc | 900 |
| acggtcgcta aaactgagtt gttggtaatg cttgtgggtg ttagtctgag agtgggtcat | 960 |
| gaagattcct gctttcttgt ttagctagca ctaacaagaa taggtcttca tggcctttat | 1020 |
| ggtctagtcg tcagggtgtt gcacttgaat tgtaaactgg ggttaaaatt ttacttgaga | 1080 |
| ggagggtaaa atttacgaag atgacagcta agtggcgag aactgggcat tgttcgcgg | 1140 |
| tcttattgat tttgatgagt atgttaacag gcttagtgac aagtggcagt tcagttgtga | 1200 |
| cagccactga taacattcgc ccaacctatc aaaccgatgc taatggtacc tatccgacaa | 1260 |
| attcgtggca ggtcacggga caacaaaatg taatcaatca acgtggcggg gatcaagttt | 1320 |
| cagggtggga taataataca atatggaatg gtgatgcgac tgataccacg aactcttacc | 1380 |
| tgaaatttgg tgaccccaat aatccggatt atcagattcg aaaatatgct aaagagacga | 1440 |
| ataccccctgg attgtacgac gtttatttga acgtcaaagg caataaacag caaaatgtga | 1500 |
| agcctgtaga tattgtctta gttgttgata tgtctgggtc aatggagtca aacagatggg | 1560 |
| gcacgaatcg agctggtgct gttcgtactg gcgttaagaa tttcttgact tctattcaaa | 1620 |
| acgccggtct gggtaattac gtcaatgttg gtttaattgg gttttctagt cctggttata | 1680 |
| tcggtggcaa atcgggttat attagtgtca aattaggcaa agcaggtaat gccagccagc | 1740 |
| aacaagcgat taatggtgca ttgagtccaa ggtttcaagg gggtacgtat acgcagattg | 1800 |
| gtttgcggca aggatcagcc atgctgaatg cggacaccag tggcaataaa aaaatgatga | 1860 |
| ttttgttaac tgatggcgtg ccgactttt ctaacgaggt gataaattca gagtggataa | 1920 |
| atggtacatt gtatggcact aattttggat ccagcagaga tgaaccaggg aacaccgcac | 1980 |
| gacttcgatg gccatacacc gatagttcag gtcattatat atatgatact tggccagcaa | 2040 |
| cattgggtga ggccaagata gcaaaggata gtggtaatga ggtgcacgcg ttaggcatcc | 2100 |
| aactggctga cgacgaccac tacatgacga aagaaaaaat acgccaaaac atgcagctta | 2160 |
| ttaccaattc accggattta tacgaagatg ctgatagtgc cgatgctgtt gaggcttatt | 2220 |
| tgaacaatca ggcaaaggac attatcaaaa actttaatac tgtcaccgac ggcacgatca | 2280 |
| cagacccgat tggtacgcaa tttcaatatg cgaacaacca ggcgaccgtt acgagtgtcg | 2340 |
| gcaagcaaac tgtgccagca agtgagttgc caagtgcggc gatccaagat ggtcaattga | 2400 |
| cggtgaatca catgaacttg ggtcaggatc aggaagttca aatccattat caagtacgga | 2460 |
| tcaaaacaga ggatgctggc ttcaagcctg atttttggta ccaaatgaat ggtgaaacat | 2520 |
| tgttgacacc aaaagcgggc gctgccgctg ttgactttgg gattccttca ggcagggcac | 2580 |
| cagcaactac agtttatgtg cagaagcaat ggcgccagtt aagcaatcaa tcgttaccgg | 2640 |
| atacgctcaa cgtcacggtg cagcgaaaag tggctgacgg ttcgcttgat ccaaattggc | 2700 |
| aacagacctt agtccttaaa aaagctgata actggaaagc tagctttacg gcacctgcgt | 2760 |
| ataacaatca gggtcaaagt ttttcatatg tcgttaagag tgaagatgcc tcgggaattg | 2820 |
| atttgagttc gtttatcagt tctcaaaata tggatcagca aacagcaacg ttgactttga | 2880 |
| caaatcagca gtatggtttt cagtttcaga aaaaaacaac cgatggtact gatttatcag | 2940 |
| cagatcagtt gaaggccatg cagtttaact taacccagta cagcgataac agttttcagc | 3000 |

```
aggcatccaa aaccaacgcc atcacgtcaa cggatctgca ggcactagcg ccagggtatt    3060
acggtattca ggaagctgca gcacctacag gttatcaact tgatgggaca acgtatcttt    3120
ttcagctaac gtctgatggg caatggcaat accatggcac aaaggacaat gtgacatcag    3180
ggagtgttat taatggccag cagactttga atcctgttgg tgataagtca gatgatttta    3240
cggtgaccgg ggatcaccag caaattctga cgctaacgaa atatgatgaa ccaaagccat    3300
ccatgacttt gcgggtcatc aaacaggata tcaaagcca atatcttgca ggtgcagcgt     3360
tcaccctgca accaagtgct ggcgaagctg agacgataac atcatcggcg acatctgagg    3420
gacaagcgtt tgcgacaaaa ttagttgcag atggtaccta tacgatgtca gaaacaaaag    3480
caccagatgg ctatcaaagc aatcctgcaa agattgccat tcaggtagct acgactggta    3540
aagaggcaac cgtcacgatt gacggtgagg cattgaagcc gggcgaaagt aagaacggat    3600
acacattagc gattgatggc agcacgatca cttttgcaggc gattaatcag ccacttgcaa    3660
ttttgccgca tacaggtggt cagggctatc agcgattgct tggtatcgca ctgggattga    3720
tcagcgcagc gttccttta ttactggttg ttttgataaa gcgacgggtg gtgaagcaac      3780
atgactaaat ccttccgtcc gttagtgatt ttgacctttt gcttggcact actagtcagt    3840
ttggcaacga caacgttgca gcagacacag gcggcaactg tgccgaccac tgttgatgtt    3900
gtgttgcata agctgttgtt taaagatacc ttgccaactc aacaagcaaa taacgggaca    3960
acaaaacccg acttttcgca ggcagatgtg ccgttaaacg gtgtgacgtt cacagtttat    4020
gacgtgaccg ctgactttg gcagcttgtc tccaaaaatg gcggtgcgat tgaggtagca     4080
caaacgacgt tgagtcaaga tagctatcag cctgctagct ccagccttat cgcacaggtt    4140
gtgacggctg gtcagggaga gcgtacttt ggcgatttac cactccgaca ggggcagcat     4200
gctgcggttt atctttttaa agaaacggcg gcacctaaga atattgaagc cagtcagaat    4260
cttgtggttg tcatgtcaag caaccttcaa catgggaatc aatcacgcat tgatttattt    4320
cctaagaaca aaatggtaag tcgtcacacc gatgccccca aaaagttcc aaagaaaata     4380 cgtcaattgt tgccacaaac gggtgataca gttgcagctt ggctttcagt gctcgggttg    4440
ataatcttcg cgacagtact tgcttttaac ataaaaaacc aaaaaattaa taagtgggag    4500
agataagaat gaaaagaca attgccaaga aagtgctgac attaaccagc acgatcctaa    4560
tgacattact gatggttctc gggtttaatg gcactcgggt tcaagcagat acgaatgata    4620
cgacaacaca aaacgttgtc cttactaaat acgggtttga caaagatgtt actgccattg    4680
atcgtgcgac tgatcaaatt tggaccgcg atggtgctaa gcctttacaa ggcgttgatt    4740 tcaccatta caacgtgaca gccaattatt gggcatcgcc taaggattat aaaggcagtt    4800
ttgatagtgc tccggttgcc gcaaccggta cgactaatga caaggggcaa ctaacccaag    4860
cattacctat ccaatcaaaa gatgccagtg gtaagactcg tgctgctgtc tatcttttcc    4920
atgaaaccaa tccgcgagct ggttataaca cgtctgccga tttctggtta accttaccag    4980
ccaaggcagc agccgacggg aatgtctatg tctacccaaa gaatgttcaa aagaccacct    5040
atgagcgcac ttttgttaag aaagatgctg agactaaaga agtgcttgaa ggagccggct    5100
ttaagattag caatagtgat ggcaagtttt tgaagttgac agataaagat ggtcaaagcg    5160
tcagcatcgg cgaaggattt atcgatgtat tggccaataa ctatcgattg acgtgggttg    5220
ctgaaagcga tgctactgtt ttcacgtctg ataagagcgg taagtttggc ttaaatggat    5280
ttgctgataa caccacaact tacacggcag ttgaaacaaa cgtgccggat ggttatgatg    5340
ctgctgccaa tacagacttt aaagctgata attcgtctag cgacattcta gatgcaccaa    5400
```

```
gcggtattct gccacacact ggtggtactg gcacagtcat ttttgcgatt ttgggcgttg    5460
ccttaattgc atttggagca gttgcctatc gcaagcgccg caatggtttc taaaaagtta    5520
ataagataaa tgagtcaagc aagagcgtcg atggcgctct tgttttgata tggcgaggta    5580
atcagagtga caaaacgaac acgtcgacct ttagacttga ttgatattgt gattggatgt    5640
cttcttttag cgggttttgg tgttttatgc tatccatttg caagtgatgc ttacgtttct    5700
taccaaaatc agcaagtcat cgacaggtat cgacaacaag aagcgcggaa gaatcagatg    5760
gtgttgcggc gggaatataa cgactatcag caaaaaaata aacagttggc agcaagtcaa    5820
caagtgcccg gcgttgccag ttttaatcat gctgttaatg atcaaggaac cgcaaaaaca    5880
gcagccaaac gcaatcaaca aatcttgact cggcagacag ttgctcagtt gacgattccc    5940
aaaattggcc ttagtctgcc ggttttgat catacaagcg attggcttct acaatttggc    6000
gcctgtttat tggatggtac aagttatcca actggtggta aaaatacccca tgctgtcatt    6060 tcagcgcatc gtggtgtgcc aaacgctgaa cttttaccc gagtaccagc gttaaaaaaa    6120
ggcgacaagt tttttattag cataggcaat cataaattgg cttaccaagt ctttaagcgc    6180
caggttattg agccaagtga tacccggcag ctaagaattg tgccgggaca ggatcttgtg    6240
accttaatga cctgcacgcc ttatatgatc aattctcatc gattgttgat aacgggtcgc    6300
cgaattcctt acgttaaggc agatgaagag gcttcaagtt gggcggtttg gtggaacaaa    6360
ttaaagctaa tagtcgcact tttaggcgcg gtgatcattt taggcgtgat cggtttcgta    6420
atgcgcagtt tgatgcttgg ccgaaagcat tatttgctgg aagtaccggc tgaagccaca    6480
caagtcgtgg tgaaacgagg tcgacatata cattcttta aatcagatca aactggggtg    6540
actgacatca gcctgcctgg taatcattat cgagtcgcaa ttgtcacacc gcttggccgg    6600
actaagtaca aggcttatgt caaaaaaatt cgggataaaa gctttcaatt aaaagaatat    6660
cattaagatc ttaaaatttg tttaatatcc ttttgggtta atttaaatga ggaaaggatc    6720
aatattttaa gactgatatt gagtttaata aactaaaaac gaccaactta ttaaaacact    6780
atgtctgtat atttcaagct tttgaagtag gacgatgcaa catgaatgag tattagaaaa    6840
ccggttcatc aaagatgact ttccatagtg gaagccgtct tttttgatat ttaa           6894
```

<210> SEQ ID NO 18
<211> LENGTH: 7540
<212> TYPE: DNA
<213> ORGANISM: Lactobacillus rhamnosus

<400> SEQUENCE: 18

```
gcccatggta ctgccgagtt cactgttgac ggggcgcagt tgcgtattca tattgagatg      60
tttgatacac ctgcaaacgt ccagcattgg gaacacttcc atggttttcc ggatggcaag     120
ccagctgaga tagccaccgc ggcccaagat gctaatggtg acggctttgt tgatttacct     180
gaaacggaac cggtttccgg tacaacgatg gtcccgtttg atgccgagcc tgctaaaatg     240
cacgtaccca atgacagcta tccagtagcc gatgctgacg ggcactatgc ttatgacaag     300
ctcgtggatt taaagagct gcagaaggcg ttcaaggcag catttggtag tgaagatttg     360
caattagata acgggttgt ttacattcat ggtgttccgg acagtttgga acttccagat     420
acggttaaag gaaccgtcat gaactatgat gcacacgtca cactgccaat tgccgtgggt     480
aaaattgtcc gcgcttagta gcaaaatata atttaataac gtaggttgtt cccgatccgt     540
ctgagcgttt ccagcttagt caggtcggga ttttttgtgc gccaaatcct aaaacttata     600
aatactggaa tgatcattca tatattcgct gctaattata atttaagaag taatataccg     660
```

-continued

```
aagaaaactt tatttataaa ataacaatta ttatagttcc gtttacgcag ttcatcttgt    720
tacgcttaat tcagcaacaa gtgaaaaatg taacatgaaa ggaggcaccc gattgcctag    780
gaaatggatt catatgctga tgttactgct gatgctggtc acgcaaattg cagtgccgc     840 ggtcccggta gccaaaagcg ctcagactaa tccaaagcac gatgtccggg atgcgtcagt    900
gcagccgagc actcgtcctg ccgcatccga agctgctgag tttgatctgg aagcagcggc    960
tagtgcgcca tcaaccagcg cggccgccaa gcaaactact tcaaaagctc ggcagcacat   1020
caagctagaa gcagggaagt cttggcacgg cgatggtcat acgttaactt acaacgttga   1080
cattcagcgg tctgaaattc aggttaagtt gattttagcc aagccacagg atcaaacggg   1140
gcagcaagtc gtcaagttcg ctaatgccca aggattcacg tcccagcctg cacatactaa   1200
cggtgaaata acgcgccggc ttgcagagaa acggcagaa aaaggtgaat acctttaac    1260 caaaaagctg cctgatacaa agcagcaagc agctagtgtg aaactcagtc tggatggatt   1320
taatgacgct gctcaggtat tagcgcttga tgttgacttg cagctgcctg cgcgcctggc   1380
taacgatgat gtgcaggaac cggctgcact cagcaaagat gcgcacagtc tgattttacc   1440
gccgtctgca cttgggacga ttaaaattca cgcaactaaa gctgatggcg ccgcactttc   1500
ggatgaagag gcgcaaattt atcgcaaacc aaatagtagt acccgttcaa aatacggatc   1560
acgttgggcg atggagaatg gcgtttcatc agattatgtg tcgcgttctg atgccaccgc   1620 cattatttt aaagatgcgg ttcaaaatcc cagtggtcct tctaacctgc tagatgccaa   1680
gatcaaagtg gatattgatc atgttggctc agcaagtgat cttgatggaa accgttttga   1740
gattggtgct tatgttgaac taacaggtat tcgcgtccgt ccagtcgaat ggggcactac   1800
ccctcaggat gtcggcattg attttccaa caacttcttt tccgggatgt catttgccaa    1860 tgtttgtac tatgactggc gcgtgatttt ttatgacaag gcaacgagac agcgattgaa    1920
ctttattccg caaagtgaag ccaatcaaaa ttcgaccctg acgttacttt cgttgaatcc   1980
cggtgagttt gtctggacgg agcaggcggg gatgacgccc acttatgacg atcggtttat   2040
cacggattgg caatttgagg aaggaacctg gattacctca gataaagcga cattcgaaac   2100
cgaaaaactg ggcgctcgcg ggaaggaaca acgtgggtac acctcacaga cctggggaaa   2160
ctgggtcgat ccaattgatc acgagaatat gacggaatgg gaagatcgac taggtgcgcc   2220
aacatttggg cgtggtgccg ttgcgtttac tttaaacggt accagtcata cctttagacg   2280
cggcacttat tccaacggcg gcggtacttg ggttgccaat gggagtggac aaatcgagtt   2340
gattgaccca aatgtcacca acaacaaaag cgtgagcgca aatgccgaag ccggtggcgg   2400
agccgaggaa gataaaaccg gcaccatctg gaccgcaaat gatttagacg atcaggtggt   2460
caatcagcat tacaacggcg agccatttta ctactacatc aaccaggaag tatacagtat   2520
gggcgattac gtggtgaagc cgaccaaaat tgttgtgacg gacctgctac cggagcatgt   2580
cgagttgatt ccggacaata caacagtcc cccgacttat caaaaagcgt tccagctctt   2640
taatgcaact gatccggatg cggttggcca agatcggaaa atgacgctga ctgaggacgt   2700
gtcggatttt gtcgtgacgc aagaaggcga tcggcagcga atcacgctga caatcggacg   2760
tgaagatgtg cagaaaattc attttcatag cggcttttc tcacttcgat tgaaggtgcg    2820
gccaacaaag gatccggaca ccctgacaaa acgacttacg ctggtcaata agcgaccgt    2880 taaatttttc gacactgagg aacgttacag taaggaaacc aacgcagtgc aggttcatct   2940
tgatccggca ggcagatttc cagctgaatt taccaagaaa aaccagtatg gcgcagtgct   3000
gccgggtagt cggtttgtct tgaagcaagg agacactcaa ctgcaaacag caactgccga   3060
```

```
ttcgcagggt aaagtctcat ttggaacgct aaaacccggc gactatcagg taagcgaaat    3120
tgccgctgcc ggtcacgagt tgcaggctga atttgattta aaagtggcag ctgacggtac    3180
tgtgacagtc ggccgcaacg gcgagatttg ccagacacc  acggtgatca accaactgaa    3240
acccaccgaa cttgagttga tcaaaattga aaaaggtaaa aacaaactcg ccaatgcaag    3300
ttttgcctta taccgtggcg atcaaaccac ccctgttgct caaggaacga ctgatgaaaa    3360
tggccagttg cgattcacac atcagttgac cccgggaact tatcgcttaa cggaaaccaa    3420
agcgcctgcc ggatttgatc ggctgaacgg atcgtttacc ttcaagatta acgcgcatgg    3480
cacaatggta gatcttgcgt atagtggcag cgatttaagc agtgatgagt atgggtttga    3540
atttatccct gatgcagagg ataagttgaa tcggattcgc ttcacactga cgaaccattc    3600
gttggaaaca ctcctaccga aaactggtgg tagcggtatc ttgctgtttc tcatggtcgc    3660
aatcagtgcg tgtggcggcg gctggctgct ttacctgtat ctgaagcgaa aggaggcccg    3720
ttaagatgcg acgattttat tggtggcttg tcccgttgct tctattgatt ggtatcgtgc    3780
ttggcaacac accacattgg gttcacgcgg ctgatcaaac tgccgagatt gtgatccata    3840
agcgaattta tcgggatatt cgccaaccgg aagacgtttg gtatgaaaat gacggtcatc    3900
ggattgaccc gaataacccg gataaagatg gctacaaatt attaagcaaa accagcgggc    3960
tgaatggtgc taactttgag gtctatgatg ccagctcctt attgaaaccg aatatgacgc    4020
ctgaagcaat tcgggctttta gttgatcgtt atcagaatat gacgcgtaag caagcactga    4080
aatttgcgcg ggccaacctg aaattagccg gtcaagggaa caaaggtatc gggctgatga    4140
atacaaaaaa cgatccaaca ctcggtgaag atgggatcag ccgaataacc gtttctgtcg    4200
atcaacaggc accgactaaa gcttatctga tgatcgaggt ggcaccggat ccttcaaccg    4260
aactcaatgt ggacttagag cgcaaaagtt cgccgatgtt agttgttttt ccagtcacgg    4320
atcctatcag tggcaacccg ttacagacca tccatctgta tccgaaaaat gtcggttatg    4380
tccgcgatcc gtatttcttc aagttcggcg tgcaccctga tggtacgagt aaacggttag    4440
ccggtgcgat ctttgctatt taccgaattg agaatggtaa gaagctttat ctcgatatgt    4500
cgccagtaac cgacttgcgc aacaaatggg tgagcactac tgatccgttg catgatgacc    4560
gcgtgaacaa atttgtttcc gatcaagatg ggctagttaa tacaggtgaa cgcttttgc     4620 ccgccggaga atatttcttt gaagaattgc aaggcgttcc cggctatgaa gtggatgcta    4680
aaagccgcgc gatcaaaatc gagattcctg attcttggga agacgaagat ggcaaccggc    4740
gctttgtgtt aattgacggc cagccgatgc aggaaaactt tggcggggtg gtgacaccgg    4800
aaatgatcag tagcggctac ccgcgagttt ataactatgc cgataagcag gcgtcgacaa    4860
ccggtgatca aaccgcgggg ccatcaacga cccagcttgg caatcacggg caggatacga    4920
acggcaccgg aacgcgtaca cctaagcgtc aatccggtta tttgccggcc atgtccgatt    4980
ggcgcaattt acgctttgtc ctttttaggga gtctgttact actactgcc  acttacttct    5040 tcattaaaaa taagaaagcg aggcaccacg catgcaagta acgtttaaaa agatcgggca    5100
cagtctcttg gcagcgctga tgctcatgag cttccttcta ccactgctta gtgcgggcaa    5160
acccgtacat gccgcgacaa cgactgtgga tttcacgctg cacaaaatcg aacaaaccag    5220
tgacgaacag attcaaaata ccggccacga ccttggactg accggcgta  aaccggtgca    5280 aggcgctcaa tttaaaattt tcaacgtgac ggacgccttt taccaattac tggaaaatca    5340
tgataagaca accgctgcga gcatgatatc gcaaaacctg ggtcagtatg tgaatctcca    5400
ggatcctaat gcagcaactg tcacgactga tgcagacggc ttggcggcat tcaaaggatt    5460
```

-continued

```
agccgccaaa accaatggcc ggcatagcgt gtacgcattt cacgaagccg tgaccccgca   5520
accgtatcaa aaagcagcag atatgatcgt gagtctgcca gtgcggcaag acgatggatc   5580
ggatctgacc aacattcatc tttatcctaa agacagtctt gttaccaaaa atctgacgga   5640
aatcaatgaa caagcggtgg caacaaaaga tctccatgat gtcgcggttg gcgatgtgct   5700
cacgtatcag gttcagttcc agattccgca tgatattggc gcgctggctg atcacagtca   5760
agacactttt aagtacaacc aatttaaagt gctggattat atgaccaagg aaggccttac   5820
tttttaaggca ttgacggcaa tcacggttga cggtcaggac attttaaagg cattaaccgg   5880
aaaaatggcc ttcatgagtt ctaatgacgc agcttggcaa caaacacaca actatccatt   5940
cgggtttgaa ctggactttc taggcgggac cgatcccgat gcggtacgaa acctgttgac   6000
ccaatatgcc ggcaaacgcg tgaccgttgc ctacaccgga atcgtcaatg agaaaatgat   6060
cccagaccaa aaagtcggta acacggctga agtgagcttt gatcctgaca gcaagattac   6120
cgtcaatggt ccggaaatcc agactggcgg gattcggttc ttcaaacacg aagccggatc   6180
ttccaaaagt ttggccaacg cgactttcat cttacagcga atgaacggca atgtgcgcga   6240
atatgcagtt cttgaaggcg ttaacggtat ggccggaacc taccaaccga ccaagattac   6300
ctggacaacg aatcaagacg cggcaacgag actcaaaacc agtggagccg agacagccaa   6360
cttaaccatt caagggctgt tgccagggcg atataccttg gttgaaaccg cggcaccaga   6420
aggctatgaa atccttgatc cgacaacaga ttttgaagtc attgccggta cttggggtac   6480
gaaaacgatt cgcatcgcca acacgccggt gaatcaatta ttgccgatga caggcggaat   6540
cggactcttc gccttcctga tgatcggggc catcttaatg ggtggcggtc acctaatgaa   6600
gaaaaagacc agcaagaaag tctaatggcc tatgacaaaa aaagcgtcgg ggacaagtcg   6660
gctgttacgc tggttcgtca tcttactttt tactgcggga gccgcgtgtt tctgctatcc   6720
gttcgcggca acggctatta atgaattgct actaaccagt cgccgagcag cagcacagca   6780
agaagccaag caaaatgccg ccgcccaaga tgagcaacgg gcagcggaga accgtgcact   6840
tgcccagact ggtttgcgtc cgggacagga tccgtttcaa agtaggcaga aatttaacca   6900
agcctatgtg aaacggcatc tgatcgggcg agtggttatc ccgaaattag cggttgatct   6960
gccccttttt gacaccacca acaacacgct gttagatcaa ggggcagtgg tgttaccagg   7020
tactagctat ccgcggggag gcaagaacac gcatacagtt gtttcggcac acggcggctt   7080
gcccaccaaa cgcttttttca ccgatctgag caagttgaaa cgagggcaga agttcttttct   7140
ccaagtcaac ggcaaaaaga tggcgtatca ggtctttcgg atcaaaaccg tgcggccgga   7200
tgaaacccag agcttgcgca ttgaaccggg acgcgatttg ccacattaa tgacctgtac   7260
cccgtatatg atcaactccc accgcctgtt agtgaccggc aaacgggtac cttataccga   7320
atcacttgag cacgccgccg agtctgctga tcgctggcgc ttgtggttaa gtatcgcggt   7380
tgtcgtcgga gtgctgggat tggcattgct gagtttctat ctggctcggc gctatcttcg   7440
ccgaccgcgg gcgtaatctg gaaagagaat gttagaaagt aagaaagttc gccgttgtgc   7500
agggataggt ctgtggacgg cgggcttttt tgtgtttcga                          7540
```

<210> SEQ ID NO 19
<211> LENGTH: 30
<212> TYPE: DNA
<213> ORGANISM: Artificial sequence
<220> FEATURE:
<223> OTHER INFORMATION: Oligonucleotide

<400> SEQUENCE: 19

-continued

```
tcgggttcag aattctacga atgatacgac                                    30
```

<210> SEQ ID NO 20
<211> LENGTH: 30
<212> TYPE: DNA
<213> ORGANISM: Artificial sequence
<220> FEATURE:
<223> OTHER INFORMATION: Oligonucleotide

<400> SEQUENCE: 20

```
tgccagtacc accctcgagt ggcagaatac                                    30
```

<210> SEQ ID NO 21
<211> LENGTH: 28
<212> TYPE: DNA
<213> ORGANISM: Artificial sequence
<220> FEATURE:
<223> OTHER INFORMATION: Oligonucleotide

<400> SEQUENCE: 21

```
gcagacacag aattcaactg tgccgacc                                      28
```

<210> SEQ ID NO 22
<211> LENGTH: 34
<212> TYPE: DNA
<213> ORGANISM: Artificial sequence
<220> FEATURE:
<223> OTHER INFORMATION: Oligonucleotide

<400> SEQUENCE: 22

```
caactgtatc accctcgagt ggcaacaatt gacg                               34
```

<210> SEQ ID NO 23
<211> LENGTH: 33
<212> TYPE: DNA
<213> ORGANISM: Artificial sequence
<220> FEATURE:
<223> OTHER INFORMATION: Oligonucleotide

<400> SEQUENCE: 23

```
cagttcagtt gtgaattcca ctgataacat tcg                                33
```

<210> SEQ ID NO 24
<211> LENGTH: 31
<212> TYPE: DNA
<213> ORGANISM: Artificial sequence
<220> FEATURE:
<223> OTHER INFORMATION: Oligonucleotide

<400> SEQUENCE: 24

```
agccctgacc accctcgagc ggcaaaattg c                                  31
```

<210> SEQ ID NO 25
<211> LENGTH: 28
<212> TYPE: DNA
<213> ORGANISM: Artificial sequence
<220> FEATURE:
<223> OTHER INFORMATION: Oligonucleotide

<400> SEQUENCE: 25

```
acccgtacag aattcgacaa cgactgtg                                      28
```

<210> SEQ ID NO 26
<211> LENGTH: 31
<212> TYPE: DNA
<213> ORGANISM: Artificial sequence
<220> FEATURE:

```
<223> OTHER INFORMATION: Oligonucleotide

<400> SEQUENCE: 26
gtccgattcc gccctcgagc ggcaataatt g                               31

<210> SEQ ID NO 27
<211> LENGTH: 31
<212> TYPE: DNA
<213> ORGANISM: Artificial sequence
<220> FEATURE:
<223> OTHER INFORMATION: Oligonucleotide

<400> SEQUENCE: 27
ccacattggg ttcagaattc tgatcaaact g                               31

<210> SEQ ID NO 28
<211> LENGTH: 30
<212> TYPE: DNA
<213> ORGANISM: Artificial sequence
<220> FEATURE:
<223> OTHER INFORMATION: Oligonucleotide

<400> SEQUENCE: 28
tgcgccaatc ggactcgagc ggcaaataac                                 30

<210> SEQ ID NO 29
<211> LENGTH: 29
<212> TYPE: DNA
<213> ORGANISM: Artificial sequence
<220> FEATURE:
<223> OTHER INFORMATION: Oligonucleotide

<400> SEQUENCE: 29
gcaaattggc aggagctcgg tcccggtag                                  29

<210> SEQ ID NO 30
<211> LENGTH: 28
<212> TYPE: DNA
<213> ORGANISM: Artificial sequence
<220> FEATURE:
<223> OTHER INFORMATION: Oligonucleotide

<400> SEQUENCE: 30
ccgctaccac cctcgagcgg taggagtg                                   28

<210> SEQ ID NO 31
<211> LENGTH: 20
<212> TYPE: DNA
<213> ORGANISM: Artificial sequence
<220> FEATURE:
<223> OTHER INFORMATION: Oligonucleotide

<400> SEQUENCE: 31
tctcgggttt aatggcactc                                            20

<210> SEQ ID NO 32
<211> LENGTH: 20
<212> TYPE: DNA
<213> ORGANISM: Artificial sequence
<220> FEATURE:
<223> OTHER INFORMATION: Oligonucleotide

<400> SEQUENCE: 32
tctgtattgg cagcagcatc                                            20

<210> SEQ ID NO 33
```

```
<211> LENGTH: 20
<212> TYPE: DNA
<213> ORGANISM: Artificial sequence
<220> FEATURE:
<223> OTHER INFORMATION: Oligonucleotide

<400> SEQUENCE: 33
tccttccgtc cgttagtgat                                                    20

<210> SEQ ID NO 34
<211> LENGTH: 20
<212> TYPE: DNA
<213> ORGANISM: Artificial sequence
<220> FEATURE:
<223> OTHER INFORMATION: Oligonucleotide

<400> SEQUENCE: 34
cgtttgtggc aacaattgac                                                    20

<210> SEQ ID NO 35
<211> LENGTH: 20
<212> TYPE: DNA
<213> ORGANISM: Artificial sequence
<220> FEATURE:
<223> OTHER INFORMATION: Oligonucleotide

<400> SEQUENCE: 35
ccaaattggc aacagacctt                                                    20

<210> SEQ ID NO 36
<211> LENGTH: 20
<212> TYPE: DNA
<213> ORGANISM: Artificial sequence
<220> FEATURE:
<223> OTHER INFORMATION: Oligonucleotide

<400> SEQUENCE: 36
gccatctggt gcttttgttt                                                    20

<210> SEQ ID NO 37
<211> LENGTH: 20
<212> TYPE: DNA
<213> ORGANISM: Artificial sequence
<220> FEATURE:
<223> OTHER INFORMATION: Oligonucleotide

<400> SEQUENCE: 37
cggacgcctt ttaccaatta                                                    20

<210> SEQ ID NO 38
<211> LENGTH: 20
<212> TYPE: DNA
<213> ORGANISM: Artificial sequence
<220> FEATURE:
<223> OTHER INFORMATION: Oligonucleotide

<400> SEQUENCE: 38
aacaggtttc gtaccgcatc                                                    20

<210> SEQ ID NO 39
<211> LENGTH: 20
<212> TYPE: DNA
<213> ORGANISM: Artificial sequence
<220> FEATURE:
<223> OTHER INFORMATION: Oligonucleotide

<400> SEQUENCE: 39
```

```
tatgacgcgt aagcaagcac                                              20

<210> SEQ ID NO 40
<211> LENGTH: 20
<212> TYPE: DNA
<213> ORGANISM: Artificial sequence
<220> FEATURE:
<223> OTHER INFORMATION: Oligonucleotide

<400> SEQUENCE: 40
tggccgtcaa ttaacacaaa                                              20

<210> SEQ ID NO 41
<211> LENGTH: 20
<212> TYPE: DNA
<213> ORGANISM: Artificial sequence
<220> FEATURE:
<223> OTHER INFORMATION: Oligonucleotide

<400> SEQUENCE: 41
ctaccggagc atgtcgagtt                                              20

<210> SEQ ID NO 42
<211> LENGTH: 20
<212> TYPE: DNA
<213> ORGANISM: Artificial sequence
<220> FEATURE:
<223> OTHER INFORMATION: Oligonucleotide

<400> SEQUENCE: 42
ggccattttc atcagtcgtt                                              20
```